US008765146B2

(12) United States Patent
Bruder et al.

(10) Patent No.: US 8,765,146 B2
(45) Date of Patent: Jul. 1, 2014

(54) ADENOVIRAL VECTOR-BASED MALARIA VACCINES

(75) Inventors: Joseph T. Bruder, Ijamsville, MD (US); Imre Kovesdi, Rockville, MD (US); C. Richter King, New York, NY (US); Duncan L. McVey, Derwood, MD (US); Damodar R. Ettyreddy, North Potomac, MD (US); Denise Louise Doolan, Camp Hill (AU); Daniel John Carucci, Washington, DC (US)

(73) Assignees: GenVec, Inc., Gaithersburg, MD (US); The Henry M. Jackson Foundation for the Advancement of Military Medicine, Inc., Rockville, MD (US); The United States of America, as represented by the Secretary of the Navy, Washington, DC (US)

( * ) Notice: Subject to any disclaimer, the term of this patent is extended or adjusted under 35 U.S.C. 154(b) by 1259 days.

(21) Appl. No.: 12/064,554

(22) PCT Filed: Aug. 31, 2006

(86) PCT No.: PCT/US2006/033982
§ 371 (c)(1), (2), (4) Date: Oct. 27, 2008

(87) PCT Pub. No.: WO2007/027860
PCT Pub. Date: Mar. 8, 2007

(65) Prior Publication Data
US 2009/0148477 A1    Jun. 11, 2009

Related U.S. Application Data

(60) Provisional application No. 60/713,110, filed on Aug. 31, 2005.

(51) Int. Cl.
| | | |
|---|---|---|
| *A61K 39/00* | (2006.01) | |
| *A61K 39/002* | (2006.01) | |
| *A61K 39/015* | (2006.01) | |
| *A61K 39/38* | (2006.01) | |
| *A61K 45/00* | (2006.01) | |

(52) U.S. Cl.
USPC ............ 424/272.1; 424/184.1; 424/185.1; 424/187.1; 424/191.1; 424/233.1; 424/268.1; 435/235.1; 435/258.2

(58) Field of Classification Search
None
See application file for complete search history.

(56) References Cited

U.S. PATENT DOCUMENTS

| | | | |
|---|---|---|---|
| 4,863,457 A | 9/1989 | Lee | |
| 5,168,062 A | 12/1992 | Stinski | |
| 5,378,475 A | 1/1995 | Smith et al. | |
| 5,385,839 A | 1/1995 | Stinski | |
| 5,443,505 A | 8/1995 | Wong et al. | |
| 5,543,328 A | 8/1996 | McClelland et al. | |
| 5,559,099 A | 9/1996 | Wickham et al. | |
| 5,712,136 A | 1/1998 | Wickham et al. | |
| 5,731,190 A | 3/1998 | Wickham et al. | |
| 5,756,086 A | 5/1998 | McClelland et al. | |
| 5,766,597 A * | 6/1998 | Paoletti et al. ............. | 424/199.1 |
| 5,770,442 A | 6/1998 | Wickham et al. | |
| 5,801,030 A | 9/1998 | McVey et al. | |
| 5,837,511 A | 11/1998 | Falck-Pedersen et al. | |
| 5,846,782 A | 12/1998 | Wickham et al. | |
| 5,849,561 A | 12/1998 | Falck-Pedersen | |
| 5,851,806 A | 12/1998 | Kovesdi et al. | |
| 5,871,727 A | 2/1999 | Curiel | |
| 5,885,808 A | 3/1999 | Spooner et al. | |
| 5,922,315 A * | 7/1999 | Roy ............................ | 424/93.2 |
| 5,962,311 A | 10/1999 | Wickham et al. | |
| 5,965,541 A | 10/1999 | Wickham et al. | |
| 5,994,106 A | 11/1999 | Kovesdi et al. | |
| 5,994,128 A | 11/1999 | Fallaux et al. | |
| 6,033,908 A | 3/2000 | Bout et al. | |
| 6,057,155 A | 5/2000 | Wickham et al. | |
| 6,127,175 A | 10/2000 | Vigne et al. | |
| 6,127,525 A | 10/2000 | Crystal et al. | |
| 6,153,435 A | 11/2000 | Crystal et al. | |
| 6,225,113 B1 | 5/2001 | Brough et al. | |
| 6,225,289 B1 | 5/2001 | Kovesdi et al. | |
| 6,329,190 B1 | 12/2001 | Wickham et al. | |
| 6,329,200 B1 | 12/2001 | McVey et al. | |
| 6,455,314 B1 | 9/2002 | Wickham et al. | |
| 6,465,253 B1 | 10/2002 | Wickham et al. | |
| 6,482,616 B1 | 11/2002 | Kovesdi et al. | |
| 6,514,943 B2 | 2/2003 | Kovesdi et al. | |

(Continued)

FOREIGN PATENT DOCUMENTS

| | | |
|---|---|---|
| WO | WO 94/28152 A1 | 12/1994 |
| WO | WO 95/02697 A1 | 1/1995 |

(Continued)

OTHER PUBLICATIONS

Tine et al., (Infection and Immunity. Sep. 1996. vol. 64 (9):3833-3844).*

(Continued)

*Primary Examiner* — Ja'na Hines
(74) *Attorney, Agent, or Firm* — Leydig, Voit & Mayer, Ltd.

(57) ABSTRACT

The invention provides adenoviral vectors comprising an adenoviral genome comprising heterologous antigen-encoding nucleic acid sequences, such as *Plasmodium* nucleic acid sequences, operably linked to promoters. The invention further provides a method of inducing an immune response against malaria in a mammal comprising administering the adenoviral vectors to the mammal.

8 Claims, 7 Drawing Sheets

(56) References Cited

U.S. PATENT DOCUMENTS

| | | |
|---|---|---|
| 6,576,456 B2 | 6/2003 | Wickham et al. |
| 6,649,373 B2 | 11/2003 | Brough et al. |
| 6,649,407 B2 | 11/2003 | Wickham et al. |
| 6,660,521 B2 | 12/2003 | Brough et al. |
| 6,677,156 B2 | 1/2004 | Brough et al. |
| 6,682,929 B2 | 1/2004 | Brough et al. |
| 6,740,525 B2 | 5/2004 | Roelvink et al. |
| 2001/0043922 A1 | 11/2001 | Kovesdi et al. |
| 2001/0047081 A1 | 11/2001 | Roelvink et al. |
| 2002/0004040 A1 | 1/2002 | Kovesdi et al. |
| 2002/0031831 A1 | 3/2002 | Kovesdi et al. |
| 2002/0099024 A1 | 7/2002 | Wickham et al. |
| 2002/0110545 A1 | 8/2002 | Kovesdi et al. |
| 2002/0151027 A1 | 10/2002 | Wickham et al. |
| 2003/0022355 A1 | 1/2003 | Wickham et al. |
| 2003/0099619 A1 | 5/2003 | Wickham et al. |
| 2003/0133912 A1* | 7/2003 | Davidson et al. ............ 424/93.2 |
| 2003/0153065 A1 | 8/2003 | Kovesdi et al. |
| 2003/0219458 A1* | 11/2003 | Wang ......................... 424/199.1 |
| 2004/0096426 A1* | 5/2004 | Chen et al. .................... 424/93.2 |
| 2004/0161848 A1 | 8/2004 | Kovesdi |

FOREIGN PATENT DOCUMENTS

| | | |
|---|---|---|
| WO | WO 95/16772 A1 | 6/1995 |
| WO | WO 95/34671 A1 | 12/1995 |
| WO | WO 96/07734 A2 | 3/1996 |
| WO | WO 96/22378 A1 | 7/1996 |
| WO | WO 96/26281 A1 | 8/1996 |
| WO | WO 97/00326 A1 | 1/1997 |
| WO | WO 97/12986 A1 | 4/1997 |
| WO | WO 97/20051 A2 | 6/1997 |
| WO | WO 97/21826 A2 | 6/1997 |
| WO | WO 98/07865 A1 | 2/1998 |
| WO | WO 98/07877 A1 | 2/1998 |
| WO | WO 98/32842 * | 7/1998 ............... C12N 7/01 |
| WO | WO 98/40509 A1 | 9/1998 |
| WO | WO 98/53087 A1 | 11/1998 |
| WO | WO 98/54346 A1 | 12/1998 |
| WO | WO 99/15686 A1 | 4/1999 |
| WO | WO 00/00628 A1 | 1/2000 |
| WO | WO 00/15823 A1 | 3/2000 |
| WO | WO 00/34444 A2 | 6/2000 |
| WO | WO 01/58940 A2 | 8/2001 |
| WO | WO 01/92549 A2 | 12/2001 |
| WO | WO 03/020879 A2 | 3/2003 |
| WO | WO 03/022311 A1 | 3/2003 |
| WO | 03/064665 A1 | 8/2003 |
| WO | WO 03/064665 A | 8/2003 |

OTHER PUBLICATIONS

Gonin et al., (1996. Vaccine. vol. 14(11):1083-1087).*
Adey et al., "Characterization of phage that bind plastic from phage-displayed random peptide libraries," *Gene*, 156: 27-31 (1995).
Balass et al., "Recovery of high-affinity phage from a nitrostreptavidin matrix in phase-display technology," *Anal. Biochem.*, 243: 264-269 (1996).
Brough et al., "Activation of transgene expression by early region 4 is responsible for a high level of persistent transgene expression from adenovirus vectors in vivo," *J. Virol.*, 71 (12): 9206-9213 (Dec. 1997).
Bruña-Romero et al., "Complete, long-lasting protection against malaria of mice primed and boosted with two distinct viral vectors expressing the same plasmodial antigen," *Proc. Natl. Acad. Sci. USA*, 98 (20): 11491-11496 (Sep. 25, 2001).
Burghaus et al., "Analysis of recombinant merozoite surface protein-1 of Plasmodium falciparum expressed in mammalian cells," *Mol. Biochem. Parasitol.*, 104 (2): 171-183 (1999).
Cadwell, "Randomization of genes by PCR mutagenesis," *PCR Meth. Appl.*, 2 (1): 28-33 (1992).
Carvalho et al., "Malaria vaccine: candidate antigens, mechanisms, constraints and prospects," *Scand. J. Immunol.*, 56 (4): 327-343 (Oct. 2002).
Cheng et al., "Identification of a biologically significant DNA-binding peptide motif by use of a random phage display library," *Gene*, 171: 1-8 (1996).
Cherry et al., "Directed evolution of a fungal peroxidase," *Nat. Biotechnol.*, 17: 379-384 (1999).
Crawford-Miksza et al., "Analysis of 15 adenovirus hexon proteins reveals the location and structure of seven hypervariable regions containing serotype-specific residues," *J. Virol.*, 70 (3): 1836-1844 (Mar. 1996).
Doolan et al., "Circumventing genetic restriction of protection against malaria with multigene DNA immunisation; CD8+cell-, interferon gamma-, and nitric oxide-dependent immunity," *J. Exp. Med.*, 183 (4): 1739-1746 (1996).
Einfeld et al., "Reducing the native tropism of adenovirus vectors requires removal of both CAR and integrin interactions,"*J. Virol.*, 75 (23): 11284-11291 (Dec. 2001).
Engers et al., "Malaria vaccine development: current status," *Parisitol. Today*, 14 (2): 56-64 (Feb. 1, 1998).
Epstein et al., "Safety, tolerability, and lack of antibody responses after administration of a *Pf*CSP DNA malaria vaccine via needle or needle-free jet injection, and comparison of intramuscular and combination intramuscular/intradermal routes," *Hum. Gene Ther.*, 13 (13): 1551-1560 (Sep. 2002).
European Patent Office, International Search Report in International Patent Application No. PCT/US2006/033982 (Oct. 8, 2007).
Gardner et al., "Genome sequence of the human malaria parasite *Plasmodium falciparum*," *Nature*, 419: 498-511 (2002).
Geibel et al., "Screening of cyclic peptide phage libraries identified ligands that bind streptavidin with high affinities," *Biochemistry*, 34: 15430-15435 (1995).
Gowda et al., "Protein glycosylation in the malaria parasite," *Parisitol. Today*, 15 (4): 147-152 (Apr. 1, 1999).
Graham et al., "Characteristics of a human cell line transformed by DNA from human adenovirus type 5," *J. Gen. Virol.*, 36, 59-72 (1977).
Graves et al., "Vaccines for preventing malaria," *Cochrane Database Syst. Rev.*, 1: CD000129 (2003).
Greenwood et al., "Malaria vaccine trials," *Chem. Immunol.*, 80: 366-395 (2002).
Hall et al., "A comprehensive survey of the *Plasmodium* life cycle by genomic, transcriptomic, and proteomic analyses," *Science*, 307 (5706): 82-86 (Jan. 7, 2005).
He et al., "Construction of adenoviral and retroviral vectors coexpressing the genes encoding the hepatitis B surface antigen and B7-1 protein," *Gene*, 175: 121-125 (1996).
Katz, "Binding to protein targets of peptidic leads discovered by phage display: Crystal structures of streptavidin-bound linear and cyclic peptide ligands containing the HPQ sequence," *Biochemistry*, 34: 15421-15429 (1995).
Krook et al., "Selection of peptides with affinity for single stranded DNA using a phage display library," *Biochem. Biophys., Res. Commun.*, 204 (2): 849-854 (Oct. 28, 1994).
Le et al., "Safety, tolerability and humoral immune responses after intramuscular administration of a malaria DNA vaccine to healthy adult volunteers," *Vaccine*, 18: 1893-1901 (2000).
Leung et al., "A method for random mutagenesis of a defined DNA segment using a modified polymerase chain reaction," *Technique*, 1: 11-15 (1989).
Marinovic et al., "Ubiquitin (*UbC*) expression in muscle cells is increased by glucocorticoids through a mechanism involving Sp 1 and MEK1," *J. Biol. Chem.*, 277 (19): 16673-16681 (May 10, 2002).
Moore et al., "Malaria vaccines: where are we and where are we going?" *Lancet Infect. Dis.*, 2 (12): 737-743 (2002).
Moorthy et al., "Malaria vaccines," *Br. Med. Bull.*, 62 (1): 59-72 (2002).
Pardoll, "Spinning molecular immunology into successful immunotherapy," *Nat. Rev. Immunol*, 2 (4): 227-238 (Apr. 2002).
Pasqualini et al., "A peptide isolated from phage display libraries is a structural and functional mimic of an RGD-binding site on integrins," *J. Cell. Biol.*, 130 (5): 1189-1196 (Sep. 1995).
Pritchard et al., "A general model of error-prone PCR," *J. Theoretical Biol.*, 234: 497-509 (2005).

(56) References Cited

OTHER PUBLICATIONS

Pützer et al., "Interleukin 12 and B7-1 costimulatory molecule expressed by an adenovirus vector act synergistically to facilitate tumor regression," *Proc. Natl. Acad. Sci. USA*, 94: 10889-10894 (Sep. 1997).

Ramasamy et al., "Interactions of human malaria parasites, *Plasmodium vivax* and *P.falciparum*, with the midgut of Anopheles mosquitoes," *Med. Vet. Entomol.*, 11 (3): 290-296 (1997).

Richie et al., "Progress and challenges for malaria vaccines," *Nature*, 415: 694-701 (Feb. 2002).

Roelvink et al., "Identification of a conserved receptor-binding site on the fiber proteins of CAR-recognizing adenoviridae," *Science*, 286: 1568-1571 (Nov. 19, 1999).

Rogers et al., "Multistage multiantigen heterologous prime boost vaccine for *Plasmodium knowlesi* malaria provides partial protection in rhesus macaques," *Infect. Immun.*, 69 (9): 5565-5572 (Sep. 2001).

Rogers et al., "Protection of rhesus macaques against lethal *Plasmodium knowlesi* malaria by a heterologous DNA priming and poxvirus boosting immunization regimen," *Infect. Immun.*, 70 (8): 4329-4335 (Aug. 2002).

Rux et al., "Structural and phylogenetic analysis of adenovirus hexons by use of high-resolution x-ray crystallographic, molecular modeling, and sequence-based methods," *J. Virol.*, 77 (17): 9553-9566 (Sep. 2003).

Saggio et al., "Biotin binders selected from a random peptide library expressed on phage," *Biochem. J.*, 293 (3): 613-616 (Aug. 1, 1993).

Schmidt-Dannert et al., "Molecular breeding of carotenoid biosynthetic pathways," *Nat. Biotechnol.*, 18 (7): 750-753 (Jul. 2000).

Sedegah et al., "Boosting with recombinant vaccinia increases immunogenicity and protective efficacy of malaria DNA vaccine," *Proc. Natl. Acad. Sci. USA*, 95 (13): 7648-7653 (Jun. 23, 1998).

Sedegah et al., "Protection against malaria by immunization with plasmid DNA encoding circumsporozoite protein," *Proc. Natl. Acad. Sci. USA*, 91 (21): 9866-9870 (Oct. 11, 1994).

Stemmer, "Rapid evolution of a protein in vitro by DNA shuffling," *Nature*, 370: 389-391 (Aug. 4, 1994).

Stowers et al., "A recombinant vaccine expressed in the milk of transgenic mice protects Aotus monkeys from a lethal challenge with *Plasmodium falciparum*," *Proc. Natl. Acad. Sci. USA*, 99 (1): 339-344 (Jan. 8, 2002).

Stowers et al., "Efficacy of two alternate vaccines based on *Plasmodium falciparum* merozoite surface protein 1 in an *Aotus* challenge trial," *Infect. Immun.*, 69 (3): 1536-1546 (Mar. 2001).

van Beusechem et al., "Efficient and selective gene transfer into primary human brain tumors by using single-chain antibody-targeted adenoviral vectors with native tropism abolished," *J. Virol.*, 76 (6): 2753-2762 (Mar. 2002).

Wagner et al., "Nucleotide sequence of the thymidine kinase gene of herpes simplex virus type 1," *Proc. Natl. Acad. Sci.*, 78(1): 1441-1445 (Mar. 1981).

Wang et al., "Induction of antigen-specific cytotoxic T lymphocytes in humans by a malaria DNA vaccine," *Science*, 282 (5388): 476-480 (Oct. 16, 1998).

Wang et al., "Simultaneous induction of multiple antigen-specific cytotoxic T lymphocytes in nonhuman primates by immunization with a mixture of four *Plasmodium falciparum* DNA plasmids," *Infect Immun.*, 66 (9): 4193-4202 (Sep. 1998).

Wen et al., "Tricistronic viral vectors co-expressing interleukin-12 (IL-12) and CD80 (B7-1) for the immunotherapy of cancer: Preclinical studies in myeloma," *Cancer Gene Ther.*, 8 (5): 361-370 (2001).

Wickham et al., "Adenovirus targeted to heparin-containing receptors increases its gene delivery efficiency to multiple cell types," *Nature Biotechnol.*, 14: 1570-1573 (Nov. 1996).

Wilson et al., "Immunomodulation to enhance gene therapy," *Nat. Med.*, 3 (9): 887-889 (Sep. 1995).

Worgall et al., "Innate immune mechanisms dominate elimination of adenoviral vectors following in vivo administration," *Human Gene Therapy*, 8: 37-44 (Jan. 1, 1997).

Yang et al., "Addition of the MSA1 signal and anchor sequences to the malaria merozoite surface antigen 1 C-terminal region enhances immunogenicity when expressed by recombinant vaccinia virus," *Vaccine*, 15 (12-13): 1303-1313 (Aug.-Sep. 1997).

Yang et al., "Glycosylation and proteolyticprocessing of 70 kDa C-terminal recombinant polypeptides of *Plasmodium falciparum* merozoite surface protein 1 expressed in mammaliancells," *Glycobiology*, 9 (12): 1347-1356 (Dec. 1999).

Zavala et al., "A striking property of recombinant poxviruses: efficient inducers of in vivo expansion of primed $CD8_+$T Cells," *Virology*, 280 (2): 155-159 (Feb. 2001).

Xiao-Song et al., "Construction of Adenoviral and Retroviral Vectors Coexpressing the Genes Encoding the Hepatitis B Surface Antigen and B7-1 Protein" *Gene: An International Journal on Genes and Genomes*, 175(1): 121-125 (Oct. 1996).

\* cited by examiner

```
                           SEQUENCE LISTING

<160> NUMBER OF SEQ ID NOS: 31

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Cys Arg Gly Asp Cys
1               5

<210> SEQ ID NO 2
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: "Xaa" may be any amino acid
<220> FEATURE:
<221> NAME/KEY: MISC_FEATURE
<222> LOCATION: (8)..(8)
<223> OTHER INFORMATION: "Xaa" may be any amino acid

<400> SEQUENCE: 2

Cys Xaa Cys Arg Gly Asp Cys Xaa Cys
1               5

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Cys Asp Cys Arg Gly Asp Cys Phe Cys
1               5

<210> SEQ ID NO 4
<211> LENGTH: 1071
<212> TYPE: DNA
<213> ORGANISM: Artificial
<220> FEATURE:
<223> OTHER INFORMATION: Synthetic

<400> SEQUENCE: 4
atgatgcgca agctggccat cctgtccgtg tcctccttcc tgttcgtgga ggccctgttc      60
caggagtacc agtgctacgg ctcctcctcc aacaccgcg tgctgaacga gctgaactac     120
gacaacgccg gcaccaacct gtacaacgag ctggagatga actactacgg caagcaggag     180
aactggtact ccctgaagaa gaactcccgc tccctgggga gaacgacga cggcaacaac     240 gaggacaacg agaagctgcg caagcccaag cacaagaagc tgaagcagcc cgccgacggc     300
aaccccgacc ccaacgccaa ccccaacgtg gaccccaacc caaccccaa cgtggacccc     360 aacgccaacc ccaacgtgga ccccaacgcc aaccccaacg ccaaccccaa cgccaacccc     420
aacgccaacc ccaacgccaa ccccaacgcc aaccccaacg ccaaccccaa cgccaacccc     480
aacgccaacc ccaacgccaa ccccaacgcc aaccccaacg ccaaccccaa cgccaacccc     540
```

```
aacgccaacc ccaacgccaa ccccaacgcc aaccccaacg ccaacccca cgtggacccc    600 aacgccaacc ccaacgccaa ccccaacaag aacaaccagg gcaacggcca gggccacaac    660
atgcccaacg accccaaccg caacgtggac gagaacgcca acgccaactc cgccgtgaag    720
aacaacaaca acgaggagcc ctccgacaag cacatcaagg agtacctgaa caagatccag    780
aactccctgt ccaccgagtg gtcccccctgc tccgtgacct gcggcaacgg catccaggtg    840
cgcatcaagc ccggctccgc caacaagccc aaggacgagc tggactacgc caacgacatc    900
gagaagaaga tctgcaagat ggagaagtgc tcctccgtgt tcaacgtggt gaactcctcc    960
atcggcctga tcatggtgct gtccttcctg ttcctgaacg aattcgatga tctgctgtgc   1020
cttctagttg ccagccatct gttgtttgcc cctcccccgt gccttcctta a           1071

<210> SEQ ID NO 5
<211> LENGTH: 356
<212> TYPE: PRT
<213> ORGANISM: Artificial
<220> FEATURE:
<223> OTHER INFORMATION: Synthetic

<400> SEQUENCE: 5

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Lys Asn Asn Gln Gly Asn Gly Gln Gly His Asn Met Pro Asn Asp
    210                 215                 220

Pro Asn Arg Asn Val Asp Glu Asn Ala Asn Ala Asn Ser Ala Val Lys
225                 230                 235                 240

Asn Asn Asn Asn Glu Glu Pro Ser Asp Lys His Ile Lys Glu Tyr Leu
                245                 250                 255

Asn Lys Ile Gln Asn Ser Leu Ser Thr Glu Trp Ser Pro Cys Ser Val
            260                 265                 270
```

```
Thr Cys Gly Asn Gly Ile Gln Val Arg Ile Lys Pro Gly Ser Ala Asn
            275                 280                 285

Lys Pro Lys Asp Glu Leu Asp Tyr Ala Asn Asp Ile Glu Lys Lys Ile
        290                 295                 300

Cys Lys Met Glu Lys Cys Ser Ser Val Phe Asn Val Val Asn Ser Ser
305                 310                 315                 320

Ile Gly Leu Ile Met Val Leu Ser Phe Leu Phe Leu Asn Glu Phe Asp
                    325                 330                 335

Asp Leu Leu Cys Leu Leu Val Ala Ser His Leu Leu Phe Ala Pro Pro
            340                 345                 350

Pro Cys Leu Pro
        355

<210> SEQ ID NO 6
<211> LENGTH: 999
<212> TYPE: DNA
<213> ORGANISM: Artificial
<220> FEATURE:
<223> OTHER INFORMATION: Synthetic

<400> SEQUENCE: 6
atgatgcgca agctggccat cctgtccgtg tcctccttcc tgttcgtgga ggccctgttc      60
caggagtacc agtgctacgg ctcctcctcc aacacccgcg tgctgaacga gctgaactac     120
gacaacgccg gcaccaacct gtacaacgag ctggagatga actactacgg caagcaggag     180
aactggtact ccctgaagaa gaactcccgc tccctgggcg agaacgacga cggcaacaac     240
gaggacaacg agaagctgcg caagcccaag cacaagaagc tgaagcagcc cgccgacggc     300
aaccccgacc ccaacgccaa ccccaacgtg gaccccaacg ccaaccccaa cgtggacccc     360
aacgccaacc ccaacgtgga ccccaacgcc aaccccaacg ccaaccccaa cgccaacccc     420
aacgccaacc ccaacgccaa ccccaacgcc aaccccaacg ccaaccccaa cgccaacccc     480
aacgccaacc ccaacgccaa ccccaacgcc aaccccaacg ccaaccccaa cgccaacccc     540
aacgccaacc ccaacgccaa ccccaacgcc aaccccaacg ccaaccccaa cgccaacccc     600
aacgccaacc ccaacgccaa ccccaacaag aacaaccagg gcaacggcca gggccacaac     660
atgcccaacg accccaaccg caacgtggac gagaacgcca acgccaactc cgccgtgaag     720
aacaacaaca acgaggagcc ctccgacaag cacatcaagg agtacctgaa caagatccag     780
aactccctgt ccaccgagtg gtcccccctgc tccgtgacct gcggcaacgg catccaggtg     840
cgcatcaagc ccggctccgc caacaagccc aaggacgagc tggactacgc caacgacatc     900
gagaagaaga tctgcaagat ggagaagtgc tcctccgtgt tcaacgtggt gaactcctcc     960
atcggcctga tcatggtgct gtccttcctg ttcctgaac                            999

<210> SEQ ID NO 7
<211> LENGTH: 333
<212> TYPE: PRT
<213> ORGANISM: Artificial
<220> FEATURE:
<223> OTHER INFORMATION: Synthetic

<400> SEQUENCE: 7

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30
```

```
Arg Val Leu Asn Glu Leu Asn Tyr Asp Asn Ala Gly Thr Asn Leu Tyr
             35                  40                  45
Asn Glu Leu Glu Met Asn Tyr Tyr Gly Lys Gln Glu Asn Trp Tyr Ser
 50                  55                  60
Leu Lys Lys Asn Ser Arg Ser Leu Gly Glu Asn Asp Asp Gly Asn Asn
 65                  70                  75                  80
Glu Asp Asn Glu Lys Leu Arg Lys Pro Lys His Lys Lys Leu Lys Gln
                 85                  90                  95
Pro Ala Asp Gly Asn Pro Asp Pro Asn Ala Asn Pro Asn Val Asp Pro
            100                 105                 110
Asn Ala Asn Pro Asn Val Asp Pro Asn Ala Asn Pro Asn Val Asp Pro
            115                 120                 125
Asn Ala Asn Pro Asn Ala Asn Pro Asn Ala Asn Pro Asn Ala Asn Pro
        130                 135                 140
Asn Ala Asn Pro Asn Ala Asn Pro Asn Ala Asn Pro Asn Ala Asn Pro
145                 150                 155                 160
Asn Ala Asn Pro Asn Ala Asn Pro Asn Ala Asn Pro Asn Ala Asn Pro
                165                 170                 175
Asn Ala Asn Pro Asn Ala Asn Pro Asn Ala Asn Pro Asn Ala Asn Pro
            180                 185                 190
Asn Ala Asn Pro Asn Val Asp Pro Asn Ala Asn Pro Asn Ala Asn Pro
            195                 200                 205
Asn Lys Asn Asn Gln Gly Asn Gly Gln Gly His Asn Met Pro Asn Asp
        210                 215                 220
Pro Asn Arg Asn Val Asp Glu Asn Ala Asn Ala Asn Ser Ala Val Lys
225                 230                 235                 240
Asn Asn Asn Asn Glu Glu Pro Ser Asp Lys His Ile Lys Glu Tyr Leu
                245                 250                 255
Asn Lys Ile Gln Asn Ser Leu Ser Thr Glu Trp Ser Pro Cys Ser Val
            260                 265                 270
Thr Cys Gly Asn Gly Ile Gln Val Arg Ile Lys Pro Gly Ser Ala Asn
            275                 280                 285
Lys Pro Lys Asp Glu Leu Asp Tyr Ala Asn Asp Ile Glu Lys Lys Ile
290                 295                 300
Cys Lys Met Glu Lys Cys Ser Ser Val Phe Asn Val Val Asn Ser Ser
305                 310                 315                 320
Ile Gly Leu Ile Met Val Leu Ser Phe Leu Phe Leu Asn
                325                 330

<210> SEQ ID NO 8
<211> LENGTH: 969
<212> TYPE: DNA
<213> ORGANISM: Artificial
<220> FEATURE:
<223> OTHER INFORMATION: Synthetic

<400> SEQUENCE: 8
atgatgcgca agctggccat cctgtccgtg tcctccttcc tgttcgtgga ggccctgttc      60
caggagtacc agtgctacgg ctcctcctcc aacacccgcg tgctgaacga gctgaactac     120
gacaacgccg gcaccaacct gtacaacgag ctggagatga actactacgg caagcaggag     180
aactggtact ccctgaagaa gaactcccgc tccctgggcg agaacgacga cggcaacaac     240
gaggacaacg agaagctgcg caagcccaag cacaagaagc tgaagcagcc cgccgacggc     300
aaccccgacc ccaacgccaa ccccaacgtg gaccccaacg ccaaccccaa cgtggacccc     360
```

-continued

```
aacgccaacc ccaacgtgga ccccaacgcc aaccccaacg ccaaccccaa cgccaacccc      420
aacgccaacc ccaacgccaa ccccaacgcc aaccccaacg ccaaccccaa cgccaacccc      480
aacgccaacc ccaacgccaa ccccaacgcc aaccccaacg ccaaccccaa cgccaacccc      540
aacgccaacc ccaacgccaa ccccaacgcc aaccccaacg ccaaccccaa cgtggacccc      600
aacgccaacc ccaacgccaa ccccaacaag aacaaccagg caacggcca gggccacaac      660 atgcccaacg accccaaccg caacgtggac gagaacgcca cgccaactc cgccgtgaag      720 aacaacaaca cgaggagcc ctccgacaag cacatcaagg agtacctgaa caagatccag      780
aactccctgt ccaccgagtg gtccccctgc tccgtgacct gcggcaacgg catccaggtg      840
cgcatcaagc ccggctccgc caacaagccc aaggacgagc tggactacgc caacgacatc      900
gagaagaaga tctgcaagat ggagaagtgc tcctccgtgt tcaacgtggt gaactcctcc      960
atcggctaa                                                              969
```

<210> SEQ ID NO 9
<211> LENGTH: 322
<212> TYPE: PRT
<213> ORGANISM: Artificial
<220> FEATURE:
<223> OTHER INFORMATION: Synthetic

<400> SEQUENCE: 9

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Lys Asn Asn Gln Gly Asn Gly Gln Gly His Asn Met Pro Asn Asp
    210                 215                 220

Pro Asn Arg Asn Val Asp Glu Asn Ala Asn Ala Asn Ser Ala Val Lys
225                 230                 235                 240

Asn Asn Asn Asn Glu Glu Pro Ser Asp Lys His Ile Lys Glu Tyr Leu
                245                 250                 255
```

```
Asn Lys Ile Gln Asn Ser Leu Ser Thr Glu Trp Ser Pro Cys Ser Val
            260                 265                 270

Thr Cys Gly Asn Gly Ile Gln Val Arg Ile Lys Pro Gly Ser Ala Asn
        275                 280                 285

Lys Pro Lys Asp Glu Leu Asp Tyr Ala Asn Asp Ile Glu Lys Lys Ile
    290                 295                 300

Cys Lys Met Glu Lys Cys Ser Ser Val Phe Asn Val Asn Ser Ser
305                 310                 315                 320

Ile Gly

<210> SEQ ID NO 10
<211> LENGTH: 1869
<212> TYPE: DNA
<213> ORGANISM: Artificial
<220> FEATURE:
<223> OTHER INFORMATION: Synthetic

<400> SEQUENCE: 10
atgcgcaagc tgtactgcgt gctgctgctg tccgccttcg agttcaccta catgatcaac      60
ttcggccgcg gccagaacta ctgggagcac ccctaccaga actccgacgt gtaccgcccc     120
atcaacgagc accgcgagca ccccaaggag tacgagtacc cctgcaccag ggagcacacc     180
taccagcagg aggactccgg cgaggacgag aacaccctgc agcacgccta ccccatcgac     240
cacgagggcg ccgagcccgc cccccaggag cagaacctgt ctcctccat cgagatcgtg     300 gagcgctcca actacatggg caaccccctgg accgagtaca tggccaagta cgacatcgag     360
gaggtgcacg gctccggcat ccgcgtggac ctgggcgagg acgccgaggt ggccggcacc     420
cagtaccgcc tgccctccgg caagtgcccc gtgttcggca agggcatcat catcgagaac     480
tccaacacca ccttcctgac ccccgtggcc accggcaacc agtacctgaa ggacggcggc     540
ttcgccttcc cccccaccga gcccctgatg tccccatga ccctggacga gatgcgccac     600
ttctacaagg acaacaagta cgtgaagaac ctggacgagc tgaccctgtg ctcccgccac     660
gccggcaaca tgatccccga caacgacaag aactccaact acaagtaccc cgccgtgtac     720
gacgacaagg acaagaagtg ccacatcctg tacatcgccg cccaggagaa caacggcccc     780
cgctactgca caaggacga gtccaagcgc aactccatgt ctgcttccg ccccgccaag     840 gacatctcct tccagaacta cacctacctg tccaagaacg tggtggacaa ctgggagaag     900
gtgtgccccc gcaagaacct gcagaacgcc aagttcggcc tgtgggtgga cggcaactgc     960
gaggacatcc ccacgtgaa cgagttcccc gccatcgacc tgttcgagtg caacaagctg    1020
gtgttcgagc tgtccgcctc cgaccagccc aagcagtacg agcagcacct gaccgactac    1080
gagaagatca ggagggcttc aagaacaag acgcctcca tgatcaagtc cgccttcctg    1140
cccaccggcg ccttcaaggc cgaccgctac aagtcccacg caagggcta caactggggc    1200 aactacaaca ccgagaccca gaagtgcgag atcttcaacg tgaagcccac ctgcctgatc    1260
aacaactcct cctacatcgc caccaccgcc ctgtcccacc catcgaggt ggagaacaac    1320 ttcccctgct ccctgtacaa ggacgagatc atgaaggaga tcgagcgcga gtccaagcgc    1380
atcaagctga cgacaacga cgacgagggc aacaagaaga tcatcgcccc ccgcatcttc    1440
atctccgacg acaaggactc cctgaagtgc ccctgcgacc ccgagatggt gtccaactcc    1500
acctgccgct tcttcgtgtg caagtgcgtg gagcgccgcg ccgaggtgac ctccaacaac    1560
gaggtggtgg tgaaggagga gtacaaggac gagtacgccg acatccccga gcacaagccc    1620
```

-continued

```
acctacgaca agatgaagat catcatcgcc tcctccgccg ccgtggccgt gctggccacc    1680
atcctgatgg tgtacctgta caagcgcaag ggcaacgccg agaagtacga caagatggac    1740
gagccccagg actacggcaa gtccaactcc cgcaacgacg agatgctgga ccccgaggcc    1800
tccttctggg gcgaggagaa gcgcgcctcc cacaccaccc ccgtgctgat ggagaagccc    1860
tactactaa                                                            1869
```

<210> SEQ ID NO 11
<211> LENGTH: 622
<212> TYPE: PRT
<213> ORGANISM: Artificial
<220> FEATURE:
<223> OTHER INFORMATION: Synthetic

<400> SEQUENCE: 11

```
Met Arg Lys Leu Tyr Cys Val Leu Leu Leu Ser Ala Phe Glu Phe Thr
 1               5                  10                  15

Tyr Met Ile Asn Phe Gly Arg Gly Gln Asn Tyr Trp Glu His Pro Tyr
                20                  25                  30

Gln Asn Ser Asp Val Tyr Arg Pro Ile Asn Glu His Arg Glu His Pro
            35                  40                  45

Lys Glu Tyr Glu Tyr Pro Leu His Gln Glu His Thr Tyr Gln Gln Glu
        50                  55                  60

Asp Ser Gly Glu Asp Glu Asn Thr Leu Gln His Ala Tyr Pro Ile Asp
 65                  70                  75                  80

His Glu Gly Ala Glu Pro Ala Pro Gln Glu Gln Asn Leu Phe Ser Ser
                85                  90                  95

Ile Glu Ile Val Glu Arg Ser Asn Tyr Met Gly Asn Pro Trp Thr Glu
                100                 105                 110

Tyr Met Ala Lys Tyr Asp Ile Glu Glu Val His Gly Ser Gly Ile Arg
            115                 120                 125

Val Asp Leu Gly Glu Asp Ala Glu Val Ala Gly Thr Gln Tyr Arg Leu
        130                 135                 140

Pro Ser Gly Lys Cys Pro Val Phe Gly Lys Gly Ile Ile Glu Asn
145                 150                 155                 160

Ser Asn Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
        195                 200                 205

Lys Asn Leu Asp Glu Leu Thr Leu Cys Ser Arg His Ala Gly Asn Met
    210                 215                 220

Ile Pro Asp Asn Asp Lys Asn Ser Asn Tyr Lys Tyr Pro Ala Val Tyr
225                 230                 235                 240

Asp Asp Lys Asp Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Asn Tyr Thr
        275                 280                 285

Tyr Leu Ser Lys Asn Val Val Asp Asn Trp Glu Lys Val Cys Pro Arg
    290                 295                 300

Lys Asn Leu Gln Asn Ala Lys Phe Gly Leu Trp Val Asp Gly Asn Cys
305                 310                 315                 320
```

Glu Asp Ile Pro His Val Asn Glu Phe Pro Ala Ile Asp Leu Phe Glu
            325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys
            355                 360                 365

Asn Lys Asn Ala Ser Met Ile Lys Ser Ala Phe Leu Pro Thr Gly Ala
            370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415

Thr Cys Leu Ile Asn Asn Ser Ser Tyr Ile Ala Thr Thr Ala Leu Ser
                420                 425                 430

His Pro Ile Glu Val Glu Asn Asn Phe Pro Cys Ser Leu Tyr Lys Asp
                435                 440                 445

Glu Ile Met Lys Glu Ile Glu Arg Glu Ser Lys Arg Ile Lys Leu Asn
            450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495

Val Ser Asn Ser Thr Cys Arg Phe Phe Val Cys Lys Cys Val Glu Arg
                500                 505                 510

Arg Ala Glu Val Thr Ser Asn Glu Val Val Lys Glu Glu Tyr
                515                 520                 525

Lys Asp Glu Tyr Ala Asp Ile Pro Glu His Lys Pro Thr Tyr Asp Lys
            530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Asp Tyr Gly Lys Ser Asn Ser Arg Asn
            580                 585                 590

Asp Glu Met Leu Asp Pro Glu Ala Ser Phe Trp Gly Glu Lys Arg
            595                 600                 605

Ala Ser His Thr Thr Pro Val Leu Met Glu Lys Pro Tyr Tyr
610                 615                 620

<210> SEQ ID NO 12
<211> LENGTH: 1869
<212> TYPE: DNA
<213> ORGANISM: Artificial
<220> FEATURE:
<223> OTHER INFORMATION: Synthetic

<400> SEQUENCE: 12
atgcgcaagc tgtactgcgt gctgctgctg tccgccttcg agttcaccta catgatcaac      60
ttcggccgcg gccagaacta ctgggagcac ccctaccaga actccgacgt gtaccgcccc     120
atcaacgagc accgcgagca ccccaaggag tacgagtacc cctgcaccag gagcacacc      180 taccagcagg aggactccgg cgaggacgag aacaccctgc agcacgccta ccccatcgac     240
cacgagggcg ccgagcccgc ccccaaggag cagaacctgt tctcctccat cgagatcgtg     300
gagcgctcca actacatggg caaccccctgg accgagtaca tggccaagta cgacatcgag     360

-continued

```
gaggtgcacg gctccggcat ccgcgtggac ctgggcgagg acgccgaggt ggccggcacc    420
cagtaccgcc tgccctccgg caagtgcccc gtgttcggca agggcatcat catcgagaac    480
tccaagacaa cgttcctgac ccccgtggcc accggcaacc agtacctgaa ggacggcggc    540
ttcgccttcc cccccaccga gcccctgatg tcccccatga ccctggacga gatgcgccac    600
ttctacaagg acaacaagta cgtgaagaac ctggacgagc tgaccctgtg ctcccgccac    660
gccggcaaca tgatccccga caacgacaag aactccaact acaagtaccc cgccgtgtac    720
gacgacaagg acaagaagtg ccacatcctg tacatcgccg cccaggagaa caacggcccc    780
cgctactgca acaaggacga gtccaagcgc aactccatgt tctgcttccg ccccgccaag    840
gacatctcct tccagcagta tacgtacctg tccaagaacg tggtggacaa ctgggagaag    900
gtgtgccccc gcaagaacct gcagaacgcc aagttcggcc tgtgggtgga cggcaactgc    960
gaggacatcc cccacgtgaa cgagttcccc gccatcgacc tgttcgagtg caacaagctg   1020
gtgttcgagc tgtccgcctc cgaccagccc aagcagtacg agcagcacct gaccgactac   1080
gagaagatca aggagggctt caagaacaag caggcctcca tgatcaagtc cgccttcctg   1140
cccaccggcg ccttcaaggc cgaccgctac aagtcccacg gcaagggcta caactggggc   1200
aactacaaca ccgagaccca gaagtgcgag atcttcaacg tgaagcccac ctgcctgatc   1260
cagcagagct cctacatcgc caccaccgcc ctgtcccacc ccatcgaggt ggagaacaac   1320
ttcccctgct ccctgtacaa ggacgagatc atgaaggaga tcgagcgcga gtccaagcgc   1380
atcaagctga acgacaacga cgacgagggc aacaagaaga tcatcgcccc ccgcatcttc   1440
atctccgacg acaaggactc cctgaagtgc ccctgcgacc ccgagatggt gtcccagtcc   1500
acgtgccgct tcttcgtgtg caagtgcgtg gagcgccgcg ccgaggtgac ctccaacaac   1560
gaggtggtgg tgaaggagga gtacaaggac gagtacgccg acatccccga gcacaagccc   1620
acctacgaca agatgaagat catcatcgcc tcctccgccg ccgtggccgt gctggccacc   1680
atcctgatgg tgtacctgta caagcgcaag ggcaacgccg agaagtacga caagatggac   1740
gagccccagg actacggcaa gtccaactcc cgcaacgacg agatgctgga ccccgaggcc   1800
tccttctggg gcgaggagaa gcgcgcctcc cacaccaccc ccgtgctgat ggagaagccc   1860
tactactaa                                                           1869
```

```
<210> SEQ ID NO 13
<211> LENGTH: 622
<212> TYPE: PRT
<213> ORGANISM: Artificial
<220> FEATURE:
<223> OTHER INFORMATION: Synthetic

<400> SEQUENCE: 13

Met Arg Lys Leu Tyr Cys Val Leu Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
        35                  40                  45

Lys Glu Tyr Glu Tyr Pro Leu His Gln Glu His Thr Tyr Gln Gln Glu
    50                  55                  60

Asp Ser Gly Glu Asp Glu Asn Thr Leu Gln His Ala Tyr Pro Ile Asp
65                  70                  75                  80

His Glu Gly Ala Glu Pro Ala Pro Gln Glu Gln Asn Leu Phe Ser Ser
```

```
                85                  90                  95
Ile Glu Ile Val Glu Arg Ser Asn Tyr Met Gly Asn Pro Trp Thr Glu
            100                 105                 110

Tyr Met Ala Lys Tyr Asp Ile Glu Glu Val His Gly Ser Gly Ile Arg
            115                 120                 125

Val Asp Leu Gly Glu Asp Ala Glu Val Ala Gly Thr Gln Tyr Arg Leu
            130                 135                 140

Pro Ser Gly Lys Cys Pro Val Phe Gly Lys Gly Ile Ile Ile Glu Asn
145                 150                 155                 160

Ser Lys Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
            195                 200                 205

Lys Asn Leu Asp Glu Leu Thr Leu Cys Ser Arg His Ala Gly Asn Met
210                 215                 220

Ile Pro Asp Asn Asp Lys Asn Ser Asn Tyr Lys Tyr Pro Ala Val Tyr
225                 230                 235                 240

Asp Asp Lys Asp Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Gln Tyr Thr
            275                 280                 285

Tyr Leu Ser Lys Asn Val Val Asp Asn Trp Glu Lys Val Cys Pro Arg
            290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys
            355                 360                 365

Asn Lys Gln Ala Ser Met Ile Lys Ser Ala Phe Leu Pro Thr Gly Ala
            370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415

Thr Cys Leu Ile Gln Gln Ser Ser Tyr Ile Ala Thr Thr Ala Leu Ser
            420                 425                 430

His Pro Ile Glu Val Glu Asn Asn Phe Pro Cys Ser Leu Tyr Lys Asp
            435                 440                 445

Glu Ile Met Lys Glu Ile Glu Arg Glu Ser Lys Arg Ile Lys Leu Asn
            450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495

Val Ser Gln Ser Thr Cys Arg Phe Phe Val Cys Lys Cys Val Glu Arg
            500                 505                 510
```

```
Arg Ala Glu Val Thr Ser Asn Asn Glu Val Val Lys Glu Glu Tyr
        515                 520                 525

Lys Asp Glu Tyr Ala Asp Ile Pro Glu His Lys Pro Thr Tyr Asp Lys
530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Asp Tyr Gly Lys Ser Asn Ser Arg Asn
            580                 585                 590

Asp Glu Met Leu Asp Pro Glu Ala Ser Phe Trp Gly Glu Lys Arg
        595                 600                 605

Ala Ser His Thr Thr Pro Val Leu Met Glu Lys Pro Tyr Tyr
    610                 615                 620
```

<210> SEQ ID NO 14
<211> LENGTH: 1803
<212> TYPE: DNA
<213> ORGANISM: Artificial
<220> FEATURE:
<223> OTHER INFORMATION: Synthetic

<400> SEQUENCE: 14

```
atgggccaga actactggga gcaccsctac cagaactccg acgtgtaccg ccccatcaac    60
gagcaccgcg agcaccccaa ggagtacgag taccccctgc caccaggagca cacctaccag   120
caggaggact ccggcgagga cgagaacacc ctgcagcacg cctaccccat cgaccacgag   180
ggcgccgagc ccgcccccca ggagcagaac ctgttctcct ccatcgagat cgtggagcgc   240
tccaactaca tgggcaaccc ctggaccgag tacatggcca gtacgacat cgaggaggtg   300
cacggctccg gcatccgcgt ggacctgggc gaggacgccg aggtggccgg caccagtac   360
cgcctgccct ccggcaagtg cccgtgttc ggcaagggca tcatcatcga gaactccaac   420
accaccttcc tgaccccgt ggccaccggc aaccagtacc tgaaggacgg cggcttcgcc   480
ttccccccca ctgagcccct gatgtccccc atgaccctgg acgagatgcg ccacttctac   540
aaggacaaca agtacgtgaa gaacctggac gagctgaccc tgtgctcccg ccacgccggc   600
aacatgatcc ccgacaacga caagaactcc aactacaagt accccgccgt gtacgacgac   660
aaggacaaga agtgccacat cctgtacatc gccgcccagg agaacaacgg ccccgctac   720
tgcaacaagg acgagtccaa cgcaactcc atgttctgct ccgccccgc caaggacatc   780
tccttccaga actacacct cctgtccaag aacgtggtgg acaactggga aaggtgtgc   840
ccccgcaaga acctgcagaa cgccaagttc ggcctgtggg tggacggcaa ctgcgaggac   900
atcccccacg tgaacgagtt ccccgccatc gacctgttcg agtgcaacaa gctggtgttc   960
gagctgtccg cctccgacca gcccaagcag tacgagcagc acctgaccga ctacgagaag  1020
atcaaggagg gcttcaagaa caagaacgcc tccatgatca gtccgccctt cctgccccac  1080
ggcgccttca ggccgaccg ctacaagtcc cacggcaagg gctacaactg ggcaactac  1140
aacaccgaga cccagaagtg cgagatcttc aacgtgaagc ccacctgcct gatcaacaac  1200
tcctcctaca tcgccaccac cgccctgtcc caccccatcg aggtggagaa caacttcccc  1260
tgctccctgt acaaggacga gatcatgaag gagatcgagc gcgagtccaa gcgcatcaag  1320
ctgaacgaca cgacgacga gggcaacaag aagatcatcg ccccccgcat cttcatctcc  1380
gacgacaagg actccctgaa gtgccccctgc gaccccgaga tggtgtccaa ctccacctgc  1440
```

```
cgcttcttcg tgtgcaagtg cgtggagcgc cgcgccgagg tgacctccaa caacgaggtg    1500
gtggtgaagg aggagtacaa ggacgagtac gccgacatcc ccgagcacaa gcccacctac    1560
gacaagatga agatcatcat cgcctcctcc gccgccgtgg ccgtgctggc caccatcctg    1620
atggtgtacc tgtacaagcg caagggcaac gccgagaagt acgacaagat ggacgagccc    1680
caggactacg gcaagtccaa ctcccgcaac gacgagatgc tggaccccga ggcctccttc    1740
tggggcgagg agaagcgcgc ctcccacacc accccgtgc tgatggagaa gccctactac    1800
taa                                                                  1803
```

```
<210> SEQ ID NO 15
<211> LENGTH: 600
<212> TYPE: PRT
<213> ORGANISM: Artificial
<220> FEATURE:
<223> OTHER INFORMATION: Synthetic

<400> SEQUENCE: 15

Met Gly Gln Asn Tyr Trp Glu His Pro Tyr Gln Asn Ser Asp Val Tyr
1               5                   10                  15

Arg Pro Ile Asn Glu His Arg Glu His Pro Lys Glu Tyr Glu Tyr Pro
            20                  25                  30

Leu His Gln Glu His Thr Tyr Gln Gln Glu Asp Ser Gly Glu Asp Glu
        35                  40                  45

Asn Thr Leu Gln His Ala Tyr Pro Ile Asp His Glu Gly Ala Glu Pro
    50                  55                  60

Ala Pro Gln Glu Gln Asn Leu Phe Ser Ser Glu Ile Val Glu Arg
65                  70                  75                  80

Ser Asn Tyr Met Gly Asn Pro Trp Thr Glu Tyr Met Ala Lys Tyr Asp
                85                  90                  95

Ile Glu Glu Val His Gly Ser Gly Ile Arg Val Asp Leu Gly Glu Asp
            100                 105                 110

Ala Glu Val Ala Gly Thr Gln Tyr Arg Leu Pro Ser Gly Lys Cys Pro
        115                 120                 125

Val Phe Gly Lys Gly Ile Ile Glu Asn Ser Asn Thr Thr Phe Leu
    130                 135                 140

Thr Pro Val Ala Thr Gly Asn Gln Tyr Leu Lys Asp Gly Gly Phe Ala
145                 150                 155                 160

Phe Pro Pro Thr Glu Pro Leu Met Ser Pro Met Thr Leu Asp Glu Met
                165                 170                 175

Arg His Phe Tyr Lys Asp Asn Lys Tyr Val Lys Asn Leu Asp Glu Leu
            180                 185                 190

Thr Leu Cys Ser Arg His Ala Gly Asn Met Ile Pro Asp Asn Asp Lys
        195                 200                 205

Asn Ser Asn Tyr Lys Tyr Pro Ala Val Tyr Asp Asp Lys Asp Lys Lys
    210                 215                 220

Cys His Ile Leu Tyr Ile Ala Ala Gln Glu Asn Asn Gly Pro Arg Tyr
225                 230                 235                 240

Cys Asn Lys Asp Glu Ser Lys Arg Asn Ser Met Phe Cys Phe Arg Pro
                245                 250                 255

Ala Lys Asp Ile Ser Phe Gln Asn Tyr Thr Tyr Leu Ser Lys Asn Val
            260                 265                 270

Val Asp Asn Trp Glu Lys Val Cys Pro Arg Lys Asn Leu Gln Asn Ala
        275                 280                 285
```

```
Lys Phe Gly Leu Trp Val Asp Gly Asn Cys Glu Asp Ile Pro His Val
    290                 295                 300
Asn Glu Phe Pro Ala Ile Asp Leu Phe Glu Cys Asn Lys Leu Val Phe
305                 310                 315                 320
Glu Leu Ser Ala Ser Asp Gln Pro Lys Gln Tyr Glu Gln His Leu Thr
                325                 330                 335
Asp Tyr Glu Lys Ile Lys Glu Gly Phe Lys Asn Lys Asn Ala Ser Met
            340                 345                 350
Ile Lys Ser Ala Phe Leu Pro Thr Gly Ala Phe Lys Ala Asp Arg Tyr
        355                 360                 365
Lys Ser His Gly Lys Gly Tyr Asn Trp Gly Asn Tyr Asn Thr Glu Thr
    370                 375                 380
Gln Lys Cys Glu Ile Phe Asn Val Lys Pro Thr Cys Leu Ile Asn Asn
385                 390                 395                 400
Ser Ser Tyr Ile Ala Thr Thr Ala Leu Ser His Pro Ile Glu Val Glu
                405                 410                 415
Asn Asn Phe Pro Cys Ser Leu Tyr Lys Asp Glu Ile Met Lys Glu Ile
            420                 425                 430
Glu Arg Glu Ser Lys Arg Ile Lys Leu Asn Asp Asn Asp Asp Glu Gly
        435                 440                 445
Asn Lys Lys Ile Ile Ala Pro Arg Ile Phe Ile Ser Asp Asp Lys Asp
    450                 455                 460
Ser Leu Lys Cys Pro Cys Asp Pro Glu Met Val Ser Asn Ser Thr Cys
465                 470                 475                 480
Arg Phe Phe Val Cys Lys Cys Val Glu Arg Arg Ala Glu Val Thr Ser
                485                 490                 495
Asn Asn Glu Val Val Val Lys Glu Glu Tyr Lys Asp Glu Tyr Ala Asp
            500                 505                 510
Ile Pro Glu His Lys Pro Thr Tyr Asp Lys Met Lys Ile Ile Ile Ala
        515                 520                 525
Ser Ser Ala Ala Val Ala Val Leu Ala Thr Ile Leu Met Val Tyr Leu
    530                 535                 540
Tyr Lys Arg Lys Gly Asn Ala Glu Lys Tyr Asp Lys Met Asp Glu Pro
545                 550                 555                 560
Gln Asp Tyr Gly Lys Ser Asn Ser Arg Asn Asp Glu Met Leu Asp Pro
                565                 570                 575
Glu Ala Ser Phe Trp Gly Glu Glu Lys Arg Ala Ser His Thr Thr Pro
            580                 585                 590
Val Leu Met Glu Lys Pro Tyr Tyr
        595                 600

<210> SEQ ID NO 16
<211> LENGTH: 1866
<212> TYPE: DNA
<213> ORGANISM: Artificial
<220> FEATURE:
<223> OTHER INFORMATION: Synthetic

<400> SEQUENCE: 16
atgcgcaagc tgtactgcgt gctgctgctg tccgccttcg agttcaccta catgatcaac        60
ttcggccgcg gccagaacta ctgggagcac ccctaccaga actccgacgt gtaccgcccc       120
atcaacgagc accgcgagca cccccaaggag tacgagtacc ccctgcacca ggagcacacc      180
taccagcagg aggactccgg cgaggacgag aacccctgc agcacgccta ccccatcgac        240
cacgagggcg ccgagcccgc cccccaggag cagaacctgt ctcctccat cgagatcgtg        300
```

```
gagcgctcca actacatggg caacccctgg accgagtaca tggccaagta cgacatcgag    360
gaggtgcacg gctccggcat ccgcgtggac ctgggcgagg acgccgaggt ggccggcacc    420
cagtaccgcc tgccctccgg caagtgcccc gtgttcggca agggcatcat catcgagaac    480
tccaagacaa cgttcctgac ccccgtggcc accggcaacc agtacctgaa ggacggcggc    540
ttcgccttcc ccccaccgga gccctgatg tcccccatga cctggacga gatgcgccac     600 ttctacaagg acaacaagta cgtgaagaac ctggacgagc tgaccctgtg ctcccgccac    660
gccggcaaca tgatccccga acgacaag aactccaact acaagtaccc cgccgtgtac      720
gacgacaagg acaagaagtg ccacatcctg tacatcgccg cccaggagaa caacggcccc    780
cgctactgca acaaggacga gtccaagcgc aactccatgt ctgcttccg ccccgccaag     840 gacatctcct tccagaacct ggtctacctg tccaagaacg tggtggacaa ctgggagaag    900 gtgtgcccc gcaagaacct gcagaacgcc aagttcggcc tgtgggtgga cggcaactgc    960
gaggacatcc cccacgtgaa cgagttcccc gccatcgacc tgttcgagtg caacaagctg    1020
gtgttcgagc tgtccgcctc cgaccagccc aagcagtacg agcagcacct gaccgactac   1080
gagaagatca ggagggctt caagaacaag aaccgggaga tgatcaagtc cgccttcctg    1140
cccaccggcg ccttcaaggc cgaccgctac aagtcccacg gcaagggcta caactggggc    1200
aactacaaca ccgagaccca gaagtgcgag atcttcaacg tgaagcccac ctgcctgatc    1260
aacgacaaga actacatcgc caccaccgcc ctgtcccacc ccatcgaggt ggagaacaac    1320
ttcccctgct ccctgtacaa ggacgagatc atgaaggaga tcgagcgcga gtccaagcgc   1380
atcaagctga cgacaacga cgacgagggc aacaagaaga tcatcgcccc ccgcatcttc    1440
atctccgacg acaaggactc cctgaagtgc ccctgcgacc ccgagatggt gtcccagtcc    1500
acgtgccgct tcttcgtgtg caagtgcgtg gagcgccgcg ccgaggtgac ctccaacaac   1560
gaggtggtgg tgaaggagga gtacaaggac gagtacgccg acatcccga gcacaagccc    1620 acctacgaca agatgaagat catcatcgcc tcctccgccg ccgtggccgt gctggccacc    1680
atcctgatgg tgtacctgta caagcgcaag ggcaacgccg agaagtacga caagatggac    1740
gagccccagg actacggcaa gtccaactcc cgcaacgacg agatgctgga ccccgaggcc    1800
tccttctggg gcgaggagaa cgcgcctcc cacaccaccc ccgtgctgat ggagaagccc    1860
tactac                                                              1866
```

<210> SEQ ID NO 17
<211> LENGTH: 622
<212> TYPE: PRT
<213> ORGANISM: Artificial
<220> FEATURE:
<223> OTHER INFORMATION: Synthetic

<400> SEQUENCE: 17

```
Met Arg Lys Leu Tyr Cys Val Leu Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
        35                  40                  45

Lys Glu Tyr Glu Tyr Pro Leu His Gln Glu His Thr Tyr Gln Gln Glu
    50                  55                  60

Asp Ser Gly Glu Asp Glu Asn Thr Leu Gln His Ala Tyr Pro Ile Asp
65                  70                  75                  80
```

```
His Glu Gly Ala Glu Pro Ala Pro Gln Glu Gln Asn Leu Phe Ser Ser
                85                  90                  95

Ile Glu Ile Val Glu Arg Ser Asn Tyr Met Gly Asn Pro Trp Thr Glu
                100                 105                 110

Tyr Met Ala Lys Tyr Asp Ile Glu Glu Val His Gly Ser Gly Ile Arg
                115                 120                 125

Val Asp Leu Gly Glu Asp Ala Glu Val Ala Gly Thr Gln Tyr Arg Leu
130                 135                 140

Pro Ser Gly Lys Cys Pro Val Phe Gly Lys Gly Ile Ile Ile Glu Asn
145                 150                 155                 160

Ser Lys Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
                180                 185                 190

Met Thr Leu Asp Glu Met Arg His Phe Tyr Lys Asp Asn Lys Tyr Val
                195                 200                 205

Lys Asn Leu Asp Glu Leu Thr Leu Cys Ser Arg His Ala Gly Asn Met
                210                 215                 220

Ile Pro Asp Asn Asp Lys Asn Ser Asn Tyr Lys Tyr Pro Ala Val Tyr
225                 230                 235                 240

Asp Asp Lys Asp Lys Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
                260                 265                 270

Met Phe Cys Phe Arg Pro Ala Lys Asp Ile Ser Phe Gln Asn Leu Val
                275                 280                 285

Tyr Leu Ser Lys Asn Val Val Asp Asn Trp Glu Lys Val Cys Pro Arg
                290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
                340                 345                 350

Tyr Glu Gln His Leu Thr Asp Tyr Glu Lys Ile Lys Glu Gly Phe Lys
                355                 360                 365

Asn Lys Asn Arg Glu Met Ile Lys Ser Ala Phe Leu Pro Thr Gly Ala
370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415

Thr Cys Leu Ile Asn Asp Lys Asn Tyr Ile Ala Thr Thr Ala Leu Ser
                420                 425                 430

His Pro Ile Glu Val Glu Asn Asn Phe Pro Cys Ser Leu Tyr Lys Asp
                435                 440                 445

Glu Ile Met Lys Glu Ile Glu Arg Glu Ser Lys Arg Ile Lys Leu Asn
                450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495
```

Val Ser Gln Ser Thr Cys Arg Phe Phe Val Cys Lys Cys Val Glu Arg
            500                 505                 510

Arg Ala Glu Val Thr Ser Asn Asn Glu Val Val Lys Glu Tyr
        515                 520                 525

Lys Asp Glu Tyr Ala Asp Ile Pro Glu His Lys Pro Thr Tyr Asp Lys
    530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Asp Tyr Gly Lys Ser Asn Ser Arg Asn
        580                 585                 590

Asp Glu Met Leu Asp Pro Glu Ala Ser Phe Trp Gly Glu Lys Arg
    595                 600                 605

Ala Ser His Thr Thr Pro Val Leu Met Glu Lys Pro Tyr Tyr
610                 615                 620

<210> SEQ ID NO 18
<211> LENGTH: 1194
<212> TYPE: DNA
<213> ORGANISM: Artificial
<220> FEATURE:
<223> OTHER INFORMATION: Synthetic

<400> SEQUENCE: 18

```
atgggcgagg ccatctccgt gaccatggac aacatcctgt ccggcttcga gaacgagtac      60
gacgtgatct acctgaagcc cctggccggc gtgtaccgct ccctgaagaa gcagatcgag     120
aagaacatct tcaccttcaa cctgaacctg aacgacatcc tgaactcccg cctgaagaag     180
cgcaagtact tcctggacgt gctggagtcc gacctgatgc agttcaagca catctcctcc     240
aacgagtaca tcatcgagga ctccttcaag ctgctgaact ccgagcagaa gaacaccctg     300
ctgaagtcct acaagtacat caaggagtcc gtggagaacg acatcaagtt cgcccaggag     360
ggcatctcct actacgagaa ggtgctggcc aagtacaagg acgacctgga gtccatcaag     420
aaggtgatca aggaggagaa ggagaagttc ccctcctccc ccccaccac ccccccctcc     480
cccgccaaga ccgacgagca agaaggag tccaagttcc tgcccttcct gaccaacatc     540
gagaccctgt acaacaacct ggtgaacaag atcgacgact acctgatcaa cctgaaggcc     600
aagatcaacg actgcaacgt ggagaaggac gaggcccacg tgaagatcac caagctgtcc     660
gacctgaagg ccatcgacga caagatcgac ctgttcaaga ccccctacga cttcgaggcc     720
atcaagaagc tgatcaacga cgacaccaag aaggacatgc tgggcaagct gctgtccacc     780
ggcctggtgc agaacttccc caacaccatc atctccaagc tgatcgaggg caagttccag     840
gacatgctga acatctccca gcaccagtgc gtgaagaagc agtgccccga gaactccggc     900
tgcttccgcc acctgacga gcgcgaggag tgcaagtgcc tgctgaacta caagcaggag     960
ggcgacaagt gcgtggagaa ccccaacccc acctgcaacg agaacaacgg cggctgcgac    1020
gccgacgcca cctgcaccga ggaggactcc ggctcctccc gcaagaagat caccctgcgag    1080
tgcaccaagc ccgactccta ccccctgttc gacggcatct ctgctcctc ctccaacttc    1140
ctgggcatct ccttcctgct gatcctgatg ctgatcctgt actccttcat ctaa          1194
```

<210> SEQ ID NO 19
<211> LENGTH: 397
<212> TYPE: PRT
<213> ORGANISM: Artificial

<220> FEATURE:
<223> OTHER INFORMATION: Synthetic

<400> SEQUENCE: 19

Met Gly Glu Ala Ile Ser Val Thr Met Asp Asn Ile Leu Ser Gly Phe
1               5                   10                  15

Glu Asn Glu Tyr Asp Val Ile Tyr Leu Lys Pro Leu Ala Gly Val Tyr
            20                  25                  30

Arg Ser Leu Lys Lys Gln Ile Glu Lys Asn Ile Phe Thr Phe Asn Leu
        35                  40                  45

Asn Leu Asn Asp Ile Leu Asn Ser Arg Leu Lys Lys Arg Lys Tyr Phe
    50                  55                  60

Leu Asp Val Leu Glu Ser Asp Leu Met Gln Phe Lys His Ile Ser Ser
65                  70                  75                  80

Asn Glu Tyr Ile Ile Glu Asp Ser Phe Lys Leu Leu Asn Ser Glu Gln
                85                  90                  95

Lys Asn Thr Leu Leu Lys Ser Tyr Lys Tyr Ile Lys Glu Ser Val Glu
            100                 105                 110

Asn Asp Ile Lys Phe Ala Gln Glu Gly Ile Ser Tyr Tyr Glu Lys Val
        115                 120                 125

Leu Ala Lys Tyr Lys Asp Asp Leu Glu Ser Ile Lys Lys Val Ile Lys
    130                 135                 140

Glu Glu Lys Glu Lys Phe Pro Ser Ser Pro Thr Thr Pro Pro Ser
145                 150                 155                 160

Pro Ala Lys Thr Asp Glu Gln Lys Lys Glu Ser Lys Phe Leu Pro Phe
                165                 170                 175

Leu Thr Asn Ile Glu Thr Leu Tyr Asn Asn Leu Val Asn Lys Ile Asp
            180                 185                 190

Asp Tyr Leu Ile Asn Leu Lys Ala Lys Ile Asn Asp Cys Asn Val Glu
        195                 200                 205

Lys Asp Glu Ala His Val Lys Ile Thr Lys Leu Ser Asp Leu Lys Ala
    210                 215                 220

Ile Asp Asp Lys Ile Asp Leu Phe Lys Asn Pro Tyr Asp Phe Glu Ala
225                 230                 235                 240

Ile Lys Lys Leu Ile Asn Asp Asp Thr Lys Lys Asp Met Leu Gly Lys
                245                 250                 255

Leu Leu Ser Thr Gly Leu Val Gln Asn Phe Pro Asn Thr Ile Ile Ser
            260                 265                 270

Lys Leu Ile Glu Gly Lys Phe Gln Asp Met Leu Asn Ile Ser Gln His
        275                 280                 285

Gln Cys Val Lys Lys Gln Cys Pro Glu Asn Ser Gly Cys Phe Arg His
    290                 295                 300

Leu Asp Glu Arg Glu Glu Cys Lys Cys Leu Leu Asn Tyr Lys Gln Glu
305                 310                 315                 320

Gly Asp Lys Cys Val Glu Asn Pro Asn Pro Thr Cys Asn Glu Asn Asn
                325                 330                 335

Gly Gly Cys Asp Ala Asp Ala Thr Cys Thr Glu Glu Asp Ser Gly Ser
            340                 345                 350

Ser Arg Lys Lys Ile Thr Cys Glu Cys Thr Lys Pro Asp Ser Tyr Pro
        355                 360                 365

Leu Phe Asp Gly Ile Phe Cys Ser Ser Ser Asn Phe Leu Gly Ile Ser
    370                 375                 380

Phe Leu Leu Ile Leu Met Leu Ile Leu Tyr Ser Phe Ile
385                 390                 395

<210> SEQ ID NO 20
<211> LENGTH: 1293
<212> TYPE: DNA
<213> ORGANISM: Artificial
<220> FEATURE:
<223> OTHER INFORMATION: Synthetic

<400> SEQUENCE: 20

```
atgaccgtcg cgcggccgag cgtgcccgcg gcgctgcccc tcctcgggga gctccccgg      60
ctgctacttc tggtgctgtt gtgcctgccg ccgtgtggg gtggcgaggc catctccgtg     120
accatggaca acatcctgtc cggcttcgag aacgagtacg acgtgatcta cctgaagccc     180
ctggccggcg tgtaccgctc cctgaagaag cagatcgaga gaacatctt caccttcaac     240
ctgaacctga cgacatcct gaactcccgc tgaagaagc gcaagtactt cctggacgtg     300
ctggagtccg acctgatgca gttcaagcac atctcctcca cgagtacat catcgaggac     360
tccttcaagc tgctgaactc cgagcagaag aacaccctgc tgaagtccta caagtacatc     420
aaggagtccg tggagaacga catcaagttc gcccaggagg catctccta ctacgagaag     480
gtgctggcca agtacaagga cgacctggag tccatcaaga aggtgatcaa ggaggagaag     540
gagaagttcc cctcctcccc ccccaccacc ccccctccc ccgccaagac cgacgagcag     600
aagaaggagt ccaagttcct gcccttcctg accaacatcg agaccctgta caacaacctg     660
gtgaacaaga tcgacgacta cctgatcaac ctgaaggcca agatcaacga ctgcaacgtg     720
gagaaggacg aggcccacgt gaagatcacc aagctgtccg acctgaaggc catcgacgac     780
aagatcgacc tgttcaagaa ccccctacgac ttcgaggcca tcaagaagct gatcaacgac     840
gacaccaaga aggacatgct gggcaagctg ctgtccaccg gcctggtgca gaacttcccc     900
aacaccatca tctccaagct gatcgagggc aagttccagg acatgctgaa catctcccag     960
caccagtgcg tgaagaagca gtgccccgag aactccggct gcttccgcca cctggacgag    1020
cgcgaggagt gcaagtgcct gctgaactac aagcaggagg cgacaagtg cgtggagaac    1080
cccaacccca cctgcaacga gaacaacggc ggctgcgacg ccgacgccac ctgcaccgag    1140
gaggactccg gctcctcccg caagaagatc acctgcgagt gcaccaagcc cgactcctac    1200
cccctgttcg acggcatctt ctgctcctcc tccaacttcc tgggcatctc cttcctgctg    1260
atcctgatgc tgatcctgta ctccttcatc taa                                 1293
```

<210> SEQ ID NO 21
<211> LENGTH: 430
<212> TYPE: PRT
<213> ORGANISM: Artificial
<220> FEATURE:
<223> OTHER INFORMATION: Synthetic

<400> SEQUENCE: 21

Met Thr Val Ala Arg Pro Ser Val Pro Ala Ala Leu Pro Leu Leu Gly
1               5                   10                  15

Glu Leu Pro Arg Leu Leu Leu Val Leu Leu Cys Leu Pro Ala Val
            20                  25                  30

Trp Gly Gly Glu Ala Ile Ser Val Thr Met Asp Asn Ile Leu Ser Gly
        35                  40                  45

Phe Glu Asn Glu Tyr Asp Val Ile Tyr Leu Lys Pro Leu Ala Gly Val
    50                  55                  60

Tyr Arg Ser Leu Lys Lys Gln Ile Glu Lys Asn Ile Phe Thr Phe Asn
65                  70                  75                  80

Leu Asn Leu Asn Asp Ile Leu Asn Ser Arg Leu Lys Lys Arg Lys Tyr
            85                  90                  95

Phe Leu Asp Val Leu Glu Ser Asp Leu Met Gln Phe Lys His Ile Ser
        100                 105                 110

Ser Asn Glu Tyr Ile Ile Glu Asp Ser Phe Lys Leu Leu Asn Ser Glu
    115                 120                 125

Gln Lys Asn Thr Leu Leu Lys Ser Tyr Lys Tyr Ile Lys Glu Ser Val
130                 135                 140

Glu Asn Asp Ile Lys Phe Ala Gln Glu Gly Ile Ser Tyr Tyr Glu Lys
145                 150                 155                 160

Val Leu Ala Lys Tyr Lys Asp Asp Leu Glu Ser Ile Lys Val Ile
                165                 170                 175

Lys Glu Glu Lys Glu Lys Phe Pro Ser Ser Pro Thr Thr Pro Pro
                180                 185                 190

Ser Pro Ala Lys Thr Asp Glu Gln Lys Lys Glu Ser Lys Phe Leu Pro
        195                 200                 205

Phe Leu Thr Asn Ile Glu Thr Leu Tyr Asn Asn Leu Val Asn Lys Ile
        210                 215                 220

Asp Asp Tyr Leu Ile Asn Leu Lys Ala Lys Ile Asn Asp Cys Asn Val
225                 230                 235                 240

Glu Lys Asp Glu Ala His Val Lys Ile Thr Lys Leu Ser Asp Leu Lys
                245                 250                 255

Ala Ile Asp Asp Lys Ile Asp Leu Phe Lys Asn Pro Tyr Asp Phe Glu
                260                 265                 270

Ala Ile Lys Lys Leu Ile Asn Asp Asp Thr Lys Lys Asp Met Leu Gly
                275                 280                 285

Lys Leu Leu Ser Thr Gly Leu Val Gln Asn Phe Pro Asn Thr Ile Ile
        290                 295                 300

Ser Lys Leu Ile Glu Gly Lys Phe Gln Asp Met Leu Asn Ile Ser Gln
305                 310                 315                 320

His Gln Cys Val Lys Lys Gln Cys Pro Glu Asn Ser Gly Cys Phe Arg
                325                 330                 335

His Leu Asp Glu Arg Glu Glu Cys Lys Cys Leu Leu Asn Tyr Lys Gln
                340                 345                 350

Glu Gly Asp Lys Cys Val Glu Asn Pro Asn Pro Thr Cys Asn Glu Asn
                355                 360                 365

Asn Gly Gly Cys Asp Ala Asp Ala Thr Cys Thr Glu Glu Asp Ser Gly
        370                 375                 380

Ser Ser Arg Lys Lys Ile Thr Cys Glu Cys Thr Lys Pro Asp Ser Tyr
385                 390                 395                 400

Pro Leu Phe Asp Gly Ile Phe Cys Ser Ser Ser Asn Phe Leu Gly Ile
                405                 410                 415

Ser Phe Leu Leu Ile Leu Met Leu Ile Leu Tyr Ser Phe Ile
                420                 425                 430

<210> SEQ ID NO 22
<211> LENGTH: 1293
<212> TYPE: DNA
<213> ORGANISM: Artificial
<220> FEATURE:
<223> OTHER INFORMATION: Synthetic

<400> SEQUENCE: 22
atgaccgtcg cgcggccgag cgtgcccgcg gcgctgcccc tcctcgggga gctccccgg      60

```
ctgctacttc tggtgctgtt gtgcctgccg gccgtgtggg gtggcgaggc catctccgtg      120
accatggaca acatcctgtc cggcttcgag aacgagtacg acgtgatcta cctgaagccc      180
ctggccggcg tgtaccgctc cctgaagaag cagatcgaga gaacatcttc accttcaac       240 ctgaacctga cgacatcct gaactcccgc tgaagaagc gcaagtactt cctggacgtg        300
ctggagtccg acctgatgca gttcaagcac atctcctcca acgagtacat catcgaggac      360
tccttcaagc tgctgaactc cgagcagaag aaccctgc tgaagtccta caagtacatc        420
aaggagtccg tggagaacga catcaagttc gcccaggagg catctcctc ctacgagaag       480 gtgctggcca agtacaagga cgacctggag tccatcaaga aggtgatcaa ggaggagaag      540
gagaagttcc cctcctcccc ccccaccacc cccccctccc ccgccaagac cgacgagcag      600
aagaaggagt ccaagttcct gcccttcctg accaacatcg agaccctgta caacaacctg      660
gtgaacaaga tcgacgacta cctgatcaac ctgaaggcca agatcaacga ctgcaacgtg      720
gagaaggacg aggcccacgt gaagatcacc aagctgtccg acctgaaggc catcgacgac      780
aagatcgacc tgttcaagaa cccctacgac ttcgaggcca tcaagaagct gatcaacgac      840
gacaccaaga aggacatgct gggcaagctg ctgtccaccg gcctggtgca gaacttcccc      900
aacaccatca tctccaagct gatcgagggc aagttccagg acatgctcca gatctcccag      960
caccagtgcg tgaagaagca gtgccccgag aactccggct gcttccgcca cctggacgag     1020
cgcgaggagt gcaagtgcct gctgaactac aagcaggagg cgacaagtg cgtggagaac      1080 cccaaccccca cctgcaacga gaacaacggc ggctgcgacg ccgacgccac ctgcaccgag    1140
gaggactccg gctcctcccg caagaagatc acctgcgagt gcaccaagcc cgactcctac     1200
cccctgttcg acggcatctt ctgctcctcc tccaacttcc tgggcatctc cttcctgctg     1260
atcctgatgc tgatcctgta ctccttcatc taa                                  1293
```

<210> SEQ ID NO 23
<211> LENGTH: 430
<212> TYPE: PRT
<213> ORGANISM: Artificial
<220> FEATURE:
<223> OTHER INFORMATION: Synthetic

<400> SEQUENCE: 23

```
Met Thr Val Ala Arg Pro Ser Val Pro Ala Leu Pro Leu Leu Gly
1               5                   10                  15

Glu Leu Pro Arg Leu Leu Leu Val Leu Leu Cys Leu Pro Ala Val
            20                  25                  30

Trp Gly Gly Glu Ala Ile Ser Val Thr Met Asp Asn Ile Leu Ser Gly
            35                  40                  45

Phe Glu Asn Glu Tyr Asp Val Ile Tyr Leu Lys Pro Leu Ala Gly Val
50                  55                  60

Tyr Arg Ser Leu Lys Lys Gln Ile Glu Lys Asn Ile Phe Thr Phe Asn
65                  70                  75                  80

Leu Asn Leu Asn Asp Ile Leu Asn Ser Arg Leu Lys Lys Arg Lys Tyr
                85                  90                  95

Phe Leu Asp Val Leu Glu Ser Asp Leu Met Gln Phe Lys His Ile Ser
                100                 105                 110

Ser Asn Glu Tyr Ile Ile Glu Asp Ser Phe Lys Leu Leu Asn Ser Glu
        115                 120                 125

Gln Lys Asn Thr Leu Leu Lys Ser Tyr Lys Tyr Ile Lys Glu Ser Val
    130                 135                 140
```

Glu Asn Asp Ile Lys Phe Ala Gln Glu Gly Ile Ser Tyr Tyr Glu Lys
145                 150                 155                 160

Val Leu Ala Lys Tyr Lys Asp Asp Leu Glu Ser Ile Lys Lys Val Ile
            165                 170                 175

Lys Glu Glu Lys Glu Lys Phe Pro Ser Ser Pro Thr Thr Pro Pro
        180                 185                 190

Ser Pro Ala Lys Thr Asp Glu Gln Lys Lys Glu Ser Lys Phe Leu Pro
        195                 200                 205

Phe Leu Thr Asn Ile Glu Thr Leu Tyr Asn Asn Leu Val Asn Lys Ile
        210                 215                 220

Asp Asp Tyr Leu Ile Asn Leu Lys Ala Lys Ile Asn Asp Cys Asn Val
225                 230                 235                 240

Glu Lys Asp Glu Ala His Val Lys Ile Thr Lys Leu Ser Asp Leu Lys
            245                 250                 255

Ala Ile Asp Asp Lys Ile Asp Leu Phe Lys Asn Pro Tyr Asp Phe Glu
            260                 265                 270

Ala Ile Lys Lys Leu Ile Asn Asp Asp Thr Lys Lys Asp Met Leu Gly
            275                 280                 285

Lys Leu Leu Ser Thr Gly Leu Val Gln Asn Phe Pro Asn Thr Ile Ile
        290                 295                 300

Ser Lys Leu Ile Glu Gly Lys Phe Gln Asp Met Leu Gln Ile Ser Gln
305                 310                 315                 320

His Gln Cys Val Lys Gln Cys Pro Glu Asn Ser Gly Cys Phe Arg
            325                 330                 335

His Leu Asp Glu Arg Glu Glu Cys Lys Cys Leu Leu Asn Tyr Lys Gln
            340                 345                 350

Glu Gly Asp Lys Cys Val Glu Asn Pro Asn Pro Thr Cys Asn Glu Asn
        355                 360                 365

Asn Gly Gly Cys Asp Ala Asp Ala Thr Cys Thr Glu Glu Asp Ser Gly
        370                 375                 380

Ser Ser Arg Lys Lys Ile Thr Cys Glu Cys Thr Lys Pro Asp Ser Tyr
385                 390                 395                 400

Pro Leu Phe Asp Gly Ile Phe Cys Ser Ser Ser Asn Phe Leu Gly Ile
            405                 410                 415

Ser Phe Leu Leu Ile Leu Met Leu Ile Leu Tyr Ser Phe Ile
        420                 425                 430

<210> SEQ ID NO 24
<211> LENGTH: 1335
<212> TYPE: DNA
<213> ORGANISM: Artificial
<220> FEATURE:
<223> OTHER INFORMATION: Synthetic

<400> SEQUENCE: 24
atgaccgtcg cgcggccgag cgtgcccgcg gcgctgcccc tcctcgggga gctccccgg      60 ctgctacttc tggtgctgtt gtgcctgccg gccgtgtggg gtggcgaggc catctccgtg    120
accatggaca catcctgtc cggcttcgag aacgagtacg acgtgatcta cctgaagccc     180
ctggccggcg tgtaccgctc cctgaagaag cagatcgaga gaacatcttc accttcaac    240 ctgaacctga cgacatcct gaactcccgc tgaagaagc gcaagtactt cctggacgtg     300
ctggagtccg acctgatgca gttcaagcac atctcctcca acgagtacat catcgaggac    360
tccttcaagc tgctgaactc cgagcagaag aacaccctgc tgaagtccta caagtacatc    420
aaggagtccg tggagaacga catcaagttc gcccaggagg gcatctccta ctacgagaag    480

-continued

```
gtgctggcca agtacaagga cgacctggag tccatcaaga aggtgatcaa ggaggagaag      540
gagaagttcc cctcctcccc ccccaccacc ccccccctccc ccgccaagac cgacgagcag      600
aagaaggagt ccaagttcct gcccttcctg accaacatcg agaccctgta caacaacctg      660
gtgaacaaga tcgacgacta cctgatcaac ctgaaggcca gatcaacga ctgcaacgtg        720 gagaaggacg aggcccacgt gaagatcacc aagctgtccg acctgaaggc catcgacgac      780
aagatcgacc tgttcaagaa cccctacgac ttcgaggcca tcaagaagct gatcaacgac      840
gacaccaaga aggacatgct gggcaagctg ctgtccaccg gcctggtgca gaacttcccc      900
aacaccatca tctccaagct gatcgagggc aagttccagg acatgctgaa catctcccag      960
caccagtgcg tgaagaagca gtgccccgag aactccggct gcttccgcca cctggacgag     1020
cgcgaggagt gcaagtgcct gctgaactac aagcaggagg cgacaagtg cgtggagaac      1080 cccaacccca cctgcaacga gaacaacggc ggctgcgacg ccgacgccac ctgcaccgag     1140
gaggactccg gctcctcccg caagaagatc acctgcgagt gcaccaagcc cgactcctac     1200
cccctgttcg acggcatctt ctgctcctcc tccatgcata ccaccagcgg caccacgcgt     1260
ctgctgagcg ccacacctg cttcaccctg accggcctgc tgggtaccct ggtgaccatg      1320
ggcctgctga cctaa                                                       1335
```

<210> SEQ ID NO 25
<211> LENGTH: 444
<212> TYPE: PRT
<213> ORGANISM: Artificial
<220> FEATURE:
<223> OTHER INFORMATION: Synthetic

<400> SEQUENCE: 25

```
Met Thr Val Ala Arg Pro Ser Val Pro Ala Ala Leu Pro Leu Leu Gly
1               5                   10                  15

Glu Leu Pro Arg Leu Leu Leu Val Leu Leu Cys Leu Pro Ala Val
            20                  25                  30

Trp Gly Gly Glu Ala Ile Ser Val Thr Met Asp Asn Ile Leu Ser Gly
        35                  40                  45

Phe Glu Asn Glu Tyr Asp Val Ile Tyr Leu Lys Pro Leu Ala Gly Val
    50                  55                  60

Tyr Arg Ser Leu Lys Lys Gln Ile Glu Lys Asn Ile Phe Thr Phe Asn
65                  70                  75                  80

Leu Asn Leu Asn Asp Ile Leu Asn Ser Arg Leu Lys Lys Arg Lys Tyr
                85                  90                  95

Phe Leu Asp Val Leu Glu Ser Asp Leu Met Gln Phe Lys His Ile Ser
            100                 105                 110

Ser Asn Glu Tyr Ile Ile Glu Asp Ser Phe Lys Leu Leu Asn Ser Glu
        115                 120                 125

Gln Lys Asn Thr Leu Leu Lys Ser Tyr Lys Tyr Ile Lys Glu Ser Val
    130                 135                 140

Glu Asn Asp Ile Lys Phe Ala Gln Glu Gly Ile Ser Tyr Tyr Glu Lys
145                 150                 155                 160

Val Leu Ala Lys Tyr Lys Asp Asp Leu Glu Ser Ile Lys Lys Val Ile
                165                 170                 175

Lys Glu Glu Lys Glu Lys Phe Pro Ser Ser Pro Thr Thr Pro Pro
            180                 185                 190

Ser Pro Ala Lys Thr Asp Glu Gln Lys Lys Glu Ser Lys Phe Leu Pro
        195                 200                 205
```

```
Phe Leu Thr Asn Ile Glu Thr Leu Tyr Asn Asn Leu Val Asn Lys Ile
    210                 215                 220

Asp Asp Tyr Leu Ile Asn Leu Lys Ala Lys Ile Asn Asp Cys Asn Val
225                 230                 235                 240

Glu Lys Asp Glu Ala His Val Lys Ile Thr Lys Leu Ser Asp Leu Lys
                245                 250                 255

Ala Ile Asp Asp Lys Ile Asp Leu Phe Lys Asn Pro Tyr Asp Phe Glu
                260                 265                 270

Ala Ile Lys Lys Leu Ile Asn Asp Asp Thr Lys Lys Asp Met Leu Gly
            275                 280                 285

Lys Leu Leu Ser Thr Gly Leu Val Gln Asn Phe Pro Asn Thr Ile Ile
    290                 295                 300

Ser Lys Leu Ile Glu Gly Lys Phe Gln Asp Met Leu Asn Ile Ser Gln
305                 310                 315                 320

His Gln Cys Val Lys Lys Gln Cys Pro Glu Asn Ser Gly Cys Phe Arg
                325                 330                 335

His Leu Asp Glu Arg Glu Glu Cys Lys Cys Leu Leu Asn Tyr Lys Gln
                340                 345                 350

Glu Gly Asp Lys Cys Val Glu Asn Pro Asn Pro Thr Cys Asn Glu Asn
            355                 360                 365

Asn Gly Gly Cys Asp Ala Asp Ala Thr Cys Thr Glu Glu Asp Ser Gly
370                 375                 380

Ser Ser Arg Lys Lys Ile Thr Cys Glu Cys Thr Lys Pro Asp Ser Tyr
385                 390                 395                 400

Pro Leu Phe Asp Gly Ile Phe Cys Ser Ser Ser Met His Thr Thr Ser
                405                 410                 415

Gly Thr Thr Arg Leu Leu Ser Gly His Thr Cys Phe Thr Leu Thr Gly
            420                 425                 430

Leu Leu Gly Thr Leu Val Thr Met Gly Leu Leu Thr
            435                 440

<210> SEQ ID NO 26
<211> LENGTH: 1404
<212> TYPE: DNA
<213> ORGANISM: Artificial
<220> FEATURE:
<223> OTHER INFORMATION: Synthetic

<400> SEQUENCE: 26
atgaagcaca tcctgtacat ctccttctac ttcatcctgg tgaacctgct gatcttccac      60
atcaacggca agatcaccaa gaactccgag aaggacgaga tcatcaagtc caacctgcgc     120
tccggctcct ccaactcccg caaccgcatc aacgaggaga gcacgagaa gaagcacgtg     180 ctgtcccaca ctcctacga gaagaccaag aacaacgaga caacaagtt cttcgacaag     240 gacaaggagc tgaccatgtc caacgtgaag aacgtgtccc agaccaactt caagtccctg     300
ctgcgcaacc tgggcgtgtc cgagaacatc ttcctgaagg agaacaagct gaacaaggag     360
ggcaagctga tcgagcacat catcaacgac gacgacgaca agaagaagta catcaagggc     420
caggacgaga accgccagga ggacctggag aaggccgccg agcagcagtc cgacctggag     480
caggagcgcc tggccaagga agctgcag gagcgccgcg ccaaggagaa gctgcaggag     540
cagcagcgcg acctggagca gcgcaaggcc gacaccaaga gaacctgga gcgcaagaag     600 gagcacggca acgtgctggc cgaggacctg tacggccgcc tggagatccc cgccatcgag     660
ctgccctccg agaacgagcg cggctactac atcccccacc agtcctccct gccccaggac     720
```

```
aaccgcggca actcccgcga ctccaaggag atctccatcg tggagaacac caaccgcgag    780
tccatcacca ccaacgtgga gggccgccgc gacatccaca agggccacct ggaggagaag    840
aaggacggct ccatcaagcc cgagcagaag gaggacaagt ccgccgacat ccagaaccac    900
accctggaga ccgtgaacat ctccgacgtg aacgacttcc agatctccaa gtacgaggac    960
gagatctccg ccgagtacga cgactccctg atcgacgagg aggaggacga cgaggacctg   1020
gacgagttca gcccatcgt gcagtacgac aacttccagg acgaggagaa catcggcatc   1080
tacaaggagc tggaggacct gatcgagaag aacgagaacc tggacgacct ggacgagggc   1140
atcgagaagt cctccgagga gctgtccgag gagaagatca agaagggcaa gaagtacgag   1200
aagaccaagg acaacaactt caagcccaac gacaagtccc tgtacgacga gcacatcaag   1260
aagtacaaga cgacaagca ggtgaacaag gagaaggaga agttcatcaa gtccctgttc   1320
cacatcttcg acggcgacaa cgagatcctg cagatcgtgg acgagctgtc cgaggacatc   1380
accaagtact tcatgaagct gtaa                                          1404
```

<210> SEQ ID NO 27
<211> LENGTH: 467
<212> TYPE: PRT
<213> ORGANISM: Artificial
<220> FEATURE:
<223> OTHER INFORMATION: Synthetic

<400> SEQUENCE: 27

```
Met Lys His Ile Leu Tyr Ile Ser Phe Tyr Phe Ile Leu Val Asn Leu
1               5                   10                  15

Leu Ile Phe His Ile Asn Gly Lys Ile Thr Lys Asn Ser Glu Lys Asp
            20                  25                  30

Glu Ile Ile Lys Ser Asn Leu Arg Ser Gly Ser Asn Ser Arg Asn
        35                  40                  45

Arg Ile Asn Glu Glu Lys His Glu Lys Lys His Val Leu Ser His Asn
    50                  55                  60

Ser Tyr Glu Lys Thr Lys Asn Asn Glu Asn Asn Lys Phe Phe Asp Lys
65                  70                  75                  80

Asp Lys Glu Leu Thr Met Ser Asn Val Lys Asn Val Ser Gln Thr Asn
                85                  90                  95

Phe Lys Ser Leu Leu Arg Asn Leu Gly Val Ser Glu Asn Ile Phe Leu
            100                 105                 110

Lys Glu Asn Lys Leu Asn Lys Glu Gly Lys Leu Ile Glu His Ile Ile
        115                 120                 125

Asn Asp Asp Asp Lys Lys Lys Tyr Ile Lys Gly Gln Asp Glu Asn
    130                 135                 140

Arg Gln Glu Asp Leu Glu Lys Ala Ala Glu Gln Ser Asp Leu Glu
145                 150                 155                 160

Gln Glu Arg Leu Ala Lys Glu Lys Leu Gln Glu Arg Arg Ala Lys Glu
                165                 170                 175

Lys Leu Gln Glu Gln Gln Arg Asp Leu Glu Gln Arg Lys Ala Asp Thr
            180                 185                 190

Lys Lys Asn Leu Glu Arg Lys Lys Glu His Gly Asp Val Leu Ala Glu
        195                 200                 205

Asp Leu Tyr Gly Arg Leu Glu Ile Pro Ala Ile Glu Leu Pro Ser Glu
    210                 215                 220

Asn Glu Arg Gly Tyr Tyr Ile Pro His Gln Ser Ser Leu Pro Gln Asp
225                 230                 235                 240
```

```
Asn Arg Gly Asn Ser Arg Asp Ser Lys Glu Ile Ser Ile Val Glu Asn
                245                 250                 255

Thr Asn Arg Glu Ser Ile Thr Thr Asn Val Glu Gly Arg Arg Asp Ile
            260                 265                 270

His Lys Gly His Leu Glu Glu Lys Lys Asp Gly Ser Ile Lys Pro Glu
        275                 280                 285

Gln Lys Glu Asp Lys Ser Ala Asp Ile Gln Asn His Thr Leu Glu Thr
    290                 295                 300

Val Asn Ile Ser Asp Val Asn Asp Phe Gln Ile Ser Lys Tyr Glu Asp
305                 310                 315                 320

Glu Ile Ser Ala Glu Tyr Asp Asp Ser Leu Ile Asp Glu Glu Glu Asp
                325                 330                 335

Asp Glu Asp Leu Asp Glu Phe Lys Pro Ile Val Gln Tyr Asp Asn Phe
            340                 345                 350

Gln Asp Glu Glu Asn Ile Gly Ile Tyr Lys Glu Leu Glu Asp Leu Ile
        355                 360                 365

Glu Lys Asn Glu Asn Leu Asp Asp Leu Asp Glu Gly Ile Glu Lys Ser
    370                 375                 380

Ser Glu Glu Leu Ser Glu Lys Ile Lys Lys Gly Lys Lys Tyr Glu
385                 390                 395                 400

Lys Thr Lys Asp Asn Asn Phe Lys Pro Asn Asp Lys Ser Leu Tyr Asp
                405                 410                 415

Glu His Ile Lys Lys Tyr Lys Asn Asp Lys Gln Val Asn Lys Glu Lys
            420                 425                 430

Glu Lys Phe Ile Lys Ser Leu Phe His Ile Phe Asp Gly Asp Asn Glu
        435                 440                 445

Ile Leu Gln Ile Val Asp Glu Leu Ser Glu Asp Ile Thr Lys Tyr Phe
    450                 455                 460

Met Lys Leu
465

<210> SEQ ID NO 28
<211> LENGTH: 1533
<212> TYPE: DNA
<213> ORGANISM: Artificial
<220> FEATURE:
<223> OTHER INFORMATION: Synthetic

<400> SEQUENCE: 28
atggactgct ccggctccat ccgccgccac aactgggtga ccacgccgt gccctggcc      60 atgaagctga tccagcagct gaacctgaac gacaacgcca tccacctgta cgcctccgtg    120
ttctccaaca cgcccgcga gatcatccgc ctgcactccg acgcctccaa gaacaaggag    180
aaggccctga tcatcatcaa gtccctgctg tccaccaacc tgccctacgg caagaccaac    240
ctgaccgacg ccctgctgca ggtgcgcaag cacctgaacg accgcatcaa ccgcgagaac    300
gccaaccagc tggtggtgat cctgaccgac ggcatccccg actccatcca ggactccctg    360
aaggagtccc gcaagctgtc cgaccgcggc gtgaagatcg ccgtgttcgg catcggccag    420
ggcatcaacg tggccttcaa ccgcttcctg gtgggctgcc acccctccga cggcaagtgc    480
aacctgtacg ccgactccgc ctgggagaac gtgaagaacg tgatcggccc cttcatgaag    540
gccgtgtgcg tggaggtgga aagaccgcc tcctgcggcg tgtgggacga gtggtccccc    600
tgctccgtga cctgcggcaa gggcacccgc tcccgcaagc gcgagatcct gcacgagggc    660
tgcacctccg agctgcagga gcagtgcgag gaggagcgct gcctgcccaa gcgcgagccc    720
```

```
ctggacgtgc cgacgagcc cgaggacgac cagccccgcc cccgcggcga caacttcgcc    780
gtggagaagc ccaacgagaa catcatcgac aacaacccc aggagccctc ccccaacccc    840
gaggagggca agggcgagaa ccccaacggc ttcgacctgg acgagaaccc cgagaacccc    900
cccaaccccc ccaaccccga catccccgag caggagccca acatccccga ggactccgag    960
aaggaggtgc cctccgacgt gcccaagaac ccgaggacg accgcgagga gaacttcgac   1020
atccccaaga agcccgagaa caagcacgac aaccagaaca acctgcccaa cgacaagtcc   1080
gaccgctaca tcccctactc cccctgtcc ccaaggtgc tggacaacga gcgcaagcag    1140
tccgaccccc agtcccagga caacaacggc aaccgccacg tgcccaactc cgaggaccgc   1200
gagacccgcc cccacggccg caacaacgag aaccgctcct acaaccgcaa gcacaacaac   1260
acccccaagc accccgagcg cgaggagcac gagaagcccg acaacaacaa gaagaaggcc   1320
ggctccgaca caagtacaa gatcgccggc ggcatcgccg gcggcctggc cctgctggcc    1380
tgcgccggcc tggcctacaa gttcgtggtg cccggcgccg ccacccccta cgccggcgag   1440 cccgcccct tcgacgagac cctgggcgag gaggacaagg acctggacga gcccgagcag   1500
ttccgcctgc ccgaggagaa cgagtggaac taa                               1533

<210> SEQ ID NO 29
<211> LENGTH: 510
<212> TYPE: PRT
<213> ORGANISM: Artificial
<220> FEATURE:
<223> OTHER INFORMATION: Synthetic

<400> SEQUENCE: 29

Met Asp Cys Ser Gly Ser Ile Arg Arg His Asn Trp Val Asn His Ala
1               5                   10                  15

Val Pro Leu Ala Met Lys Leu Ile Gln Gln Leu Asn Leu Asn Asp Asn
            20                  25                  30

Ala Ile His Leu Tyr Ala Ser Val Phe Ser Asn Asn Ala Arg Glu Ile
        35                  40                  45

Ile Arg Leu His Ser Asp Ala Ser Lys Asn Lys Glu Lys Ala Leu Ile
    50                  55                  60

Ile Ile Lys Ser Leu Leu Ser Thr Asn Leu Pro Tyr Gly Lys Thr Asn
65                  70                  75                  80

Leu Thr Asp Ala Leu Leu Gln Val Arg Lys His Leu Asn Asp Arg Ile
                85                  90                  95

Asn Arg Glu Asn Ala Asn Gln Leu Val Val Ile Leu Thr Asp Gly Ile
            100                 105                 110

Pro Asp Ser Ile Gln Asp Ser Leu Lys Glu Ser Arg Lys Leu Ser Asp
        115                 120                 125

Arg Gly Val Lys Ile Ala Val Phe Gly Ile Gly Gln Gly Ile Asn Val
    130                 135                 140

Ala Phe Asn Arg Phe Leu Val Gly Cys His Pro Ser Asp Gly Lys Cys
145                 150                 155                 160

Asn Leu Tyr Ala Asp Ser Ala Trp Glu Asn Val Lys Asn Val Ile Gly
                165                 170                 175

Pro Phe Met Lys Ala Val Cys Val Glu Val Lys Thr Ala Ser Cys
            180                 185                 190

Gly Val Trp Asp Glu Trp Ser Pro Cys Ser Val Thr Cys Gly Lys Gly
        195                 200                 205

Thr Arg Ser Arg Lys Arg Glu Ile Leu His Glu Gly Cys Thr Ser Glu
```

```
                210                 215                 220
Leu Gln Glu Gln Cys Glu Glu Arg Cys Leu Pro Lys Arg Glu Pro
225                 230                 235                 240

Leu Asp Val Pro Asp Glu Pro Glu Asp Gln Pro Arg Pro Arg Gly
            245                 250                 255

Asp Asn Phe Ala Val Glu Lys Pro Asn Glu Ile Ile Asp Asn Asn
                260                 265                 270

Pro Gln Glu Pro Ser Pro Asn Pro Glu Glu Gly Lys Gly Glu Asn
            275                 280                 285

Asn Gly Phe Asp Leu Asp Glu Asn Pro Glu Asn Pro Pro Asn Pro
290                 295                 300

Asn Pro Asp Ile Pro Glu Gln Glu Pro Asn Ile Pro Glu Asp Ser Glu
305                 310                 315                 320

Lys Glu Val Pro Ser Asp Val Pro Lys Asn Pro Glu Asp Asp Arg Glu
                325                 330                 335

Glu Asn Phe Asp Ile Pro Lys Lys Pro Glu Asn Lys His Asp Asn Gln
            340                 345                 350

Asn Asn Leu Pro Asn Asp Lys Ser Asp Arg Tyr Ile Pro Tyr Ser Pro
355                 360                 365

Leu Ser Pro Lys Val Leu Asp Asn Glu Arg Lys Gln Ser Asp Pro Gln
370                 375                 380

Ser Gln Asp Asn Gly Asn Arg His Val Pro Asn Ser Glu Asp Arg
385                 390                 395                 400

Glu Thr Arg Pro His Gly Arg Asn Asn Glu Asn Arg Ser Tyr Asn Arg
                405                 410                 415

Lys His Asn Asn Thr Pro Lys His Pro Glu Arg Glu Glu His Glu Lys
            420                 425                 430

Pro Asp Asn Asn Lys Lys Lys Ala Gly Ser Asp Asn Lys Tyr Lys Ile
            435                 440                 445

Ala Gly Gly Ile Ala Gly Gly Leu Ala Leu Leu Ala Cys Ala Gly Leu
            450                 455                 460

Ala Tyr Lys Phe Val Val Pro Gly Ala Ala Thr Pro Tyr Ala Gly Glu
465                 470                 475                 480

Pro Ala Pro Phe Asp Glu Thr Leu Gly Glu Glu Asp Lys Asp Leu Asp
                485                 490                 495

Glu Pro Glu Gln Phe Arg Leu Pro Glu Glu Asn Glu Trp Asn
            500                 505                 510

<210> SEQ ID NO 30
<211> LENGTH: 1563
<212> TYPE: DNA
<213> ORGANISM: Artificial
<220> FEATURE:
<223> OTHER INFORMATION: Synthetic

<400> SEQUENCE: 30
atgaaccacc tgggcaacgt gaagtacctg gtgatcgtgt cctgatcttc cttcgacctg      60
ttcctggtga acggccgcga cgtgcagaac aacatcgtgg acgagatcaa gtaccgcgag     120
gaggtgtgca acgacgaggt ggacctgtac ctgctgatgg actgctccgg ctccatccgc     180
cgccacaact gggtgaacca cccgtgcccc tggccatga agctgatcca gcagctgaac     240
ctgaacgaca cgccatcca cctgtacgcc tccgtgttct ccaacaacgc ccgcgagatc     300
atccgcctgc actccgacgc ctccaagaac aaggagaagg ccctgatcat catcaagtcc     360
ctgctgtcca ccaacctgcc ctacggcaag accaacctga ccgacgccct gctgcaggtg     420
```

```
cgcaagcacc tgaacgaccg catcaaccgc gagaacgcca accagctggt ggtgatcctg      480
accgacggca tccccgactc catccaggac tccctgaagg agtcccgcaa gctgtccgac      540
cgcggcgtga agatcgccgt gttcggcatc ggccagggca tcaacgtggc cttcaaccgc      600
ttcctggtgg gctgccaccc ctccgacggc aagtgcaacc tgtacgccga ctccgcctgg      660
gagaacgtga agaacgtgat cggccccttc atgaaggccg tgtgcgtgga ggtggagaag      720
accgcctcct gcggcgtgtg ggacgagtgg tcccccctgc tccgtgacctg cggcaagggc     780 acccgctccc gcaagcgcga gatcctgcac gagggctgca cctccgagct gcaggagcag      840
tgcgaggagg agcgctgcct gcccaagcgc gagcccctgg acgtgcccga cgagcccgag      900
gacgaccagc ccgccccccg cggcgacaac ttcgccgtgg agaagcccaa cgagaacatc      960
atcgacaaca ccccccagga gccctccccc aaccccgagg agggcaaggg cgagaacccc     1020
aacggcttcg acctggacga gaaccccgag aaccccccca cccccccaa ccccgacatc      1080 cccgagcagg agcccaacat ccccgaggac tccgagaagg aggtgccctc cgacgtgccc     1140
aagaaccccg aggacgaccg cgaggagaac ttcgacatcc ccaagaagcc cgagaacaag     1200
cacgacaacc agaacaacct gcccaacgac aagtccgacc gctacatccc ctactccccc     1260
ctgtccccca aggtgctgga caacgagcgc aagcagtccg accccagtc ccaggacaac      1320 aacggcaacc gccacgtgcc caactccgag gaccgcgaga cccgccccca cggccgcaac     1380
aacgagaacc gctcctacaa ccgcaagcac aacaacaccc ccaagcaccc cgagcgcgag     1440
gagcacgaga gcccgacaa caacaagaag aaggccggct ccgacaacaa gtacaagatc      1500
gccggcggca tcgccggcgg cctggccctg ctggcctgcg ccggcctggc ctacaagttc     1560
gtg                                                                  1563
```

```
<210> SEQ ID NO 31
<211> LENGTH: 521
<212> TYPE: PRT
<213> ORGANISM: Artificial
<220> FEATURE:
<223> OTHER INFORMATION: Synthetic

<400> SEQUENCE: 31

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
                20                  25                  30

Val Asp Glu Ile Lys Tyr Arg Glu Val Cys Asn Asp Glu Val Asp
            35                  40                  45

Leu Tyr Leu Leu Met Asp Cys Ser Gly Ser Ile Arg Arg His Asn Trp
    50                  55                  60

Val Asn His Ala Val Pro Leu Ala Met Lys Leu Ile Gln Gln Leu Asn
65                  70                  75                  80

Leu Asn Asp Asn Ala Ile His Leu Tyr Ala Ser Val Phe Ser Asn Asn
                85                  90                  95

Ala Arg Glu Ile Ile Arg Leu His Ser Asp Ala Ser Lys Asn Lys Glu
            100                 105                 110

Lys Ala Leu Ile Ile Ile Lys Ser Leu Leu Ser Thr Asn Leu Pro Tyr
        115                 120                 125

Gly Lys Thr Asn Leu Thr Asp Ala Leu Leu Gln Val Arg Lys His Leu
    130                 135                 140

Asn Asp Arg Ile Asn Arg Glu Asn Ala Asn Gln Leu Val Val Ile Leu
```

```
               145                 150                 155                 160
           Thr Asp Gly Ile Pro Asp Ser Ile Gln Asp Ser Leu Lys Glu Ser Arg
                           165                 170                 175
           Lys Leu Ser Asp Arg Gly Val Lys Ile Ala Val Phe Gly Ile Gly Gln
                           180                 185                 190
           Gly Ile Asn Val Ala Phe Asn Arg Phe Leu Val Gly Cys His Pro Ser
                           195                 200                 205
           Asp Gly Lys Cys Asn Leu Tyr Ala Asp Ser Ala Trp Glu Asn Val Lys
                           210                 215                 220
           Asn Val Ile Gly Pro Phe Met Lys Ala Val Cys Val Glu Val Glu Lys
           225                 230                 235                 240
           Thr Ala Ser Cys Gly Val Trp Asp Glu Trp Ser Pro Cys Ser Val Thr
                           245                 250                 255
           Cys Gly Lys Gly Thr Arg Ser Arg Lys Arg Glu Ile Leu His Glu Gly
                           260                 265                 270
           Cys Thr Ser Glu Leu Gln Glu Gln Cys Glu Glu Arg Cys Leu Pro
                           275                 280                 285
           Lys Arg Glu Pro Leu Asp Val Pro Asp Glu Pro Glu Asp Gln Pro
                           290                 295                 300
           Arg Pro Arg Gly Asp Asn Phe Ala Val Glu Lys Pro Asn Glu Asn Ile
           305                 310                 315                 320
           Ile Asp Asn Asn Pro Gln Glu Pro Ser Pro Asn Pro Glu Glu Gly Lys
                           325                 330                 335
           Gly Glu Asn Pro Asn Gly Phe Asp Leu Asp Glu Asn Pro Glu Asn Pro
                           340                 345                 350
           Pro Asn Pro Pro Asn Pro Asp Ile Pro Glu Gln Glu Pro Asn Ile Pro
                           355                 360                 365
           Glu Asp Ser Glu Lys Glu Val Pro Ser Asp Val Pro Lys Asn Pro Glu
                           370                 375                 380
           Asp Asp Arg Glu Glu Asn Phe Asp Ile Pro Lys Lys Pro Glu Asn Lys
           385                 390                 395                 400
           His Asp Asn Gln Asn Asn Leu Pro Asn Asp Lys Ser Asp Arg Tyr Ile
                           405                 410                 415
           Pro Tyr Ser Pro Leu Ser Pro Lys Val Leu Asp Asn Glu Arg Lys Gln
                           420                 425                 430
           Ser Asp Pro Gln Ser Gln Asp Asn Asn Gly Asn Arg His Val Pro Asn
                           435                 440                 445
           Ser Glu Asp Arg Glu Thr Arg Pro His Gly Arg Asn Asn Glu Asn Arg
                           450                 455                 460
           Ser Tyr Asn Arg Lys His Asn Asn Thr Pro Lys His Pro Glu Arg Glu
           465                 470                 475                 480
           Glu His Glu Lys Pro Asp Asn Asn Lys Lys Ala Gly Ser Asp Asn
                           485                 490                 495
           Lys Tyr Lys Ile Ala Gly Gly Ile Ala Gly Leu Ala Leu Leu Ala
                           500                 505                 510
           Cys Ala Gly Leu Ala Tyr Lys Phe Val
                           515                 520
```

ADENOVIRAL VECTOR-BASED MALARIA VACCINES

STATEMENT REGARDING FEDERALLY SPONSORED RESEARCH AND DEVELOPMENT

This invention was made in part with Government support under Cooperative Research and Development Agreement (CRADA) Number NMR-04-1869, and amendments thereto, executed between GenVec, Inc. and the Naval Medical Research Center (NMRC). The Government may have certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 86,649 Byte ASCII (Text) file named "702583_ST25.TXT," created on Feb. 28, 2008.

BACKGROUND OF THE INVENTION

Malaria is one of the most devastating parasitic diseases affecting humans. Indeed, 41% of the world's population live in areas where malaria is transmitted (e.g., parts of Africa, Asia, the Middle East, Central and South America, Hispaniola, and Oceania). The World Health Organization (WHO) and the Centers for Disease Control (CDC) estimate that malaria infects 300-500 million people and kills 700,000-3 million people annually, with the majority of deaths occurring in children in sub-Saharan Africa. Malaria also is a major health concern to U.S. military personnel deployed to tropical regions of the world. For example, in August 2003, 28% of the 26th Marine Expeditionary Unit and Joint Task Force briefly deployed to Monrovia, Liberia, were infected with the malaria parasite *Plasmodium falciparum*. In addition, one 157-man Marine Expeditionary Unit sustained a 44% malaria casualty rate over a 12-day period while stationed at Robert International Airport in Monrovia. In all conflicts during the past century conducted in malaria endemic areas, malaria has been the leading cause of casualties, exceeding enemy-inflicted casualties in its impact on "person-days" lost from duty.

To combat malaria during U.S. military operations, preventive drugs, insect repellants, and barriers have been used with some success, but developing drug resistance by the malaria parasite and insecticide resistance by mosquito vectors has limited the efficacy of these agents. Moreover, the logistical burden and side effects associated with the use of these agents often is associated with high non-compliance rates. Vaccines are the most cost effective and efficient therapeutic interventions for infectious diseases. In this regard, vaccination has the advantage of administration prior to military deployment and likely reduction in non-compliance risks. However, decades of research and development directed to a malaria vaccine have not proven successful. Recent efforts have focused on developing vaccines against several specific malaria genes and delivery vector systems including adenovirus, poxvirus, and plasmids. The current status of malaria vaccine development and clinical trials is reviewed in, for example, Graves and Gelband, *Cochrane Database Syst. Rev.*, 1: CD000129 (2003), Moore et al., *Lancet Infect. Dis.*, 2: 737-743 (2002), Carvalho et al., *Scand. J. Immunol.*, 56: 327-343 (2002), Moorthy and Hill, *Br. Med. Bull.*, 62: 59-72 (2002), Greenwood and Alonso, *Chem. Immunol.*, 80: 366-395 (2002), and Richie and Saul, *Nature*, 415: 694-701 (2002).

Over the past 15-20 years, a series of Phase 1/2 vaccine trials have been reported using synthetic peptides or recombinant proteins based on malarial antigens. Approximately 40 trials were reported as of 1998 (see Engers and Godal, *Parisitology Today*, 14: 56-64 (1998)). Most of these trials have been directed against the sporozoite stage or liver stage of the *Plasmodium* life cycle, where the use of experimental mosquito challenges allows rapid progress through Phase 1 to Phase 2a preliminary efficacy studies. Anti-sporozoite vaccines tested include completely synthetic peptides, conjugates of synthetic peptide with proteins such as tetanus toxoid (to provide T cell help), recombinant malaria proteins, particle-forming recombinant chimeric constructs, recombinant viruses, and bacteria and DNA vaccines. Several trials of asexual blood stage vaccines have used either synthetic peptide conjugates or recombinant proteins. There also has been a single trial of a transmission blocking vaccine (recombinant Pfs25). A recurring problem identified in all of these vaccination strategies is the difficulty in obtaining a sufficiently strong and long lasting immune response in humans, despite the strong immunogenic response in animal models.

To overcome these limitations, the development of potent immune-stimulatory conjugates or adjuvants to boost the human response has been explored, in addition to the development of vaccines directed against the circumsporozoite protein (CSP), the principal sporozoite coat protein. Anti-CSP vaccines using recombinant proteins, peptide conjugates, recombinant protein conjugates, and chimeric proteins have been shown to elicit anti-CSP antibodies. Although considerable efforts are still being directed at the development of protein-based vaccines, alternative technologies such as DNA and viral based vaccines have shown some promise with regard to immunogenicity and protective efficacy, at least in animal models.

In this regard, DNA vaccines encoding *Plasmodium* antigens have been developed and can induce CD8+ CTL and IFN-γ responses, as well as protection against sporozoite challenge in mice (see Sedegah et al., *Proc. Natl. Acad. Sci. USA*, 91: 9866-9870 (1994), and Doolan et al., *J. Exp. Med.*, 183: 1739-1746 (1996)) and monkeys (Wang et al., *Science*, 282: 476-480 (1998), Rogers et al., *Infect. Immun.*, 69: 5565-5572 (2001), and Rogers et al., *Infect. Immun.*, 70: 4329-4335 (2002)). Furthermore, Phase I and Phase 2a clinical trials have established the safety, tolerability, and immunogenicity of DNA vaccines encoding malaria antigens in normal healthy humans (see, e.g., Wang et al., *Infect Immun.*, 66: 4193-41202 (1998), Le et al., *Vaccine*, 18: 1893-1901 (2000), and Epstein et al., *Hum. Gene Ther.*, 13: 1551-1560 (2002)). However, the immunogenicity of first and second-generation DNA vaccines in nonhuman primates and in humans has been suboptimal. Even in murine models, DNA vaccines are not effective at activating both arms of the immune system (see, e.g., Doolan et al., supra, Sedegah et al., supra, Sedegah et al., *Proc. Natl. Acad. Sci. USA*, 95: 7648-7653 (1998), Zavala et al., *Virology*, 280: 155-159 (2001), and Pardoll, *Nat. Rev. Immunol*, 2: 227-238 (2002)).

Thus, there remains a need for improved constructs that effectively deliver malaria antigens to human hosts so as to prevent the onset of disease and/or protect human hosts from further infections. The invention provides such constructs. This and other advantages of the invention will become apparent from the detailed description provided herein.

BRIEF SUMMARY OF THE INVENTION

The invention provides an adenoviral vector comprising an adenoviral genome comprising three or more heterologous antigen-encoding nucleic acid sequences, wherein the three or more nucleic acid sequences are operably linked to at least two different promoters.

The invention also provides an adenoviral vector comprising an adenoviral genome comprising two or more nucleic acid sequences, wherein each nucleic acid sequence encodes a *Plasmodium* antigen and is operably linked to at least one promoter.

The invention further provides a method of inducing an immune response against malaria in a mammal. The method comprises administering to the mammal (a) an adenoviral vector comprising an adenoviral genome comprising three or more nucleic acid sequences, wherein each nucleic acid sequence encodes a *Plasmodium* pre-erythrocytic stage antigen and is operably linked to at least one promoter, and (b) an adenoviral vector comprising an adenoviral genome comprising two or more nucleic acid sequences, wherein each nucleic acid sequence encodes a *Plasmodium* blood-stage antigen and is operably linked to at least one promoter, wherein the antigens are expressed in the mammal to induce an immune response against malaria.

DETAILED DESCRIPTION OF THE INVENTION

Figure 1:
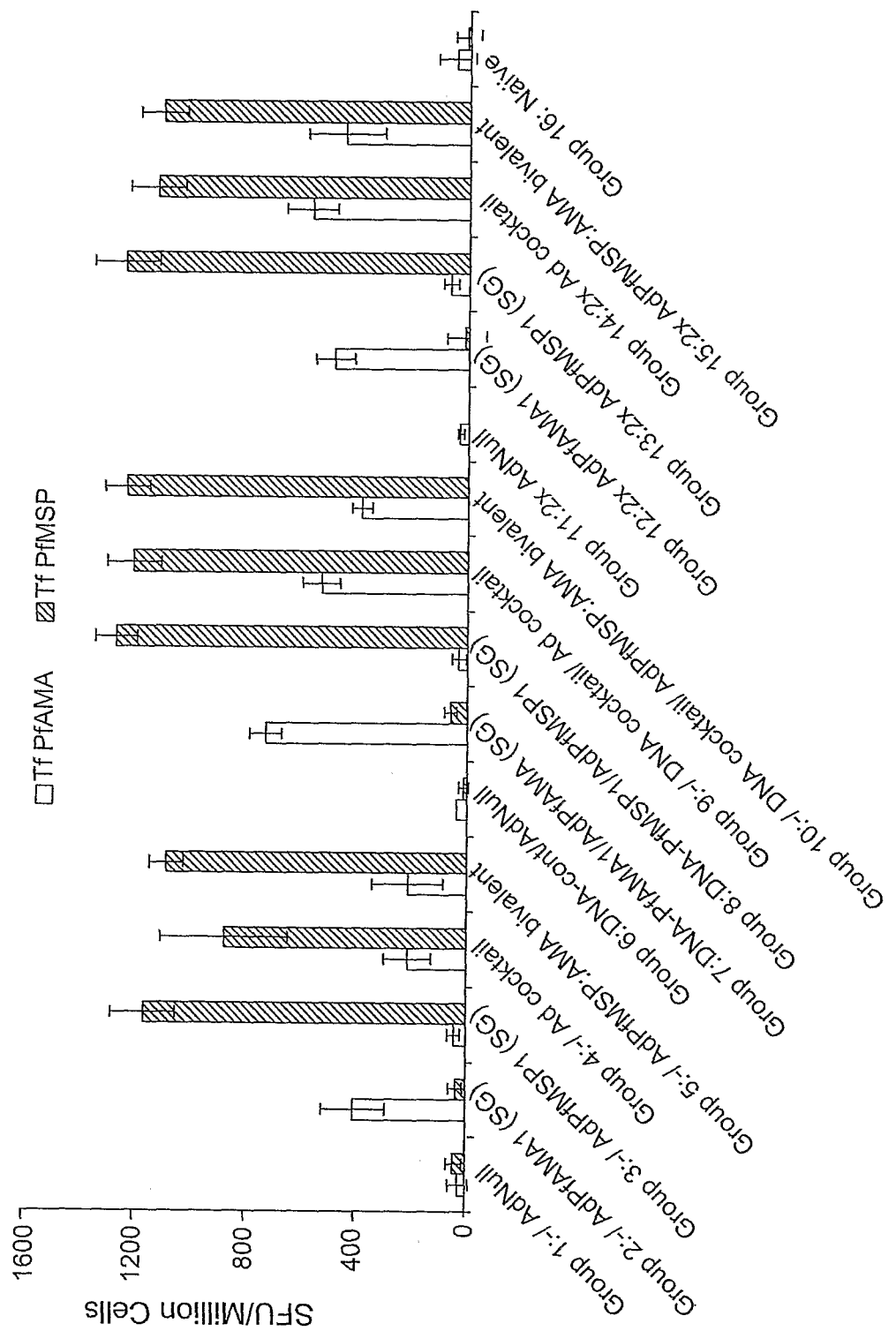
FIG. 1 is a graph depicting the results of an IFN-γ ELIspot assay conducted two weeks after mice were immunized according to the prime-boost regimen set forth in Example 4.

The development of a single vaccine that immunizes a host against multiple antigens of a single pathogen and protects against pathogen challenge (i.e., "multivalent" vaccines) provides a number of advantages over current vaccine methodologies. In particular, multivalent vaccines induce more potent and broad host responses against a given pathogen, and are a more cost-effective alternative to the preparation and administration of multiple vaccines that target a single pathogen. Thus, the invention provides multivalent adenoviral vector-based vaccines directed against malaria. In this respect, the invention provides an adenoviral vector comprising an adenoviral genome comprising three or more heterologous antigen-encoding nucleic acid sequences, wherein the three or more nucleic acid sequences are operably linked to at least two different promoters. The invention also provides an adenoviral vector comprising an adenoviral genome comprising two or more nucleic acid sequences, wherein each nucleic acid sequence encodes a *Plasmodium* antigen and is operably linked to at least one promoter.

Adenovirus (Ad) is a 36 kb double-stranded DNA virus that efficiently transfers DNA in vivo to a variety of different target cell types. For use in the invention, the adenovirus is preferably made replication-deficient by deleting, in whole or in part, select genes required for viral replication. The expendable E3 region is also frequently deleted to allow additional room for a larger DNA insert. The vector can be produced in high titers and can efficiently transfer DNA to replicating and non-replicating cells. The newly transferred genetic information remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and nucleic acid encoding the Rep protein incorporated into an adenoviral vector enables the adenoviral vector to integrate into a mammalian cell genome. Therefore, AAV-Ad chimeric vectors can be a desirable option for use in the invention.

Adenovirus from various origins, subtypes, or mixture of subtypes can be used as the source of the viral genome for the adenoviral vector. While non-human adenovirus (e.g., simian, avian, canine, ovine, or bovine adenoviruses) can be used to generate the adenoviral vector, a human adenovirus preferably is used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). Preferably, in the context of the invention, the adenoviral vector is of human subgroup C, especially serotype 2 or even more desirably serotype 5. However, non-group C adenoviruses can be used to prepare adenoviral gene transfer vectors for delivery of gene products to host cells. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Application Publications WO 97/12986 and WO 98/53087.

The adenoviral vector can comprise a mixture of subtypes and thereby be a "chimeric" adenoviral vector. A chimeric adenoviral vector can comprise an adenoviral genome that is derived from two or more (e.g., 2, 3, 4, etc.) different adenovirus serotypes. In the context of the invention, a chimeric adenoviral vector can comprise approximately different or equal amounts of the genome of each of the two or more different adenovirus serotypes. When the chimeric adenoviral vector genome is comprised of the genomes of two different adenovirus serotypes, the chimeric adenoviral vector genome preferably comprises no more than about 70% (e.g., no more than about 65%, about 50%, or about 40%) of the genome of one of the adenovirus serotypes, with the remainder of the chimeric adenovirus genome being derived from the genome of the other adenovirus serotype. In one embodiment, the chimeric adenoviral vector can contain an adenoviral genome comprising a portion of a serotype 2 genome and a portion of a serotype 5 genome. For example, nucleotides 1-456 of such an adenoviral vector can be derived from a serotype 2 genome, while the remainder of the adenoviral genome can be derived from a serotype 5 genome.

The adenoviral vector of the invention can be replication-competent. For example, the adenoviral vector can have a mutation (e.g., a deletion, an insertion, or a substitution) in the adenoviral genome that does not inhibit viral replication in host cells. The adenoviral vector also can be conditionally replication-competent. Preferably, however, the adenoviral vector is replication-deficient in host cells.

By "replication-deficient" is meant that the adenoviral vector requires complementation of one or more regions of the adenoviral genome that are required for replication, as a result of, for example, a deficiency in at least one replication-essential gene function (i.e., such that the adenoviral vector does not replicate in typical host cells, especially those in a human patient that could be infected by the adenoviral vector in the course of the inventive method). A deficiency in a gene, gene function, gene, or genomic region, as used herein, is defined as a mutation or deletion of sufficient genetic material of the viral genome to obliterate or impair the function of the gene (e.g., such that the function of the gene product is reduced by at least about 2-fold, 5-fold, 10-fold, 20-fold, 30-fold, or 50-fold) whose nucleic acid sequence was mutated or deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2).

The replication-deficient adenoviral vector desirably requires complementation of at least one replication-essential gene function of one or more regions of the adenoviral genome for viral replication. Preferably, the adenoviral vector requires complementation of at least one gene function of the E1A region, the E1B region, or the E4 region of the adenoviral genome required for viral replication (denoted an E1-deficient or E4-deficient adenoviral vector). In addition to a deficiency in the E1 region, the recombinant adenovirus also can have a mutation in the major late promoter (MLP), as discussed in International Patent Application Publication WO 00/00628. Most preferably, the adenoviral vector is deficient in at least one replication-essential gene function (desirably all replication-essential gene functions) of the E1 region and at least one gene function of the nonessential E3 region (e.g., an Xba I deletion of the E3 region) (denoted an E1/E3-deficient adenoviral vector). With respect to the E1 region, the adenoviral vector can be deficient in part or all of the E1A region and/or part or all of the E1B region, e.g., in at least one replication-essential gene function of each of the E1A and E1B regions, thus requiring complementation of the E1A region and the E1B region of the adenoviral genome for replication. The adenoviral vector also can require complementation of the E4 region of the adenoviral genome for replication, such as through a deficiency in one or more replication-essential gene functions of the E4 region.

When the adenoviral vector is E1-deficient, the adenoviral vector genome can comprise a deletion beginning at any nucleotide between nucleotides 335 to 375 (e.g., nucleotide 356) and ending at any nucleotide between nucleotides 3,310 to 3,350 (e.g., nucleotide 3,329) or even ending at any nucleotide between 3,490 and 3,530 (e.g., nucleotide 3,510) (based on the adenovirus serotype 5 genome). When E2A-deficient, the adenoviral vector genome can comprise a deletion beginning at any nucleotide between nucleotides 22,425 to 22,465 (e.g., nucleotide 22,443) and ending at any nucleotide between nucleotides 24,010 to 24,050 (e.g., nucleotide 24,032) (based on the adenovirus serotype 5 genome). When E3-deficient, the adenoviral vector genome can comprise a deletion beginning at any nucleotide between nucleotides 28,575 to 29,615 (e.g., nucleotide 28,593) and ending at any nucleotide between nucleotides 30,450 to 30,490 (e.g., nucleotide 30,470) (based on the adenovirus serotype 5 genome). When E4-deficient, the adenoviral vector genome can comprise a deletion beginning at, for example, any nucleotide between nucleotides 32,805 to 32,845 (e.g., nucleotide 32,826) and ending at, for example, any nucleotide between nucleotides 35,540 to 35,580 (e.g., nucleotide 35,561) (based on the adenovirus serotype 5 genome). The endpoints defining the deleted nucleotide portions can be difficult to precisely determine and typically will not significantly affect the nature of the adenoviral vector, i.e., each of the aforementioned nucleotide numbers can be +/−1, 2, 3, 4, 5, or even 10 or 20 nucleotides.

When the adenoviral vector is deficient in at least one replication-essential gene function in one region of the adenoviral genome (e.g., an E1- or E1/E3-deficient adenoviral vector), the adenoviral vector is referred to as "singly replication-deficient." A particularly preferred singly replication-deficient adenoviral vector is, for example, a replication-deficient adenoviral vector requiring, at most, complementation of the E1 region of the adenoviral genome, so as to propagate the adenoviral vector (e.g., to form adenoviral vector particles).

The adenoviral vector can be "multiply replication-deficient," meaning that the adenoviral vector is deficient in one or more replication-essential gene functions in each of two or more regions of the adenoviral genome, and requires complementation of those functions for replication. For example, the aforementioned E1-deficient or E1/E3-deficient adenoviral vector can be further deficient in at least one replication-essential gene function of the E4 region (denoted an E1/E4- or E1/E3/E4-deficient adenoviral vector), and/or the E2 region (denoted an E1/E2- or E1/E2/E3-deficient adenoviral vector), preferably the E2A region (denoted an E1/E2A- or E1/E2A/E3-deficient adenoviral vector). When the adenoviral vector is multiply replication-deficient, the deficiencies can be a combination of the nucleotide deletions discussed above with respect to each individual region.

If the adenoviral vector of the invention is deficient in a replication-essential gene function of the E2A region, the vector preferably does not comprise a complete deletion of the E2A region, which deletion preferably is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology*, 196: 269-281 (1993)). While deletions in the E2A region coding for the Ct region of the DBP have no effect on viral replication, deletions in the E2A region which code for amino acids 2 to 38 of the Nt domain of the DBP impair viral replication. It is preferable that any multiply replication-deficient adenoviral vector contains this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral serotype 5 genome. This portion of the adenoviral genome desirably is included in the adenoviral vector because it is not complemented in current E2A complementing cell lines so as to provide the desired level of viral propagation.

While the above-described deletions are described with respect to an adenovirus serotype 5 genome, one of ordinary skill in the art can determine the nucleotide coordinates of the same regions of other adenovirus serotypes, such as an adenovirus serotype 2 genome, without undue experimentation, based on the similarity between the genomes of various adenovirus serotypes, particularly adenovirus serotypes 2 and 5.

In one embodiment of the invention, the adenoviral vector can comprise an adenoviral genome deficient in one or more replication-essential gene functions of each of the E1 and E4 regions (i.e., the adenoviral vector is an E1/E4-deficient adenoviral vector), preferably with the entire coding region of the E4 region having been deleted from the adenoviral genome. In other words, all the open reading frames (ORFs) of the E4 region have been removed. Most preferably, the adenoviral vector is rendered replication-deficient by deletion of all of the E1 region and by deletion of a portion of the E4 region. The E4 region of the adenoviral vector can retain the native E4 promoter, polyadenylation sequence, and/or the right-side inverted terminal repeat (ITR).

It should be appreciated that the deletion of different regions of the adenoviral vector can alter the immune response of the mammal. In particular, deletion of different regions can reduce the inflammatory response generated by the adenoviral vector. An adenoviral vector deleted of the entire E4 region can elicit a lower host immune response. Furthermore, the adenoviral vector's coat protein can be modified so as to decrease the adenoviral vector's ability or inability to be recognized by a neutralizing antibody directed against the wild-type coat protein, as described in International Patent Application WO 98/40509. Such modifications are useful for long-term treatment of persistent disorders.

The adenoviral vector, when multiply replication-deficient, especially in replication-essential gene functions of the E1 and E4 regions, can include a spacer sequence to provide viral growth in a complementing cell line similar to that achieved by singly replication-deficient adenoviral vectors, particularly an E1-deficient adenoviral vector. In a preferred E4-deficient adenoviral vector of the invention wherein the L5 fiber region is retained, the spacer is desirably located between the L5 fiber region and the right-side ITR. More preferably in such an adenoviral vector, the E4 polyadenylation sequence alone or, most preferably, in combination with another sequence exists between the L5 fiber region and the right-side ITR, so as to sufficiently separate the retained L5 fiber region from the right-side ITR, such that viral production of such a vector approaches that of a singly replication-deficient adenoviral vector, particularly a singly replication-deficient E1 deficient adenoviral vector.

The spacer sequence can contain any nucleotide sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer sequence can be coding or non-coding and native or non-native with respect to the adenoviral genome, but does not restore the replication-essential function to the deficient region. The spacer can also contain a promoter-variable expression cassette. More preferably, the spacer comprises an additional polyadenylation sequence and/or a passenger gene. Preferably, in the case of a spacer inserted into a region deficient for E4, both the E4 polyadenylation sequence and the E4 promoter of the adenoviral genome or any other (cellular or viral) promoter remain in the vector. The spacer is located between the E4 polyadenylation site and the E4 promoter, or, if the E4 promoter is not present in the vector, the spacer is proximal to the right-side ITR. The spacer can comprise any suitable polyadenylation sequence. Examples of suitable polyadenylation sequences include synthetic optimized sequences, BGH (Bovine Growth Hormone), polyoma virus, TK (Thymidine Kinase), EBV (Epstein Barr Virus) and the papillomaviruses, including human papillomaviruses and BPV (Bovine Papilloma Virus). Preferably, particularly in the E4 deficient region, the spacer includes an SV40 polyadenylation sequence. The SV40 polyadenylation sequence allows for higher virus production levels of multiply replication deficient adenoviral vectors. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. Ideally, the spacer is composed of the glucuronidase gene. The use of a spacer in an adenoviral vector is further described in, for example, U.S. Pat. No. 5,851,806 and International Patent Application Publication WO 97/21826.

It has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others, as described in for example, U.S. Pat. Nos. 6,225,113, 6,649,373, and 6,660,521, and International Patent Application Publication WO 00/34496. In view of the above, a replication-deficient adenoviral vector (e.g., the at least E4-deficient adenoviral vector) or a second expression vector can comprise a nucleic acid sequence encoding a trans-acting factor that modulates the persistence of expression of the nucleic acid sequence.

Desirably, the adenoviral vector requires, at most, complementation of replication-essential gene functions of the E1, E2A, and/or E4 regions of the adenoviral genome for replication (i.e., propagation). However, the adenoviral genome can be modified to disrupt one or more replication-essential gene functions as desired by the practitioner, so long as the adenoviral vector remains deficient and can be propagated using, for example, complementing cells and/or exogenous DNA (e.g., helper adenovirus) encoding the disrupted replication-essential gene functions. In this respect, the adenoviral vector can be deficient in replication-essential gene functions of only the early regions of the adenoviral genome, only the late regions of the adenoviral genome, both the early and late regions of the adenoviral genome, or all adenoviral genes (i.e., a high capacity adenovector (HC-Ad), see Morsy et al., *Proc. Natl. Acad. Sci. USA*, 95: 965-976 (1998), Chen et al., *Proc. Natl. Acad. Sci. USA*, 94: 1645-1650 (1997), and Kochanek et al., *Hum. Gene Ther.*, 10: 2451-2459 (1999)). Suitable replication-deficient adenoviral vectors, including singly and multiply replication-deficient adenoviral vectors, are disclosed in U.S. Pat. Nos. 5,837,511, 5,851,806, 5,994, 106, 6,127,175, and 6,482,616; U.S. Patent Application Publications 2001/0043922 A1, 2002/0004040 A1, 2002/ 0031831 A1, 2002/0110545 A1, and 2004/0161848 A1; and International Patent Application Publications WO 94/28152, WO 95/02697, WO 95/16772, WO 95/34671, WO 96/22378, WO 97/12986, WO 97/21826, and WO 03/022311.

By removing all or part of, for example, the E1, E3, and E4 regions of the adenoviral genome, the resulting adenoviral vector is able to accept inserts of exogenous nucleic acid sequences while retaining the ability to be packaged into adenoviral capsids. The nucleic acid sequence can be positioned in the E1 region, the E3 region, or the E4 region of the adenoviral genome. Indeed, the nucleic acid sequence can be inserted anywhere in the adenoviral genome so long as the position does not prevent expression of the nucleic acid sequence or interfere with packaging of the adenoviral vector.

Replication-deficient adenoviral vectors are typically produced in complementing cell lines that provide gene functions not present in the replication-deficient adenoviral vectors, but required for viral propagation, at appropriate levels in order to generate high titers of viral vector stock. Desirably, the complementing cell line comprises, integrated into the cellular genome, adenoviral nucleic acid sequences which encode gene functions required for adenoviral propagation. A preferred cell line complements for at least one and preferably all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially vaccination purposes. The lack of RCA in the vector stock avoids the replication of the adenoviral vector in non-complementing cells. Construction of such a complementing cell lines involve standard molecular biology and cell culture techniques, such as those described by Sambrook et al., supra, and Ausubel et al., supra).

Complementing cell lines for producing the adenoviral vector include, but are not limited to, 293 cells (described in, e.g., Graham et al., *J. Gen. Virol.*, 36, 59-72 (1977)), PER.C6 cells (described in, e.g., International Patent Application Publication WO 97/00326, and U.S. Pat. Nos. 5,994,128 and 6,033,908), and 293-ORF6 cells (described in, e.g., International Patent Application Publication WO 95/34671 and Brough et al., *J. Virol.*, 71: 9206-9213 (1997)). Additional complementing cells are described in, for example, U.S. Pat. Nos. 6,677,156 and 6,682,929, and International Patent Application Publication WO 03/20879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the desired adenoviral vector. Helper virus is often engineered to prevent packaging of infectious helper virus. For example, one or more replication-essential gene functions of the E1 region of the adenoviral genome are provided by the complementing cell, while one or more replication-essential gene functions of the E4 region of the adenoviral genome are provided by a helper virus.

If the adenoviral vector is not replication-deficient, ideally the adenoviral vector is manipulated to limit replication of the vector to within a target tissue. The adenoviral vector can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. For example, in autoimmune disease treatment, it can be advantageous to control adenoviral vector replication in, for instance, lymph nodes, to obtain continual antigen production and control immune cell production. Conditionally-replicating adenoviral vectors are described further in U.S. Pat. No. 5,998,205.

In addition to modification (e.g., deletion, mutation, or replacement) of adenoviral sequences encoding replication-essential gene functions, the adenoviral genome can contain benign or non-lethal modifications, i.e., modifications which do not render the adenovirus replication-deficient, or, desirably, do not adversely affect viral functioning and/or production of viral proteins, even if such modifications are in regions of the adenoviral genome that otherwise contain replication-essential gene functions. Such modifications commonly result from DNA manipulation or serve to facilitate expression vector construction. For example, it can be advantageous to remove or introduce restriction enzyme sites in the adenoviral genome. Such benign mutations often have no detectable adverse effect on viral functioning. For example, the adenoviral vector can comprise a deletion of nucleotides 10,594 and 10,595 (based on the adenoviral serotype 5 genome), which are associated with VA-RNA-1 transcription, but the deletion of which does not prohibit production of VA-RNA-1.

Similarly, the coat protein of an adenoviral vector can be manipulated to alter the binding specificity or recognition of a virus for a viral receptor on a potential host cell. For adenovirus, such manipulations can include deletion of regions of the fiber, penton, or hexon, insertions of various native or non-native ligands into portions of the coat protein, and the like. Manipulation of the coat protein can broaden the range of cells infected by the adenoviral vector or enable targeting of the adenoviral vector to a specific cell type.

Any suitable technique for altering native binding to a host cell, such as native binding of the fiber protein to the coxsackievirus and adenovirus receptor (CAR) of a cell, can be employed. For example, differing fiber lengths can be exploited to ablate native binding to cells. This optionally can be accomplished via the addition of a binding sequence to the penton base or fiber knob. This addition of a binding sequence can be done either directly or indirectly via a bispecific or multispecific binding sequence. In an alternative embodiment, the adenoviral fiber protein can be modified to reduce the number of amino acids in the fiber shaft, thereby creating a "short-shafted" fiber (as described in, for example, U.S. Pat. No. 5,962,311). Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber enables targeting of the adenovirus to a desired cell-surface receptor by the introduction of a normative amino acid sequence either into the penton base or the fiber knob.

In yet another embodiment, the nucleic acid residues encoding amino acid residues associated with native substrate binding can be changed, supplemented, or deleted (see, e.g., International Patent Application Publication WO 00/15823, Einfeld et al., *J. Virol.*, 75(23): 11284-11291 (2001), and van Beusechem et al., *J. Virol.*, 76(6): 2753-2762 (2002)) such that the adenoviral vector incorporating the mutated nucleic acid residues (or having the fiber protein encoded thereby) is less able to bind its native substrate. In this respect, the native CAR and integrin binding sites of the adenoviral vector, such as the knob domain of the adenoviral fiber protein and an Arg-Gly-Asp (RGD) sequence located in the adenoviral penton base, respectively, can be removed or disrupted. Any suitable amino acid residue(s) of a fiber protein that mediates or assists in the interaction between the knob and CAR can be mutated or removed, so long as the fiber protein is able to trimerize. Similarly, amino acids can be added to the fiber knob as long as the fiber protein retains the ability to trimerize. Suitable residues include amino acids within the exposed loops of the serotype 5 fiber knob domain, such as, for example, the AB loop, the DE loop, the FG loop, and the HI loop, which are further described in, for example, Roelvink et al., *Science*, 286: 1568-1571 (1999), and U.S. Pat. No. 6,455, 314. Any suitable amino acid residue(s) of a penton base protein that mediates or assists in the interaction between the penton base and integrins can be mutated or removed. Suitable residues include, for example, one or more of the five RGD amino acid sequence motifs located in the hypervariable region of the Ad5 penton base protein (as described, for example, U.S. Pat. No. 5,731,190). The native integrin binding sites on the penton base protein also can be disrupted by modifying the nucleic acid sequence encoding the native RGD motif such that the native RGD amino acid sequence is conformationally inaccessible for binding to the $\alpha v$ integrin receptor, such as by inserting a DNA sequence into or adjacent to the nucleic acid sequence encoding the adenoviral penton base protein. Preferably, the adenoviral vector comprises a fiber protein and a penton base protein that do not bind to CAR and integrins, respectively. Alternatively, the adenoviral vector comprises fiber protein and a penton base protein that bind to CAR and integrins, respectively, but with less affinity than the corresponding wild type coat proteins. The adenoviral vector exhibits reduced binding to CAR and integrins if a modified adenoviral fiber protein and penton base protein binds CAR and integrins, respectively, with at least about 5-fold, 10-fold, 20-fold, 30-fold, 50-fold, or 100-fold less affinity than a non-modified adenoviral fiber protein and penton base protein of the same serotype.

The adenoviral vector also can comprise a chimeric coat protein comprising a non-native amino acid sequence that binds a substrate (i.e., a ligand), such as a cellular receptor other than CAR the $\alpha v$ integrin receptor. Such a chimeric coat protein allows an adenoviral vector to bind, and desirably, infect host cells not naturally infected by the corresponding adenovirus that retains the ability to bind native cell surface receptors, thereby further expanding the repertoire of cell types infected by the adenoviral vector. The non-native amino acid sequence of the chimeric adenoviral coat protein allows an adenoviral vector comprising the chimeric coat protein to bind and, desirably, infect host cells not naturally infected by a corresponding adenovirus without the non-native amino acid sequence (i.e., host cells not infected by the corresponding wild-type adenovirus), to bind to host cells naturally infected by the corresponding adenovirus with greater affinity than the corresponding adenovirus without the non-native amino acid sequence, or to bind to particular target cells with greater affinity than non-target cells. A "non-native" amino acid sequence can comprise an amino acid sequence not naturally present in the adenoviral coat protein or an amino acid sequence found in the adenoviral coat but located in a non-native position within the capsid. By "preferentially binds" is meant that the non-native amino acid sequence binds a receptor, such as, for instance, $\alpha v \beta 3$ integrin, with at least about 3-fold greater affinity (e.g., at least about 5-fold, 10-fold, 15-fold, 20-fold, 25-fold, 35-fold, 45-fold, or 50-fold greater affinity) than the non-native ligand binds a different receptor, such as, for instance, $\alpha v \beta 1$ integrin.

Desirably, the adenoviral vector comprises a chimeric coat protein comprising a non-native amino acid sequence that confers to the chimeric coat protein the ability to bind to an immune cell more efficiently than a wild-type adenoviral coat protein. In particular, the adenoviral vector can comprise a chimeric adenoviral fiber protein comprising a non-native amino acid sequence which facilitates uptake of the adenoviral vector by immune cells, preferably antigen presenting cells, such as dendritic cells, monocytes, and macrophages. In a preferred embodiment, the adenoviral vector comprises a chimeric fiber protein comprising an amino acid sequence (e.g., a non-native amino acid sequence) comprising an RGD motif including, but not limited to, CRGDC (SEQ ID NO: 1), CXCRGDCXC (SEQ ID NO: 2), wherein X represents any amino acid, and CDCRGDCFC (SEQ ID NO: 3), which increases transduction efficiency of an adenoviral vector into dendritic cells. The RGD-motif, or any non-native amino acid sequence, preferably is inserted into the adenoviral fiber knob region, ideally in an exposed loop of the adenoviral knob, such as the HI loop. A non-native amino acid sequence also can be appended to the C-terminus of the adenoviral fiber protein, optionally via a spacer sequence. The spacer sequence preferably comprises between one and two-hundred amino acids, and can (but need not) have an intended function.

Where dendritic cells are the desired target cell, the non-native amino acid sequence can optionally recognize a protein typically found on dendritic cell surfaces such as adhesion proteins, chemokine receptors, complement receptors, co-stimulation proteins, cytokine receptors, high level antigen presenting molecules, homing proteins, marker proteins, receptors for antigen uptake, signaling proteins, virus receptors, etc. Examples of such potential ligand-binding sites in dendritic cells include αvβ3 integrins, αvβ5 integrins, 2A1, 7-TM receptors, CD1, CD11a, CD11b, CD11c, CD21, CD24, CD32, CD4, CD40, CD44 variants, CD46, CD49d, CD50, CD54, CD58, CD64, ASGPR, CD80, CD83, CD86, E-cadherin, integrins, M342, MHC-I, MHC-II, MIDC-8, MMR, OX62, p200-MR6, p55, S100, TNF-R, etc. Where dendritic cells are targeted, the ligand preferably recognizes the CD40 cell surface protein, such as, for example, by way of a CD-40 (bi)specific antibody fragment or by way of a domain derived from the CD40L polypeptide.

Where macrophages are the desired target, the non-native amino acid sequence optionally can recognize a protein typically found on macrophage cell surfaces, such as phosphatidylserine receptors, vitronectin receptors, integrins, adhesion receptors, receptors involved in signal transduction and/or inflammation, markers, receptors for induction of cytokines, or receptors up-regulated upon challenge by pathogens, members of the group B scavenger receptor cysteine-rich (SRCR) superfamily, sialic acid binding receptors, members of the Fc receptor family, B7-1 and B7-2 surface molecules, lymphocyte receptors, leukocyte receptors, antigen presenting molecules, and the like. Examples of suitable macrophage surface target proteins include, but are not limited to, heparin sulfate proteoglycans, αvβ3 integrins, αvβ5 integrins, B7-1, B7-2, CD11c, CD13, CD16, CD163, CD1a, CD22, CD23, CD29, Cd32, CD33, CD36, CD44, CD45, CD49e, CD52, CD53, CD54, CD71, CD87, CD9, CD98, Ig receptors, Fc receptor proteins (e.g., subtypes of Fcα, Fcγ, Fcε, etc.), folate receptor b, HLA Class I, Sialoadhesin, siglec-5, and the toll-like receptor-2 (TLR2).

Where B-cells are the desired target, the non-native amino acid sequence can recognize a protein typically found on B-cell surfaces, such as integrins and other adhesion molecules, complement receptors, interleukin receptors, phagocyte receptors, immunoglobulin receptors, activation markers, transferrin receptors, members of the scavenger receptor cysteine-rich (SRCR) superfamily, growth factor receptors, selectins, MHC molecules, TNF-receptors, and TNF-R associated factors. Examples of typical B-cell surface proteins include β-glycan, B cell antigen receptor (BAC), B7-2, B-cell receptor (BCR), C3d receptor, CD1, CD18, CD19, CD20, CD21, CD22, CD23, CD35, CD40, CD5, CD6, CD69, CD69, CD71, CD79a/CD79b dimer, CD95, endoglin, Fas antigen, human Ig receptors, Fc receptor proteins (e.g., subtypes of Fcα, Fcγ, Fcε, etc.), IgM, gp200-MR6, Growth Hormone Receptor (GH-R), ICAM-1, ILT2, CD85, MHC class I and II molecules, transforming growth factor receptor (TGF-R), α4β7 integrin, and αvβ3 integrin.

In another embodiment, the adenoviral vector can comprise a chimeric virus coat protein that is not selective for a specific type of eukaryotic cell. The chimeric coat protein differs from a wild-type coat protein by an insertion of a non-native amino acid sequence into or in place of an internal coat protein sequence, or attachment of a non-native amino acid sequence to the N- or C-terminus of the coat protein. For example, a ligand comprising about five to about nine lysine residues (preferably seven lysine residues) is attached to the C-terminus of the adenoviral fiber protein via a non-functional spacer sequence. In this embodiment, the chimeric virus coat protein efficiently binds to a broader range of eukaryotic cells than a wild-type virus coat, such as described in U.S. Pat. No. 6,465,253 and International Patent Application Publication WO 97/20051. Such an adenoviral vector can ensure widespread production of the antigen.

The ability of an adenoviral vector to recognize a potential host cell can be modulated without genetic manipulation of the coat protein, i.e., through use of a bi-specific molecule. For instance, complexing an adenovirus with a bispecific molecule comprising a penton base-binding domain and a domain that selectively binds a particular cell surface binding site enables the targeting of the adenoviral vector to a particular cell type. Likewise, an antigen can be conjugated to the surface of the adenoviral particle through non-genetic means.

A non-native amino acid sequence can be conjugated to any of the adenoviral coat proteins to form a chimeric adenoviral coat protein. Therefore, for example, a non-native amino acid sequence can be conjugated to, inserted into, or attached to a fiber protein, a penton base protein, a hexon protein, proteins IX, VI, or IIIa, etc. The sequences of such proteins, and methods for employing them in recombinant proteins, are well known in the art (see, e.g., U.S. Pat. Nos. 5,543,328; 5,559,099; 5,712,136; 5,731,190; 5,756,086; 5,770,442; 5,846,782; 5,962,311; 5,965,541; 5,846,782; 6,057,155; 6,127,525; 6,153,435; 6,329,190; 6,455,314; 6,465,253; 6,576,456; 6,649,407; 6,740,525, and International Patent Application Publications WO 96/07734, WO 96/26281, WO 97/20051, WO 98/07877, WO 98/07865, WO 98/40509, WO 98/54346, WO 00/15823, WO 01/58940, and WO 01/92549). The chimeric adenoviral coat protein can be generated using standard recombinant DNA techniques known in the art. Preferably, the nucleic acid sequence encoding the chimeric adenoviral coat protein is located within the adenoviral genome and is operably linked to a promoter that regulates expression of the coat protein in a wild-type adenovirus. Alternatively, the nucleic acid sequence encoding the chimeric adenoviral coat protein is located within the adenoviral genome and is part of an expression cassette which comprises genetic elements required for efficient expression of the chimeric coat protein.

The coat protein portion of the chimeric adenovirus coat protein can be a full-length adenoviral coat protein to which the ligand domain is appended, or it can be truncated, e.g., internally or at the C- and/or N-terminus. However modified (including the presence of the non-native amino acid), the chimeric coat protein preferably is able to incorporate into an adenoviral capsid. Where the non-native amino acid sequence is attached to the fiber protein, preferably it does not disturb the interaction between viral proteins or fiber monomers.

Thus, the non-native amino acid sequence preferably is not itself an oligomerization domain, as such can adversely interact with the trimerization domain of the adenovirus fiber. Preferably the non-native amino acid sequence is added to the virion protein, and is incorporated in such a manner as to be readily exposed to a substrate, cell surface-receptor, or immune cell (e.g., at the N- or C-terminus of the adenoviral protein, attached to a residue facing a substrate, positioned on a peptide spacer, etc.) to maximally expose the non-native amino acid sequence. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate, cell surface receptor, or immune cell. Where the non-native amino acid sequence is attached to the hexon, preferably it is within a hypervariable region (Miksza et al., *J. Virol.*, 70(3): 1836-44 (1996)). Where the non-native amino acid is attached to or replaces a portion of pIX, preferably it is within the C-terminus of pIX. Use of a spacer sequence to extend the non-native amino acid sequence away from the surface of the adenoviral particle can be advantageous in that the non-native amino acid sequence can be more available for binding to a receptor, and any steric interactions between the non-native amino acid sequence and the adenoviral fiber monomers can be reduced.

Binding affinity of a non-native amino acid sequence to a cellular receptor can be determined by any suitable assay, a variety of which assays are known and are useful in selecting a non-native amino acid sequence for incorporating into an adenoviral coat protein. Desirably, the transduction levels of host cells are utilized in determining relative binding efficiency. Thus, for example, host cells displaying αvβ3 integrin on the cell surface (e.g., MDAMB435 cells) can be exposed to an adenoviral vector comprising the chimeric coat protein and the corresponding adenovirus without the non-native amino acid sequence, and then transduction efficiencies can be compared to determine relative binding affinity. Similarly, both host cells displaying αvβ3 integrin on the cell surface (e.g., MDAMB435 cells) and host cells displaying predominantly αvβ1 on the cell surface (e.g., 293 cells) can be exposed to the adenoviral vectors comprising the chimeric coat protein, and then transduction efficiencies can be compared to determine binding affinity.

In other embodiments (e.g., to facilitate purification or propagation within a specific engineered cell type), a non-native amino acid (e.g., ligand) can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J. Cell. Biol.*, 130: 1189 (1995)). A ligand can even bind non-peptide substrates, such as plastic (e.g., Adey et al., *Gene*, 156: 27 (1995)), biotin (Saggio et al., *Biochem. J.*, 293: 613 (1993)), a DNA sequence (Cheng et al., *Gene*, 171: 1 (1996), and Krook et al., *Biochem. Biophys., Res. Commun.*, 204: 849 (1994)), streptavidin (Geibel et al., *Biochemistry*, 34: 15430 (1995), and Katz, *Biochemistry*, 34: 15421 (1995)), nitrostreptavidin (Balass et al., *Anal. Biochem.*, 243: 264 (1996)), heparin (Wickham et al., *Nature Biotechnol.*, 14: 1570-73 (1996)), and other substrates.

Disruption of native binding of adenoviral coat proteins to a cell surface receptor can also render it less able to interact with the innate or acquired host immune system. Aside from pre-existing immunity, adenoviral vector administration induces inflammation and activates both innate and acquired immune mechanisms. Adenoviral vectors activate antigen-specific (e.g., T-cell dependent) immune responses, which limit the duration of transgene expression following an initial administration of the vector. In addition, exposure to adenoviral vectors stimulates production of neutralizing antibodies by B cells, which can preclude gene expression from subsequent doses of adenoviral vector (Wilson & Kay, *Nat. Med.*, 3(9): 887-889 (1995)). Indeed, the effectiveness of repeated administration of the vector can be severely limited by host immunity. In addition to stimulation of humoral immunity, cell-mediated immune functions are responsible for clearance of the virus from the body. Rapid clearance of the virus is attributed to innate immune mechanisms (see, e.g., Worgall et al., *Human Gene Therapy*, 8: 37-44 (1997)), and likely involves Kupffer cells found within the liver. Thus, by ablating native binding of an adenovirus fiber protein and penton base protein, immune system recognition of an adenoviral vector is diminished, thereby increasing vector tolerance by the host.

Another method for evading pre-existing host immunity to adenovirus, especially serotype 5 adenovirus, involves modifying an adenoviral coat protein such that it exhibits reduced recognition by the host immune system. Thus, the inventive adenoviral vectors preferably comprise such a modified coat protein. The modified coat protein preferably is a penton, fiber, or hexon protein. Most preferably, the modified coat protein is a hexon protein. The coat protein can be modified in any suitable manner, but is preferably modified by generating diversity in the coat protein. Preferably, such coat protein variants are not recognized by pre-existing host (e.g., human) adenovirus-specific neutralizing antibodies. Diversity can be generated using any suitable method known in the art, including, for example, directed evolution (i.e., polynucleotide shuffling) and error-prone PCR (see, e.g., Cadwell, *PCR Meth. Appl.*, 2: 28-33 (1991), Leung et al., *Technique*, 1: 11-15 (1989), and Pritchard et al., *J. Theoretical Biol.*, 234: 497-509 (2005)). Preferably, coat protein diversity is generated through directed evolution techniques, such as those described in, e.g., Stemmer, *Nature*, 370: 389-91 (1994), Chemy et al., *Nat. Biotechnol.*, 17: 379-84 (1999), and Schmidt-Dannert et al., *Nat. Biotechnol.*, 18(7): 750-53 (2000). In general, directed evolution involves three repeated operations: mutation, selection, and amplification. The primary steps performed in directed evolution typically include (1) mutation or recombination of a gene of interest, (2) construction of a library of the mutated or recombined genes, (3) expression of the library in suitable host cells, (4) selection of cells that express a variant with a desired function or activity, and (5) isolation of a gene encoding a desired variant. This process is repeated until the desired number of variants is produced.

In the context of the invention, coat protein diversity is generated by first making random mutations in the gene encoding the coat protein by, for example, polynucleotide shuffling or error-prone PCR. The mutated coat protein genes are incorporated into a library of E1-deficient Ad5 adenoviral vectors, wherein each Ad5 vector comprises an Ad35 fiber protein and a dual expression cassette which expresses two marker genes (e.g., luciferase and green fluorescent protein) inserted into the E1 region. Library vectors are propagated in suitable host cells (e.g., *E. coli*), and vectors encoding potential coat protein variants of interest are rescued under competitive conditions in the presence of human anti-Ad5 neutralizing antibodies. Rescued vectors are either expanded in the presence of anti-Ad5 neutralizing antibodies, purified, or cloned, and coat protein variants are subjected to nucleic acid sequencing.

Once identified, the biological activity of the proteins encoded by the coat protein variants produced by the above strategy must be screened. Any suitable assay for measuring the desired biological activity of a coat protein variant can be used. For example, the importance of evaluating the growth properties of an Ad5 vector comprising a variant coat protein will be readily apparent to one of ordinary skill in the art. In addition, the immunogenicity of Ad5 vectors comprising a variant coat protein and encoding a heterologous antigen (e.g., a *Plasmodium* antigen) can be compared to a similar Ad5 vector comprising a wild-type coat protein. Moreover, because the ideal coat protein variant is not recognized by pre-existing adenovirus-specific neutralizing antibodies, it is necessary to evaluate the potential neutralizing effects of human serum on the coat protein variants.

An adenoviral coat protein also can be modified to evade pre-existing host immunity by deleting a region of a coat protein and replacing it with a corresponding region from the coat protein of another adenovirus serotype, particularly a serotype which is less immunogenic in humans. In this regard, amino acid sequences within the fiber protein, the penton base protein, and/or the hexon protein can be removed and replaced with corresponding sequences from a different adenovirus serotype. As discussed above, a preferred adenovirus serotype for use in the invention is serotype 5. Thus, for example, when the fiber protein is modified to evade pre-existing host immunity, amino acid residues from the knob region of a serotype 5 fiber protein can be deleted and replaced with corresponding amino acid residues from an adenovirus of a different serotype, such as those serotypes described herein. Likewise, when the penton base protein is modified to evade pre-existing host immunity, amino acid residues within the hypervariable region of a serotype 5 penton base protein can be deleted and replaced with corresponding amino acid residues from an adenovirus of a different serotype, such as those serotypes described herein. Preferably, the hexon protein of the adenoviral vector is modified in this manner to evade pre-existing host immunity. In this respect, when the adenoviral vector is of serotype 5, amino acid residues within one or more of the hypervariable regions, which occur in loops of the hexon protein, are removed and replaced with corresponding amino acid residues from an adenovirus of a different serotype. Preferably, amino acid residues within the FG1, FG2, or DE1 loops of a serotype 5 hexon protein are deleted and replaced with corresponding amino acid residues from a hexon protein of a different adenovirus serotype. An entire loop region can be removed from the serotype 5 hexon protein and replaced with the corresponding loop region of another adenovirus serotype. Alternatively, portions of a loop region can be removed from the serotype 5 hexon protein and replaced with the corresponding portion of a hexon loop of another adenovirus serotype. One or more hexon loops, or portions thereof, of a serotype 5 adenoviral vector can be removed and replaced with the corresponding sequences from any other adenovirus serotype, such as those described herein. Preferably, one or more hexon loops, or portions thereof, of an Ad5 vector are removed and replaced with corresponding amino acid sequences from an adenovirus of serotype 2, 34, or 43. The structure of Ad2 and Ad5 hexon proteins and methods of modifying hexon proteins are disclosed in, for example, Rux et al., *J. Virol.*, 77: 9553-9566 (2003), and U.S. Pat. No. 6,127,525. The hypervariable regions of a hexon protein also can be replaced with random peptide sequences, or peptide sequences derived from a disease-causing pathogen (e.g., *Plasmodium falciparum*).

Suitable modifications to an adenoviral vector are described in U.S. Pat. Nos. 5,543,328; 5,559,099; 5,712,136; 5,731,190; 5,756,086; 5,770,442; 5,846,782; 5,871,727; 5,885,808; 5,922,315; 5,962,311; 5,965,541; 6,057,155; 6,127,525; 6,153,435; 6,329,190; 6,455,314; 6,465,253; 6,576,456; 6,649,407; and 6,740,525; U.S. Patent Application Publications 2001/0047081 A1, 2002/0099024 A1, 2002/0151027 A1, 2003/0022355 A1, and 2003/0099619 A1, and International Patent Applications WO 96/07734, WO 96/26281, WO 97/20051, WO 98/07865, WO 98/07877, WO 98/40509, WO 98/54346, WO 00/15823, WO 01/58940, and WO 01/92549.

In one embodiment of the invention, the adenoviral vector comprises three or more heterologous nucleic acid sequences. A "heterologous nucleic acid sequence" is any nucleic acid sequence that is not obtained from, derived from, or based upon a naturally occurring nucleic acid sequence of the adenoviral vector. By "naturally occurring" is meant that the nucleic acid sequence can be found in nature and has not been synthetically modified. For example, the heterologous nucleic acid sequence can be a viral, bacterial, plant, or animal nucleic acid sequence. A sequence is "obtained" from a source when it is isolated from that source. A sequence is "derived" from a source when it is isolated from a source but modified in any suitable manner (e.g., by deletion, substitution (mutation), insertion, or other modification to the sequence) so as not to disrupt the normal function of the source gene. A sequence is "based upon" a source when the sequence is a sequence more than about 70% identical (preferably more than about 80% identical, more preferably more than about 90% identical, and most preferably more than about 95% identical) to the source but obtained through synthetic procedures (e.g., polynucleotide synthesis, directed evolution, etc.). Determining the degree of identity, including the possibility for gaps, can be accomplished using any suitable method (e.g., BLASTnr, provided by GenBank). Notwithstanding the foregoing, the heterologous nucleic acid sequence can be naturally found in the adenoviral vector, but located at a normative position within the adenoviral genome and/or operably linked to a normative promoter. While the adenoviral vector can comprise three or more heterologous nucleic acids sequences (e.g., 3, 4, 5, 6, 7, 8, 9, 10 or more heterologous nucleic acid sequences), the adenoviral vector preferably comprises three heterologous nucleic acid sequences.

Any type of nucleic acid sequence (e.g., DNA, RNA, and cDNA) that can be inserted into an adenoviral vector can be used in connection with the invention. Preferably, each heterologous nucleic acid sequence is DNA, and preferably encodes a protein (i.e., one or more nucleic acid sequences encoding one or more proteins). In a particularly preferred embodiment, each of the three or more heterologous nucleic acid sequences encodes an antigen. An "antigen" is a molecule that induces an immune response in a mammal. An "immune response" can entail, for example, antibody production and/or the activation of immune effector cells (e.g., T cells). An antigen in the context of the invention can comprise any subunit, fragment, or epitope of any proteinaceous molecule, including a protein or peptide of viral, bacterial, parasitic, fungal, protozoan, prion, cellular, or extracellular origin, which ideally provokes an immune response in mammal, preferably leading to protective immunity. By "epitope" is meant a sequence on an antigen that is recognized by an antibody or an antigen receptor. Epitopes also are referred to in the art as "antigenic determinants."

In one embodiment, the antigen is a tumor antigen. By "tumor antigen" is meant an antigen that is expressed by tumor cells but not normal cells, or an antigen that is expressed in normal cells but is overexpressed in tumor cells. Examples of suitable tumor antigens include, but are not limited to, β-catenin, BCR-ABL fusion protein, K-ras, N-ras, PTPRK, NY-ESO-1/LAGE-2, SSX-2, TRP2-INT2, CEA, gp100, kallikrein 4, prostate specific antigen (PSA), TRP-1/gp75, TRP-2, tyrosinase, EphA3, HER-2/neu, MUC1, p53, mdm-2, PSMA, RAGE-1, surviving, telomerase, and WT1. Other tumor antigens are known in the art and are described in, for example, The Peptide Database of T-Cell Defined Tumor Antigens, maintained by the Ludwig Institute for Cancer Research (http://www.cancerimmunity.org/statics/databases.htm), Van den Eynde et al., *Curr. Opin. Immunol.*, 9: 684-93 (1997), Houghton et al., *Curr. Opin. Immunol.*, 13: 134-140 (2001), and van der Bruggen et al., *Immunol. Rev.*, 188: 51-64 (2002).

In another embodiment, the antigen can be a viral antigen. The viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae (e.g., Hepatitis B virus), Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxyiridae (e.g., vaccinia virus), Reoviridae (e.g., rotavirus), Retroviridae (e.g., lentivirus, such as human immunodeficiency virus (HIV) 1 and HIV 2), Rhabdoviridae, and Totiviridae. Particularly preferred retroviridae (retrovirus) antigens include, for example, HIV antigens, such as all or part of the gag, env, or pol proteins, or fusion proteins comprising all or part of the gag, env, or pol proteins. Any clade of HIV is appropriate for antigen selection, including clades A, B, C, MN, and the like. Particularly preferred coronavirus antigens include, for example, SARS virus antigens. Suitable SARS virus antigens for the invention include, for example, all or part of the E protein, the M protein, and the spike protein of the SARS virus. Suitable viral antigens also include all or part of Dengue protein M, Dengue protein E, Dengue D1NS1, Dengue D1NS2, and Dengue D1NS3. The antigenic peptides specifically recited herein are merely exemplary as any viral protein can be used in the context of the invention.

Alternatively or in addition, at least one antigen encoded by the adenoviral vector is a bacterial antigen. The antigen can originate from any bacterium including, but not limited to, *Actinomyces, Anabaena, Bacillus, Bacteroides, Bdellovibrio, Caulobacter, Chlamydia, Chlorobium, Chromatium, Clostridium, Cytophaga, Deinococcus, Escherichia, Halobacterium, Heliobacter, Hyphomicrobium, Methanobacterium, Micrococcus, Myobacterium, Mycoplasma, Myxococcus, Neisseria, Nitrobacter, Oscillatoria, Prochloron, Proteus, Pseudomonas, Phodospirilluin, Rickettsia, Salmonella, Shigella, Spirillum, Spirochaeta, Staphylococcus, Streptococcus, Streptomyces, Sulfolobus, Thermoplasma, Thiobacillus,* and *Treponema*.

Desirably, the antigen is a parasite antigen such as, but not limited to, a parasite of the phylum Sporozoa (also referred to as phylum Apicomplexa), Ciliophora, Rhizopoda, or Zoomastigophora. Preferably, the antigen is a parasite of the phylum Sporozoa and genus *Plasmodium*. The antigen can be from any suitable *Plasmodium* species, but preferably is from a *Plasmodium* species that infects humans and causes malaria. Human-infecting *Plasmodium* species include *P. malariae, P. ovale, P. vivax*, and *P. falciparum. P. vivax* and *P. falciparum* are the most common, and *P. falciparum* is the most deadly, species of *Plasmodium* in human. Alternatively, the antigen can be from a species of *Plasmodium* that infects non-human animals. For example, *P. vinckei, P. chabaudi, P. yoelii*, and *P. berghei*. infect rodents, *P. knowlesi, P. cynomolgi, P. simiovale, P. fieldi, P. inui*, and *P. brasilianum* infect non-human primates. *P. gallinaceum* infects birds. In order to advance vaccine discovery, the genomes of a number of *Plasmodium* species have been sequenced. For example, the complete *P. falciparum* genome has been sequenced and is disclosed in Gardner et al., *Nature*, 419: 498-511 (2002). In addition, the complete *P. yoelii* genome sequence is disclosed in Carlton et al., *Nature*, 419: 512-9 (2002). Thus, one of ordinary skill in the art can identify and isolate an appropriate *Plasmodium* antigen using routine methods known in the art.

In nature, malaria parasites are spread by successively infecting two types of hosts: humans and female *Anopheles* mosquitoes. In this respect, malaria parasites are present as "sporozoites" in the salivary glands of the female *Anopheles* mosquito. When the *Anopheles* mosquito takes a blood meal on another human, the sporozoites are injected with the mosquito's saliva, enter the circulatory system, and within minutes of inoculation will invade a human liver cell (hepatocyte). After invading hepatocytes, the parasite undergoes asexual replication. The stage of the parasite life cycle encompassing sporozoite and liver stages typically is referred to in the art as the "pre-erythrocytic stage," the "liver stage," or "the exo-erythrocytic stage." The progeny, called "merozoites," are released into the circulatory system following rupture of the host hepatocyte.

Merozoites released from the infected liver cells invade erythrocytes (red blood cells). The merozoites recognize specific proteins on the surface of the erythrocyte and actively invade the cell in a manner similar to other mosquito-borne parasites. After entering the erythrocyte, the parasite undergoes a trophic period followed by asexual replication to produce successive broods of merozoites. The progeny merozoite parasites grow inside the erythrocytes and destroy them, and are then released to initiate another round of infection. This stage of infection typically is referred to in the art as the "blood-stage" or "erythrocytic stage." Blood-stage parasites are those that cause the symptoms of malaria. When certain forms of blood-stage parasites (i.e., "gametocytes") are picked up by a female *Anopheles* mosquito during a blood meal, they start another, different cycle of growth and multiplication in the mosquito. The *Plasmodium* life cycle is described in, for example, Ramasamy et al., *Med. Vet. Entomol.*, 11(3): 290-6 (1997), Hall et al., *Science*, 307(5706): 82-6 (2005), and I. W. Sherman, ed., *Malaria: Parasite Biology, Pathogenesis, and Protection*, American Society of Microbiology (1998).

While in some embodiments of the invention it is preferred that the adenoviral vector comprises three or more heterologous nucleic acid sequences, in other embodiments of the invention the adenoviral vector can comprise less than three heterologous nucleic acid sequences. Thus, the invention also provides an adenoviral vector comprising two or more (e.g., 2, 3, 4, 5, 6, 7, 8, 9, 10, or more) heterologous nucleic acid sequences. In this embodiment, each nucleic acid sequence preferably encodes a *Plasmodium* antigen and is operably linked to at least one promoter. In either instance, the *Plasmodium* antigen preferably is a *P. falciparum* antigen. The heterologous nucleic acid sequence can encode any suitable *P. falciparum* antigen, but preferably encodes an antigen that is expressed during the blood-stage of infection (a "blood-stage antigen") and/or an antigen that is expressed during the pre-erythrocytic stage of infection (a "pre-erythrocytic stage antigen"). Blood-stage antigens are known in the art to activate the humoral (i.e., antibody-mediated) arm of the immune system, while pre-erythrocytic stage antigens activate the cell-mediated arm of the immune system (i.e., T cell response). Suitable pre-erythrocytic stage antigens include, but are not limited to, circumsporozoite protein (CSP), sporozoite surface protein 2 (SSP2), liver-stage antigen 1 (LSA-1), Pf exported protein 1 (PfExp-1)/Py hepatocyte erythrocyte protein 17 (PyHEP17), and Pf Antigen 2. Suitable blood-stage antigens include, but are not limited to, merozoite surface protein 1 (MSP-1), merozoite surface protein 2 (MSP-2), erythrocyte binding antigen 175 (EBA-175), ring-infected erythrocyte surface antigen (RESA), serine repeat antigen (SERA), glycophorin binding protein (GBP-130), histidine rich protein 2 (HRP-2), rhoptry-associated proteins 1 and 2 (RAP-1 and RAP-2), erythrocyte membrane protein 1 (PfEMP1), and apical membrane antigen 1 (AMA-1).

In embodiments where the adenoviral vector comprises three or more heterologous nucleic acid sequences, each of the heterologous nucleic acid sequences preferably encodes a pre-erythrocytic stage antigen, a blood-stage antigen, or combinations thereof. For example, the adenoviral vector can comprise three heterologous nucleic acid sequences, in which (i) each heterologous nucleic acid sequence encodes a pre-erythrocytic stage antigen, (ii) each heterologous nucleic acid encodes a blood-stage antigen, (iii) one heterologous nucleic acid sequence encodes a blood-stage antigen, and two heterologous nucleic acid sequences each encodes a pre-erythrocytic stage antigen, or (iv) one heterologous nucleic acid sequence encodes a pre-erythrocytic stage antigen, and two heterologous nucleic acid sequences each encodes a blood-stage antigen. In a preferred embodiment of the invention, each of the three or more heterologous nucleic acid sequences preferably encodes a pre-erythrocytic stage antigen. More preferably, the adenoviral vector comprises three heterologous nucleic acid sequences encoding CSP, SSP2, LSA-1 or Antigen 2.

Similarly, in embodiments where the adenoviral vector comprises two or more heterologous nucleic acid sequences encoding a *Plasmodium* antigen, each of the heterologous nucleic acid sequences preferably encodes a pre-erythrocytic stage antigen, a blood-stage antigen, or combinations thereof. For example, the adenoviral vector can comprise two heterologous nucleic acid sequences in which (i) each heterologous nucleic acid sequence encodes a blood-stage antigen, (ii) each nucleic acid sequence encodes a pre-erythrocytic stage antigen, or (iii) one heterologous nucleic acid sequence encodes a blood-stage antigen, and one heterologous nucleic acid sequence encodes a pre-erythrocytic stage antigen. In a preferred embodiment of the invention, each of the nucleic acid sequences preferably encodes a blood-stage antigen. More preferably, the adenoviral vector comprises two heterologous nucleic acid sequences, each of which encodes MSP-1 and AMA-1, respectively.

It will be appreciated that an entire, intact viral, bacterial, or parasitic protein is not required to produce an immune response. Indeed, most antigenic epitopes are relatively small in size, and, therefore, protein fragments can be sufficient for exposure to the immune system of the mammal. In addition, a fusion protein can be generated between two or more antigenic epitopes of one or more antigens. Delivery of fusion proteins via adenoviral vector to a mammal allows exposure of an immune system to multiple antigens and, accordingly, enables a single vaccine composition to provide immunity against multiple pathogens. In addition, the heterologous nucleic acid sequence encoding a particular antigen can be modified to enhance the recognition of the antigen by the mammalian host. In this regard, the presence of a signal sequence and glycosylation may affect the immunogenicity of a *Plasmodium* antigen expressed by an adenoviral vector. While blood-stage antigens comprising a signal sequence have been shown to induce robust immune responses, a signal sequence is not always sufficient for the efficient secretion or trafficking of *P. falciparum* proteins (see, e.g., Yang et al., *Vaccine*, 15: 1303-13 (1997)). Similarly, glycosylation has been shown to reduce the efficacy of a vaccine candidate based on the C-terminal 42 kD fragment of the *P. falciparum* MSP-1 antigen ($MSP1_{42}$) (see, e.g., Stowers et al., *Proc. Natl. Acad. Sci. USA*, 99: 339-44 (2002)); however, results from studies investigating other *P. falciparum* DNA and protein vaccines demonstrate that glycosylation may not impact vaccine efficacy (see, e.g., Stowers et al., *Infect. Immun.*, 69: 1536-46 (2001)).

Thus the heterologous nucleic acid sequences described herein encode antigens that may or may not comprise a signal sequence. In a preferred embodiment of the invention, at least one of the heterologous nucleic acid sequences present in the adenoviral vector encodes a signal sequence. The term "signal sequence," as used herein, refers to an amino acid sequence, typically located at the amino terminus of a protein, which targets the protein to specific cellular compartments, such as the endoplasmic reticulum, and directs secretion of the mature protein from the cell in which it is produced. Signal sequences typically are removed from a precursor polypeptide and, thus, are not present in mature proteins. Any signal sequence that directs secretion of the protein encoded by the heterologous nucleic acid sequence is suitable for use in the inventive adenoviral vector. Preferably, the signal sequence is a heterologous signal sequence. More preferably, the signal sequence is from the human decay-accelerating factor (DAF) protein, which has been shown to enhance the cell-surface expression and secretion of *P. falciparum* MSP-1 protein (see, e.g., Burghaus et al., *Mol. Biochem. Parasitol.*, 104: 171-83 (1999)). The heterologous nucleic acid sequences in the inventive adenoviral vector desirably are constructed such that, when expressed, a signal sequence is located at the N-terminus of a protein encoded by a heterologous nucleic acid sequence. For example, nucleic acid sequences encoding a $MSP1_{42}$ *P. falciparum* antigen comprising a heterologous signal sequence include, SEQ ID NO: 20, SEQ ID NO: 22, and SEQ ID NO: 24. Alternatively, non-secreted (NS) versions of the antigens encoded by the heterologous nucleic acid sequences can be generated by any suitable means, but preferably are generated by deleting a signal sequence from the heterologous nucleic acid sequence. Nucleic acid sequences encoding *P. falciparum* antigens which lack a signal sequence include, for example, SEQ ID NO: 14 (AMA-1) and SEQ ID NO: 18 ($MSP1_{42}$). A particular antigen may also be directed to the cell surface by the presence of an anchor amino acid sequence in the antigen amino acid sequence. Such anchor sequences are known in the art and include, for example, glycosylphosphatidylinisotol (GPI) anchors. GPI anchored proteins are membrane bound proteins found throughout the animal kingdom. GPI anchored proteins are linked at their carboxyterminus through a phosphodiester linkage of phosphoethanolamine to a trimannosyl-non-acetylated glucosamine (Man3-GlcN) core. The reducing end of GlcN is linked to phosphatidylinositol (PI). PI is then anchored through another phosphodiester linkage to the cell membrane through its hydrophobic region (see, e.g., Sigma-Aldrich website and Takeda et al., Trends. Biochem. Sci., 20(9): 367-71 (1995). Deleting or otherwise inhibiting the GPI anchor (e.g., via a GPI anchor inhibiting tail) results in secretion of the antigen from the cell.

In addition, the heterologous nucleic acid sequences described herein encode antigens that may or may not be glycosylated (e.g., N-linked or O-linked glycosylation). In a preferred embodiment of the invention, at least one of the heterologous nucleic acid sequences present in the adenoviral vector encodes an antigen that is not glycosylated (N-glycosylated or O-glycosylated). More preferably, the heterologous nucleic acid sequence encodes an antigen that is not N-glycosylated. While recent studies indicate that *P. falciparum* proteins do not contain significant amounts of N-linked and O-linked carbohydrates (Gowda et al., *Parisitol. Today*, 15: 147-52 (1999)), some *P. falciparum* proteins contain potential glycosylation sites (Yang et al., *Glycobiology*, 9: 1347-56 (1999)). Glycosylation of the antigens encoded by the heterologous nucleic acid sequences in the inventive adenoviral vector can be inhibited by any suitable method. Preferably, glycosylation is inhibited by making mutations in glycosylation sites present in the heterologous nucleic acid sequences. Such mutations include those that would effect deletions, substitutions, and/or insertions of amino acids in the antigen. Preferably, glycosylation is inhibited by mutating a heterologous nucleic acid sequence encoding a *Plasmodium* antigen such that at least one amino acid of a glycosylation site is substituted with a different amino acid. An exemplary substitution includes replacement of the asparagine residue at position 321 of the *P. falciparum* MSP-1 protein with a glutamine residue. In addition, certain asparagines residues of the *P. falciparum* AMA-1 protein also can be substituted to inhibit glycosylation. For example, the asparagine residue at position 162 can be substituted with a lysine residue, and the asparagine residues at positions 266, 371, 421, 422, and 499 can be replaced with glutamine residues. These mutations are exemplary and in no way limiting. Indeed, any mutation can be utilized that disrupts a native glycosylation site. Nucleic acid sequences encoding *P. falciparum* antigens comprising mutated glycosylation sties include, for example, SEQ ID NO: 12, SEQ ID NO: 16, and SEQ ID NO: 22.

When the heterologous nucleic acid sequence encodes an antigen, preferably a *Plasmodium* antigen, the heterologous nucleic acid sequence comprises codons expressed more frequently in humans than in the pathogen from which the heterologous nucleic acid sequence is derived. While the genetic code is generally universal across species, the choice among synonymous codons is often species-dependent. Infrequent usage of a particular codon by an organism likely reflects a low level of the corresponding transfer RNA (tRNA) in the organism. Thus, introduction of a nucleic acid sequence into an organism which comprises codons that are not frequently utilized in the organism may result in limited expression of the nucleic acid sequence. One of ordinary skill in the art would appreciate that, to achieve maximum protection against *Plasmodium* infection, the inventive adenoviral vector must be capable of expressing high levels of *Plasmodium* antigens in a mammalian, preferably a human, host. In this respect, the heterologous nucleic acid sequence preferably encodes the native amino acid sequence of a *Plasmodium* antigen, but comprises codons that are expressed more frequently in mammal (e.g., humans) than in *Plasmodium*. Such modified nucleic acid sequences are commonly described in the art as "humanized," as "codon-optimized," or as utilizing "mammalian-preferred" or "human-preferred" codons.

In the context of the invention, a *Plasmodium* nucleic acid sequence is said to be "codon-optimized" if at least about 60% (e.g., at least about 70%, at least about 80%, or at least about 90%) of the wild-type codons in the nucleic acid sequence are modified to encode mammalian-preferred codons. That is, a *Plasmodium* nucleic acid sequence is codon-optimized if at least about 60% of the codons encoded therein are mammalian-preferred codons. Preferred codon-optimized nucleic acid sequences encoding the *P. falciparum* CSP antigen include, for example, SEQ ID NO: 4, SEQ ID NO: 6, and SEQ ID NO: 8. Preferred codon-optimized nucleic acid sequences encoding the *P. falciparum* SSP-2 antigen include, for example, SEQ ID NO: 28 and SEQ ID NO: 30. A preferred codon-optimized nucleic acid sequence encoding the *P. falciparum* AMA-1 antigen and the LSA-1 antigen includes SEQ ID NO: 10 and SEQ ID NO: 26, respectively. However, the invention is not limited to these exemplary sequences. Indeed, genetic sequences can vary between different strains, and this natural scope of allelic variation is included within the scope of the invention. Additionally and alternatively, the codon-optimized nucleic acid sequence encoding a *P. falciparum* antigen can be any sequence that hybridizes to above-described sequences under at least moderate, preferably high, stringency conditions, such as those described in Sambrook et al., supra. Determining the degree of homology can be accomplished using any suitable method (e.g., BLASTnr, provided by GenBank).

Each of the heterologous nucleic acid sequences in the inventive adenoviral vector is desirably present as part of an expression cassette, i.e., a particular nucleotide sequence that possesses functions which facilitate subcloning and recovery of a nucleic acid sequence (e.g., one or more restriction sites) or expression of a nucleic acid sequence (e.g., polyadenylation or splice sites). Each heterologous nucleic acid is preferably located in the E1 region (e.g., replaces the E1 region in whole or in part) and/or the E4 region of the adenoviral genome. For example, the E1 region can be replaced by one or more promoter-variable expression cassettes comprising a heterologous nucleic acid. Alternatively, in embodiments where the adenoviral vector contains the E1 region but is deficient in the E4 region, the E4 region can be replaced by one or more expression cassettes. In this manner, inserting an expression cassette into the E4 region of the adenoviral genome inhibits formation of "revertant E1 adenovectors" (REA), because homologous recombination within the E1 region and the E1 DNA of a complementing cell line (e.g., 293 cell) or helper virus results in an E1-containing adenoviral genome that is too large for packaging inside an adenovirus capsid. Each expression cassette can be inserted in a 3'-5' orientation, e.g., oriented such that the direction of transcription of the expression cassette is opposite that of the surrounding adjacent adenoviral genome. However, it is also appropriate for an expression cassette to be inserted in a 5'-3' orientation with respect to the direction of transcription of the surrounding genome. In this regard, it is possible for the inventive adenoviral vector to comprise at least one heterologous nucleic acid sequence that is inserted into, for example, the E1 region in a 3'-5' orientation, and at least one heterologous nucleic acid sequence inserted into the E4 region in a 5'-3' orientation. In embodiments where the E1 and/or the E4 region are replaced by two or more expression cassettes (e.g., a dual expression cassette), each of the expression cassettes can be positioned in any orientation with respect to each other. For example, two expression cassettes can be positioned such that each of the respective promoters is adjacent to the other. In this manner, one expression cassette is in a 5'-3' orientation with respect to the direction of transcription of the adenoviral genome, and the other expression cassette is in a 3'-5' orientation. By positioning two promoters adjacent to each other, the activity of one of the promoters can be enhanced by the activity of the adjacent promoter.

In accordance with the invention, at least one heterologous nucleic acid sequence (e.g., one, two, three, or more heterologous nucleic acid sequences) is located in the E1 region of the adenoviral genome, and at least one heterologous nucleic acid sequence (e.g., one, two, three, or more heterologous nucleic acid sequences) is located in the E4 region of the adenoviral genome. In embodiments where the adenoviral vector comprises three or more nucleic acid sequence, at least one heterologous nucleic acid sequence preferably is located in the E1 region of the adenoviral genome, and at least two heterologous nucleic acid sequences preferably are located in the E4 region of the adenoviral genome. Alternatively, at least two heterologous nucleic acid sequences can be located in the E1 region of the adenoviral genome, and at least one heterologous nucleic acid sequence can be located in the E4 region of the adenoviral genome. While not preferred, all of the heterologous nucleic acid sequences can be located in either the E1 region or the E4 region of the adenoviral genome. In embodiments where the adenoviral vector comprises two or more nucleic acid sequences encoding a *Plasmodium* antigen, each of the two or more nucleic acid sequences preferably are located in the E1 region or the E4 region of the adenoviral genome. Most preferably, each of the two or more heterologous nucleic acid sequences is located in the E4 region of the adenoviral genome. The insertion of an expression cassette into the adenoviral genome (e.g., into the E1 region of the genome) can be facilitated by known methods, for example, by the introduction of a unique restriction site at a given position of the adenoviral genome. As set forth above, preferably all or part of the E3 region of the adenoviral vector also is deleted.

Preferably, each heterologous nucleic acid sequence is operably linked to (i.e., under the transcriptional control of) one or more promoter and/or enhancer elements, for example, as part of a promoter-variable expression cassette. Techniques for operably linking sequences together are well known in the art. Any promoter or enhancer sequence can be used in the context of the invention, so long as sufficient expression of the heterologous nucleic acid sequence is achieved and a robust immune response against the encoded antigen is generated. Preferably, the promoter is a heterologous promoter, in that the promoter is not obtained from, derived from, or based upon a naturally occurring promoter of the adenoviral vector. In this regard, the promoter can be a viral promoter. Suitable viral promoters include, for example, cytomegalovirus (CMV) promoters, such as the mouse CMV immediate-early promoter (mCMV) or the human CMV immediate-early promoter (hCMV) (described in, for example, U.S. Pat. Nos. 5,168,062 and 5,385,839), promoters derived from human immunodeficiency virus (HIV), such as the HIV long terminal repeat promoter, Rous sarcoma virus (RSV) promoters, such as the RSV long terminal repeat or a promoter of SEQ ID NO: 4, mouse mammary tumor virus (MMTV) promoters, HSV promoters, such as the Lap2 promoter or the herpes thymidine kinase promoter (Wagner et al., *Proc. Natl. Acad. Sci.*, 78: 144-145 (1981)), promoters derived from SV40 or Epstein Barr virus, an adeno-associated viral promoter, such as the p5 promoter, and the like. Preferably, the promoter is the CMV immediate-early promoter (mouse or human) or an RSV promoter.

Alternatively, the promoter can be a cellular promoter, i.e., a promoter that is native to eukaryotic, preferably animal, cells. In one aspect, the cellular promoter is preferably a constitutive promoter that works in a variety of cell types, such as cells associated with the immune system. Suitable constitutive promoters can drive expression of genes encoding transcription factors, housekeeping genes, or structural genes common to eukaryotic cells. Suitable cellular promoters include, for example, a ubiquitin promoter (e.g., a UbC promoter) (see, e.g., Marinovic et al., *J. Biol. Chem.*, 277(19): 16673-16681 (2002)), a human β-actin promoter, an EF-1α promoter, a YY1 promoter, a basic leucine zipper nuclear factor-1 (BLZF-1) promoter, a neuron specific enolase (NSE) promoter, a heat shock protein 70B (HSP70B) promoter, and a JEM-1 promoter. Preferably, the cellular promoter is a ubiquitin promoter.

Many of the above-described promoters are constitutive promoters. Instead of being a constitutive promoter, the promoter can be an inducible promoter, i.e., a promoter that is up- and/or down-regulated in response to an appropriate signal. The use of a regulatable promoter or expression control sequence is particularly applicable to DNA vaccine development inasmuch as antigenic proteins, including viral and parasite antigens, frequently are toxic to complementing cell lines. A promoter can be up-regulated by a radiant energy source or by a substance that distresses cells. For example, an expression control sequence can be up-regulated by drugs, hormones, ultrasound, light activated compounds, radiofrequency, chemotherapy, and cyofreezing. Thus, the promoter sequence that regulates expression of the heterologous nucleic acid sequence can contain at least one heterologous regulatory sequence responsive to regulation by an exogenous agent. Suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed.

The promoter can be a tissue-specific promoter, i.e., a promoter that is preferentially activated in a given tissue and results in expression of a gene product in the tissue where activated. A tissue-specific promoter suitable for use in the invention can be chosen by the ordinarily skilled artisan based upon the target tissue or cell-type. Preferred tissue-specific promoters for use in the inventive method are specific to immune cells, such as the dendritic-cell specific Dectin-2 promoter described in Morita et al., *Gene Ther.*, 8: 1729-37 (2001).

In yet another embodiment, the promoter can be a chimeric promoter. A promoter is "chimeric" in that it comprises at least two nucleic acid sequence portions obtained from, derived from, or based upon at least two different sources (e.g., two different regions of an organism's genome, two different organisms, or an organism combined with a synthetic sequence). Preferably, the two different nucleic acid sequence portions exhibit less than about 40%, more preferably less than about 25%, and even more preferably less than about 10% nucleic acid sequence identity to one another (which can be determined by methods described elsewhere herein). Chimeric promoters can be generated using standard molecular biology techniques, such as those described in Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994).

A promoter can be selected for use in the method of the invention by matching its particular pattern of activity with the desired pattern and level of expression of the antigen(s). In this respect, the adenoviral vector preferably comprises two or more heterologous nucleic acid sequences that encode different antigens and are operably linked to different promoters displaying distinct expression profiles. For example, a first promoter is selected to mediate an initial peak of antigen production, thereby priming the immune system against an encoded antigen. A second promoter is selected to drive production of the same or different antigen such that expression peaks several days after the initial peak of antigen production driven by the first promoter, thereby "boosting" the immune system against the antigen. Alternatively, a chimeric promoter can be constructed which combines the desirable aspects of multiple promoters. For example, a CMV-RSV hybrid promoter combining the CMV promoter's initial rush of activity with the RSV promoter's high maintenance level of activity is especially preferred for use in many embodiments of the inventive method. In addition, a promoter can be modified to include heterologous elements that enhance its activity. For example, a human CMV promoter sequence can include a synthetic splice signal, which enhances expression of a nucleic acid sequence operably linked thereto. In that antigens can be toxic to eukaryotic cells, it may be advantageous to modify the promoter to decrease activity in complementing cell lines used to propagate the adenoviral vector.

Multiple heterologous nucleic acid sequences can be operably linked to the same or different promoters. In a preferred embodiment of the invention, each heterologous nucleic acid sequence is operably linked to a separate promoter. While it is preferred that each promoter is different, one or ordinary skill in the art will appreciate the advantages of using one particularly efficient promoter to control expression of each heterologous nucleic acid sequence present in the adenoviral vector. Thus, each heterologous nucleic acid sequence can be operably linked to the same promoter. When the adenoviral vector comprises three or more heterologous nucleic acid sequences, the three or more heterologous nucleic acid sequences are operably linked to two or more different promoters (e.g., two heterologous nucleic acid sequences are each operably linked to the same promoter, and one heterologous nucleic acid sequence is operably linked to a different promoter). Most preferably, each of the three or more heterologous nucleic acid sequences is operably linked to a different promoter. The selection of an appropriate promoter for a given heterologous nucleic acid sequence will depend upon a number of factors, including promoter strength and the position of the expression cassette within the adenoviral genome, and can be performed using routine methods known in the art.

To optimize protein production, preferably each heterologous nucleic acid sequence further comprises a polyadenylation site 3' of the coding sequence. Any suitable polyadenylation sequence can be used, including a synthetic optimized sequence, as well as the polyadenylation sequence of BGH (Bovine Growth Hormone), mouse globin D (MGD), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence. Also, preferably all the proper transcription signals (and translation signals, where appropriate) are correctly arranged such that the nucleic acid sequence is properly expressed in the cells into which it is introduced. If desired, the heterologous nucleic acid sequence also can incorporate splice sites (i.e., splice acceptor and splice donor sites) to facilitate mRNA production.

The invention also provides a method of inducing an immune response against malaria in a mammal. The method comprises administering to the mammal (a) an adenoviral vector comprising an adenoviral genome comprising three or more nucleic acid sequences, wherein each nucleic acid sequence encodes a *Plasmodium* pre-erythrocytic stage antigen and is operably linked to at least one promoter, and (b) an adenoviral vector comprising an adenoviral genome comprising two or more nucleic acid sequences, wherein each nucleic acid sequence encodes a *Plasmodium* blood-stage antigen and is operably linked to at least one promoter. Descriptions of the adenoviral vectors, *Plasmodium* antigens, and promoters set forth above in connection with other embodiments of the invention also are applicable to those same aspects of the aforesaid method.

In the method of the invention, the adenoviral vectors preferably are administered to a mammal (e.g., a human), wherein the nucleic acid sequences encoding the *Plasmodium* antigens are expressed to induce an immune response against the antigens. The adenoviral vectors can be separately formulated and administered simultaneously or sequentially in any order. Alternatively, the adenoviral vectors can be part of the same pharmaceutical composition. The immune response can be a humoral immune response, a cell-mediated immune response, or, desirably, a combination of humoral and cell-mediated immunity. Ideally, the immune response provides protection upon subsequent challenge with the infectious agent comprising the antigen. However, protective immunity is not required in the context of the invention. The inventive method further can be used for antibody production and harvesting.

Administering the adenoviral vectors encoding *Plasmodium* antigens can be one component of a multistep regimen for inducing an immune response in a mammal. In particular, the inventive method can represent one arm of a prime and boost immunization regimen. The inventive method, therefore, can comprise administering to the mammal a priming gene transfer vector comprising a nucleic acid sequence encoding at least one antigen prior to administering the adenoviral vectors. The antigen encoded by the priming gene transfer vector can be the same or different from the antigens of the adenoviral vectors. The inventive adenoviral vectors are then administered to boost the immune response to a given pathogen. More than one boosting composition comprising the adenoviral vectors can be provided in any suitable timeframe (e.g., at least about 1 week, 2 weeks, 4 weeks, 8 weeks, 12 weeks, 16 weeks, or more following priming) to maintain immunity.

Any gene transfer vector can be employed as a priming gene transfer vector, including, but not limited to, a plasmid, a retrovirus, an adeno-associated virus, a vaccinia virus, a herpesvirus, an alphavirus, or an adenovirus. Ideally, the priming gene transfer vector is a plasmid, an alphavirus, or an adenoviral vector. To maximize the effect of the priming regimen, the priming gene transfer vector can comprise more than one heterologous nucleic acid sequence encoding an antigen. Preferably, the priming gene transfer vector comprises two or more (e.g., 2, 3, 5, or more) or three or more (e.g., 3, 5, 7, 9, or more) heterologous nucleic acid sequences each encoding an antigen. Alternatively, an immune response can be primed or boosted by administration of the antigen itself, e.g., an antigenic protein, intact pathogen (e.g., *Plasmodium* sporozoites), parasitized erythrocytes, inactivated pathogen, and the like.

Any route of administration can be used to deliver the adenoviral vector to the mammal. Indeed, although more than one route can be used to administer the adenoviral vector, a particular route can provide a more immediate and more effective reaction than another route. Preferably, the adenoviral vector is administered via intramuscular injection. A dose of adenoviral vector also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The adenoviral vector can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the adenoviral vector. The adenoviral vector also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of adenoviral vector administered to the mammal will depend on a number of factors, including the size of a target tissue, the extent of any side-effects, the particular route of administration, and the like. The dose ideally comprises an "effective amount" of adenoviral vector, i.e., a dose of adenoviral vector which provokes a desired immune response in the mammal. The desired immune response can entail production of antibodies, protection upon subsequent challenge, immune tolerance, immune cell activation, and the like. Desirably, a single dose of adenoviral vector comprises at least about $1\times10^5$ particles (which also is referred to as particle units) of the adenoviral vector. The dose preferably is at least about $1\times10^6$ particles (e.g., about $1\times10^6$–$1\times10^{12}$ particles), more preferably at least about $1\times10^7$ particles, more preferably at least about $1\times10^8$ particles (e.g., about $1\times10^8$–$1\times10^{11}$ particles), and most preferably at least about $1\times10^9$ particles (e.g., about $1\times10^9$–$1\times10^{10}$ particles) of the adenoviral vector. The dose desirably comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ particles). In other words, a single dose of adenoviral vector can comprise, for example, about $1\times10^6$ particle units (pu), $2\times10^6$ pu, $4\times10^6$ pu, $1\times10^7$ pu, $2\times10^7$ pu, $4\times10^7$ pu, $1\times10^8$ pu, $2\times10^8$ pu, $4\times10^8$ pu, $1\times10^9$ pu, $2\times10^9$ pu, $4\times10^9$ pu, $1\times10^{10}$ pu, $2\times10^{10}$ pu, $4\times10^{10}$ pu, $1\times10^{11}$ pu, $2\times10^{11}$ pu, $4\times10^{11}$ pu, $1\times10^{12}$ pu, $2\times10^{12}$ pu, or $4\times10^{12}$ pu of the adenoviral vector.

The adenoviral vector desirably is administered in a composition, preferably a pharmaceutically acceptable (e.g., physiologically acceptable) composition, which comprises a carrier, preferably a pharmaceutically (e.g., physiologically acceptable) carrier and the adenoviral vector(s). Any suitable carrier can be used within the context of the invention, and such carriers are well known in the art. The choice of carrier will be determined, in part, by the particular site to which the composition is to be administered and the particular method used to administer the composition. Ideally, in the context of adenoviral vectors, the composition preferably is free of replication-competent adenovirus. The composition can optionally be sterile or sterile with the exception of the inventive adenoviral vector.

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the adenoviral vector for use in the inventive method is administered in a composition formulated to protect the expression vector from damage prior to administration. For example, the composition can be formulated to reduce loss of the adenoviral vector on devices used to prepare, store, or administer the expression vector, such as glassware, syringes, or needles. The composition can be formulated to decrease the light sensitivity and/or temperature sensitivity of the expression vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the vector, facilitate administration, and increase the efficiency of the inventive method. Formulations for adenoviral vector-containing compositions are further described in, for example, U.S. Pat. No. 6,225,289, U.S. Pat. No. 6,514,943, U.S. Patent Application Publication 2003/0153065 A1, and International Patent Application Publication WO 00/34444. A composition also can be formulated to enhance transduction efficiency. In addition, one of ordinary skill in the art will appreciate that the adenoviral vector can be present in a composition with other therapeutic or biologically-active agents. For example, factors that control inflammation, such as ibuprofen or steroids, can be part of the composition to reduce swelling and inflammation associated with in vivo administration of the viral vector. As discussed herein, immune system stimulators or adjuvants, e.g., interleukins, lipopolysaccharide, and double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the invention but, of course, should not be construed as in any way limiting its scope.

Example 1

This example demonstrates the preparation of an adenoviral vector comprising a heterologous nucleic acid sequence encoding a *P. falciparum* blood-stage antigen.

Ten serotype 5 E1/E3/E4-deficient adenoviral vectors containing, in place of the deleted E1 region, a nucleic acid sequence encoding non-secreted (NS), secreted and glycosylated (SG), and secreted and non-glycosylated (SNG) versions of the *P. falciparum* AMA-1 (PfAMA1) and MSP-1$_{42}$ (PfMSP1$_{42}$) proteins were generated. The SG version of PfMSP1$_{42}$ was generated by fusing the decay-accelerating factor (DAF) signal sequence to the 5' end of the PfMSP1$_{42}$ gene. The SNG version of PfMSP1$_{42}$ contains the DAF signal sequence and an asparagine to glutamine substitution at amino acid position 321. The SG version of PfAMA1 is the full-length PfAMA1 gene. The SNG version of PfAMA1 contains asparagine to glutamine substitutions at amino acid positions 286, 371, 421, 422, and 499, and an asparagine to lysine substitution at amino acid position 162. The NS version of PfAMA1 contains a deletion of the native signal sequence.

In each adenoviral vector construct, the PfMSP1$_{42}$ gene was expressed from an expression cassette inserted into the site of the E1 deletion in the opposite orientation with respect to adenoviral vector transcription. The expression cassette contains, from 5' to 3', the human CMV promoter (hCMV) having a synthetic splice signal, the PfMSP1$_{42}$ gene, and an SV40 polyadenylation signal. In each adenoviral vector construct, the PfAMA1 gene was expressed from a murine CMV promoter (mCMV) in an expression cassette inserted into the site of the E4 deletion.

To insure that the mCMV expression cassette located in the E4 region was comparable to the hCMV expression cassette in the E1 region, three additional vectors were generated as controls: (1) AdPfAMA1 (SG), which comprises the SG version of PfAMA1 operably linked to the hCMV promoter in the E1 region, (2) AdmCMVPfAMA1 (SG), which comprises the SG version of PfAMA1 operably linked to the mCMV promoter in the E1 region, and (3) Ada.E4t.PfAMA1 (SG) which comprises the SG version of PfAMA1 operably linked to the hCMV promoter in the E4 region.

The vectors comprising SG, SNG, and NS versions of the PfAMA1 gene and the PfMSP1$_{42}$ gene were evaluated for glycosylation status and the cellular localization of the antigens. Immunoblot analysis indicated that the apparent molecular weight of the SG version of PfAMA1 was higher than that of the NS or S versions, suggesting that the SG version was post-translationally modified. Immunoblot analysis also indicated that the apparent molecular weight of the SG version of MSP1$_{42}$ was higher than that of the NS or SNG versions, suggesting that the SG version was post-translationally modified. Glycosylation status was confirmed by infecting A549 cells with the PfAMA1 of PfMSP1$_{42}$ vectors and then treating the cellular lysate harvested 24 hours post-infection with either Endo H or PNGase F. PNGaseF hydrolyses complex, hybrid, and high-mannose type N-glycans and Endo H cleaves high-Mannose type structures only. Treatment with both enzymes resulted in a reduction in the apparent molecular weight of the PfAMA1 (SG) product and the MSP-1$_{42}$ (SG) product, indicating that PfAMA1 (SG) and MSP1$_{42}$ (SG) are both N-glycosylated. No shift in the apparent molecular weight of the NS or the SNG versions of PfAMA1 was observed. No shift in the molecular weight of the NS version and a minor shift in the molecular weight of the SNG version of PfMSP1$_{42}$ were observed, possibly due to the ionic strength differences in the of the enzymatic digestion buffer. Expression of the PfAMA1 (NS) antigen was greatly reduced relative to the SG and SNG antigens; however, other immunoblots using different antibodies demonstrated that the NS antigen is expressed efficiently.

Immunoblot analysis of all of the adenovector constructs indicated that none of the AMA 1 vectors secreted the antigen into the culture media, and that the majority of the MSP protein is not secreted into the culture media. Immunofluorescence assays (IFA) indicated that the PfAMA1 (SG) antigen is located at the cell surface, as similar levels of PfAMA1 were observed in non-permeabilized vs. permeabilized cells.

The SNG version of AMA 1 was not present on the outside of the cell, as permeabilization was necessary to detect the antigen by IFA. Protease digestion of intact infected cells confirmed these findings and revealed that PfAMA1 (SG) was cleaved by trypsin and that the PfAMA1 (SNG), and PfAMA1 (NS) antigens were not cleaved by trypsin. This analysis suggests that the PfAMA1 (SG) antigen is present at the cell surface in a conformation that is recognized by the 4G2 antibody and sensitive to trypsin digestion.

IFA also indicated that none of the MSP1$_{42}$ antigens are associated with the cell surface, as permeabilization of the cells was required to detect PfMSP1 antigens by IFA. However, protease digestion of intact infected cells revealed that PfMSP1$_{42}$ (SG) was cleaved by trypsin and that the PfMSP1$_{42}$ (SNG) and PfMSP1$_{42}$ (NS) antigens were not cleaved by trypsin. This analysis suggests that the PfMSP1$_{42}$ (SG) antigen is present at the cell surface in a conformation that is sensitive to trypsin digestion but is not recognized by the polyclonal antisera used in the IFA assay. The results of these experiments are summarized in Table 1.

TABLE 1

| Vector Name | Glycoyslation | Cellular Localization |
| --- | --- | --- |
| Adt.Pf MSP1$_{42}$ (NS) | No | Intracellular |
| Adt.PfMSP-3.11D (SG) | Yes | Cell surface |
| Adt.PfMSP-4.11D (SNG) | No | Intracellular |
| Adt.PfAMA1 (SG) (control) | Not determined | Not determined |
| AdmCMV.PfAMA1 (SG) (control | Not determined | Not determined |
| Add2.E4mCMVPfAMA1 (SG) | Yes | Cell surface |
| Add2.E4mCMVPfAMA1 (SNG) | No | Intracellular |
| Add2.E4mCMVPfAMA1 (NS) | No | intracellular |
| Add1.E4PfAMA (SG) (control) | Not determined | Not determined |
| Ada.E4t.PfAMA1 (SG) | Not determined | Not determined |

The results of this example demonstrate the production of adenoviral vectors comprising secreted, non-secreted, glycosylated, and non-glycosylated versions of *P. falciparum* blood-stage antigens.

Example 2

This example demonstrates the immunogenicity of an adenoviral vector comprising a heterologous nucleic acid sequence encoding a *P. falciparum* blood-stage antigen.

Four serotype 5 E1/E3/E4-deficient adenoviral vectors containing, in place of the deleted E1 region, a nucleic acid sequence encoding non-secreted (NS), secreted and glycosylated (SG), secreted and non-glycosylated (SNG), and wild-type versions of the *P. falciparum* MSP1$_{42}$ (PfMSP1$_{42}$) or AMA-1 (PfAMA1) proteins were generated as described in Example 1. To anchor the MSP1$_{42}$ proteins to the cell membrane, the nucleic acid sequences encoding the NS, SG, and SNG versions of Pf MSP1$_{42}$ also contained a glycosylphosphatidylinisotol (GPI) anchor sequence. Similarly, the wild-type MSP1$_{42}$ nucleic acid sequence contained the DAF anchor sequence and the DAF signal sequence (i.e., Ad.PfMSP1$_{42}$(DSA)). In addition to the secreted and non-glycosylated (SNG) version of PfAMA1 described in Example 1, a second SNG PfAMA1 adenovector construct (SNG2) was generated. The SNG2 version of PfAMA1 contains the following amino acid substitutions: Asn162Lys, Tyr287Leu, Thr288Val, Ala372Arg, Ser373Val, Ser423Lys, Asn422Asp, Ser424Asn, and Asn499Gln.

The adenoviral vectors were evaluated for glycosylation status and the cellular localization of the antigens as described in Example 1. T-cell immune responses induced by the recombinant adenoviral vectors described above were evaluated in a mouse model. Specifically, BALB/c mice ages 3-6 weeks were immunized intramuscularly in the tibialis anterior muscle with the PfMSP1$_{42}$ or PfAMA1-expressing adenovectors described above at a dose of 1×10$^8$ pu in a total volume of 100 µl split between the two muscles. CD8+ and CD4+ T cell responses were measured by intercellular cytokine staining (ICS) or IFN-γ ELIspot following in vitro restimulation with pools of synthetic peptides derived from PfMSP1$_{42}$ or PfAMA1. Nonimmunized naïve mice were evaluated in parallel. Antibody responses were evaluated by an ELISA assay utilizing serial dilutions of antisera from mice immunized with each of the PfMSP1$_{42}$ of PfAMA1 expressing adenovectors. The results of these experiments are set forth in Table 2.

TABLE 2

| Vector Name | N-Glyco-sylation | Cell Surface Localization | T Cell Response | Antibody Response |
|---|---|---|---|---|
| Ad.PfMSP1$_{42}$ (NS) | No | Not determined | Yes | No |
| Ad.PfMSP1$_{42}$ (SG) | Yes | Yes | Yes | Yes |
| Ad.PfMSP1$_{42}$ (SNG) | No | Yes | Yes | Yes |
| Ad.PfMSP1$_{42}$ (DSA) | Yes | Yes | Yes | Yes |
| Ad.PfAMA1 (SG) | Yes | Yes | Yes | Yes |
| Ad.PfAMA1 (SNG) | No | Yes | Yes | Yes |
| Ad.PfAMA1 (SNG2) | No | Yes | Yes | Yes |
| Ad.PfAMA1 (NS) | No | No | No | No |

The results of this example demonstrate the production of adenoviral vectors comprising secreted, non-secreted, glycosylated, and non-glycosylated versions of P. falciparum blood-stage antigens and their associated immunogenicity in vivo.

Example 3

This example demonstrates the effect of promoter type, as well as promoter location and orientation, on expression of Plasmodium antigens encoded by an adenoviral vector in vivo and in vitro.

The use of multiple copies of a single strong promoter to express different antigens in a multivalent vector is expected to lead to vector instability due to homologous recombination between the promoters. Therefore, to identify suitable promoters for a multivalent adenoviral vector-based malaria vaccine, a set of adenoviral vectors expressing luciferase from various promoters was screened in mice to identify promoters suitable to control expression of Plasmodium genes. Specifically, cohorts of five female C57BL/6 mice were injected with 1×10$^{10}$ particle units pu) of an E1/E3/E4-deficient adenoviral vector containing a luciferase expression cassette at the site of the E1 deletion. The luciferase gene was operably linked to each of the following promoters: a human CMV promoter (hCMV), a human CMV enhanced chicken beta actin chimeric promoter (CCBA), a human beta actin (hpA) promoter, a murine CMV promoter, an elongation factor alpha (Ef1α) promoter, a ubiquitin (Ub) promoter, an RSV promoter, a Ying Yang 1 (YY1) promoter, a basic leucine zipper nuclear factor-1 (BLZF1) promoter, a neuron specific enolase (NSE) promoter, and a heat shock specific 70B (HSP70B) promoter. 24 hours post-injection into the tibialis muscle of each mouse, muscle tissue was harvested and luciferase levels were measured in relative light units (RLU)/µg protein. Mice injected with reaction buffer served as a negative control.

Three categories of promoters were identified: high, medium, and low expression. High expression is defined as activity equivalent to or better than the mCMV promoter. The high expression group includes the hCMV, CCBA, hβA, Ef1α and mCMV promoters. The medium expression group includes the Ubiquitin (Ub) promoter, while the low expression group includes the RSV, YY1, BLZF-1, NSE and HSP70B promoters.

The effect of location and orientation of expression cassettes within the adenovector genome was also evaluated using luciferase marker genes in vivo. The E1 and E4 regions were found to provide equivalent high levels of expression when tested with the hCMV and mCMV promoters. Likewise, the orientation of the expression cassette within the E4 region did not affect expression levels. However, 100-fold reduced expression was observed when an hβA expression cassette was inserted into the deleted E3 region of the adenovector, relative to expression observed when the same cassette was inserted into the deleted E1 region.

These results suggest that high levels of Plasmodium gene expression in an adenovector can be achieved using a high expressing promoter, e.g., hCMV promoter, and inserting the expression cassette into the site of an E1 and/or E4 deletion.

Example 4

This example demonstrates the preparation of an adenoviral vector comprising two heterologous nucleic acid sequence encoding P. falciparum blood-stage antigens.

Based on the experiments described above, it was determined that an adenoviral vector encoding the SNG of SG versions of both PfAMA1 and PfMSP1$_{42}$ was most likely to result in an effective vaccine construct. To this end, an E1/E4-deficient adenoviral vector was constructed comprising the PfMSP1$_{42}$ (SNG) gene in an expression cassette located in the deleted E1 region and the PfAMA1 (SNG) gene in an expression cassette located in the deleted E4 region of the virus. Specifically, an E1 shuttle vector was constructed which expresses the PfMSP1$_{42}$ (SNG) antigen from the hCMV promoter (pAdCMV.PfMSP1$_{42}$ (SNG)). An E4 shuttle vector that expresses the PfAMA1 (SNG) antigen from the mCMV promoter (pAdE4mCMV.PfAMA1(SNG)) also was generated using method described in, for example, International Patent Application Publication No. WO 99/15686 and U.S. Pat. No. 6,329,200. These shuttle vectors were recombined with plasmids generated by the AdFast™ technology (GenVec, Inc., Gaithersburg, Md.) (see International Patent Application Publication No. WO 99/15686 and U.S. Pat. No. 6,329,200) to generate a new adenovector plasmid called pAd(t.PfMSP1$_{42}$SNG)E3 (10)E4(mCM-V.PfAMA1 SNG)pkg. This plasmid was converted into virus and expanded to generate a high titer vector stock of the Adt.PfMSP1$_{42}$ (SNG)E4mCMV.PfAMA1(SNG) adenoviral vector. In a similar manner, a second E1/E4-deficient adenoviral vector was constructed in which the E1 region was replaced with two expression cassettes: one comprising the PfMSP1$_{42}$ (SG) gene, and the other comprising the PfAMA1 (SG) gene (AdE1(MSP1$_{42}$SSG/mCMVAMASG)). High titer stocks of both vectors were fully certified and their genetic structural identity was confirmed by a PCR-based assay.

T-cell immune responses induced by the recombinant adenoviral vector AdE1(MSP1$_{42}$SSG/mCMVAMASG) were evaluated as described in Example 2. In particular, mice were divided into 16 groups, of which groups 1-5 received no priming immunization, groups 6-10 received a priming immunization of control DNA, PfAMA1 DNA, PfMSP1 DNA, or a cocktail of PfAMA1 DNA and PfMSP1 DNA, and groups 11-15 received a priming immunization of either AdNull, an E1/E4-deficient vector encoding only PfAMA1 (SG) (AdPfAMA1(SG)) or PfMSP1$_{42}$ (SG) (AdPfMSP1$_{42}$ (SG)), a cocktail of AdPfAMA1 (SG) and AdPfMSP1$_{42}$ (SG), or AdE1(MSP1$_{42}$SSG/mCMVAMASG). Mice were administered a boosting immunization at 4 weeks. In this respect, Groups 1-15 were immunized with either AdNull, AdPfAMA1(SG), AdPfMSP1$_{42}$(SG), a cocktail of AdPfAMA1 (SG) and AdPfMSP1$_{42}$ (SG), or AdE1 (MSP1$_{42}$SSG/mCMVAMASG). The mice of group 16 were naïve mice. Mice were sacrificed at 2 weeks or 6 weeks post-immunization. Antibody responses for mice in groups 11-16 were evaluated by ELISA assays as described in Example 2.

Figure 2:
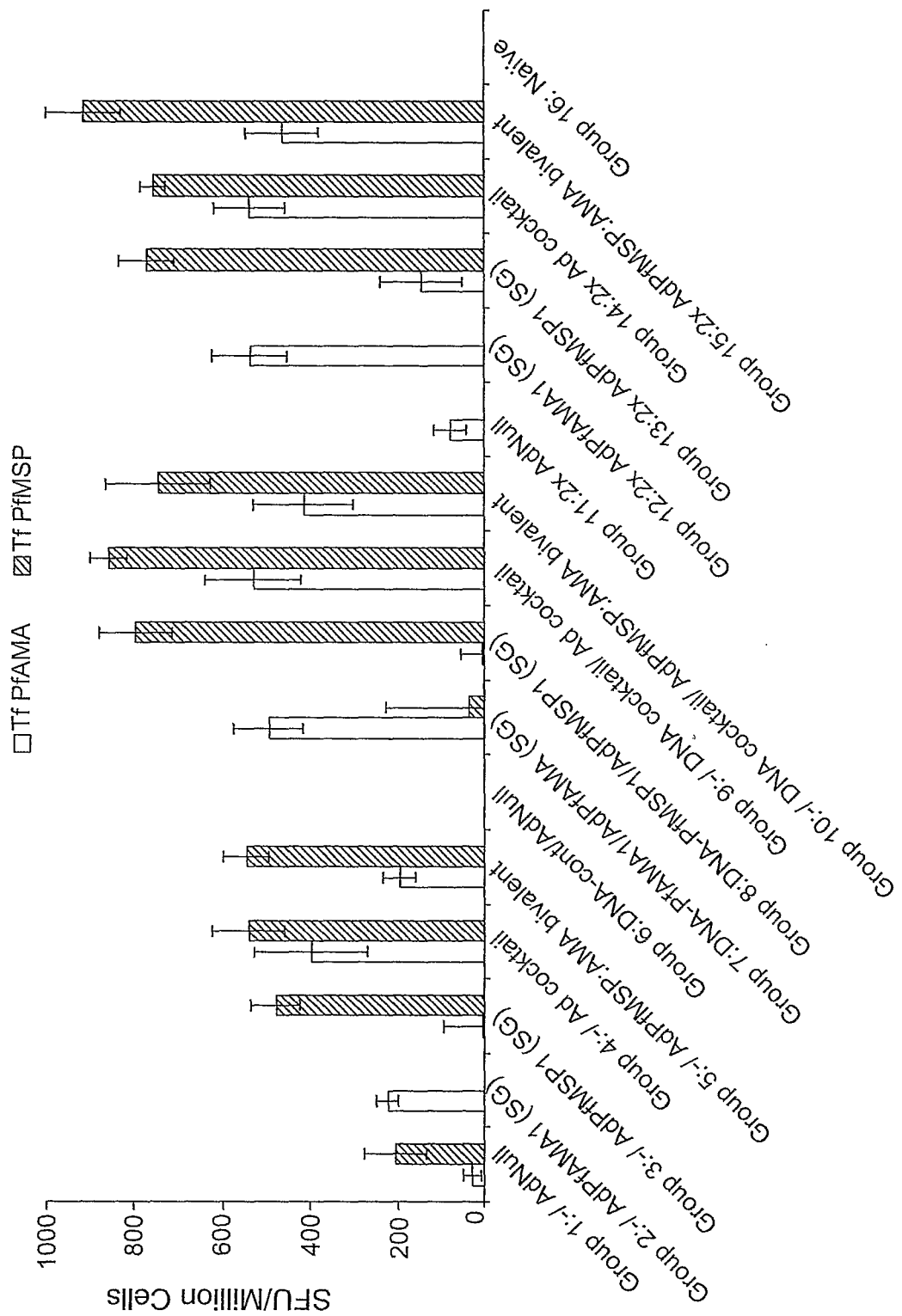
FIG. 2 is a graph depicting the results of an IFN-γ ELIspot assay conducted six weeks after mice were immunized according to the prime-boost regimen set forth in Example 4.
Figure 3:
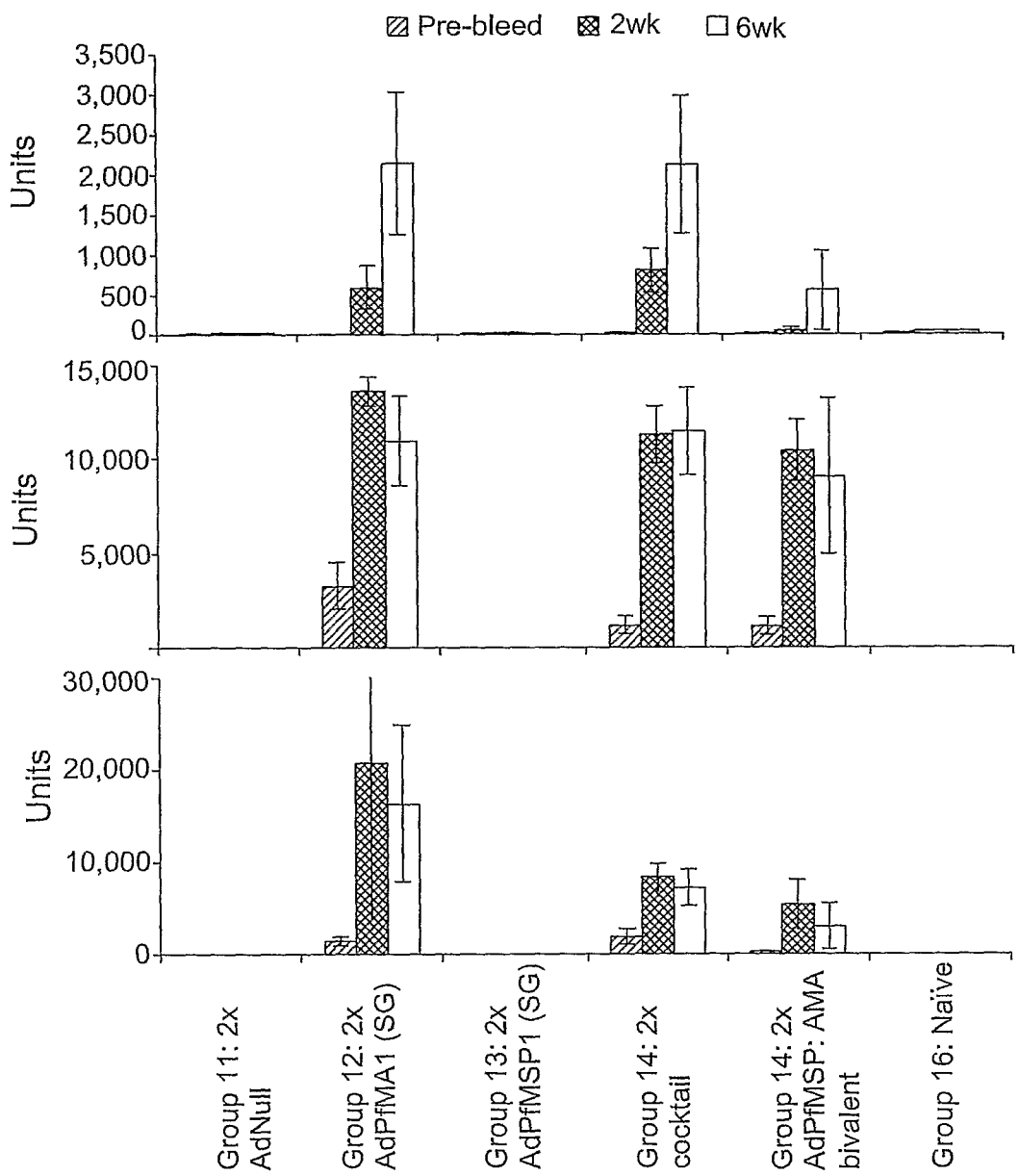
FIG. 3 is a graph depicting the results of a PfAMA1-specific ELISA assay conducted after mice were immunized according to the prime-boost regimen set forth in Example 4. The top panel corresponds to mice that did not receive a priming immunization. The middle panel corresponds to mice that received a DNA construct as a priming immunization and an adenoviral vector as a boost. The lower panel corresponds to mice that received an adenoviral vector as a priming immunization and an adenoviral vector as a boost.
Figure 4:
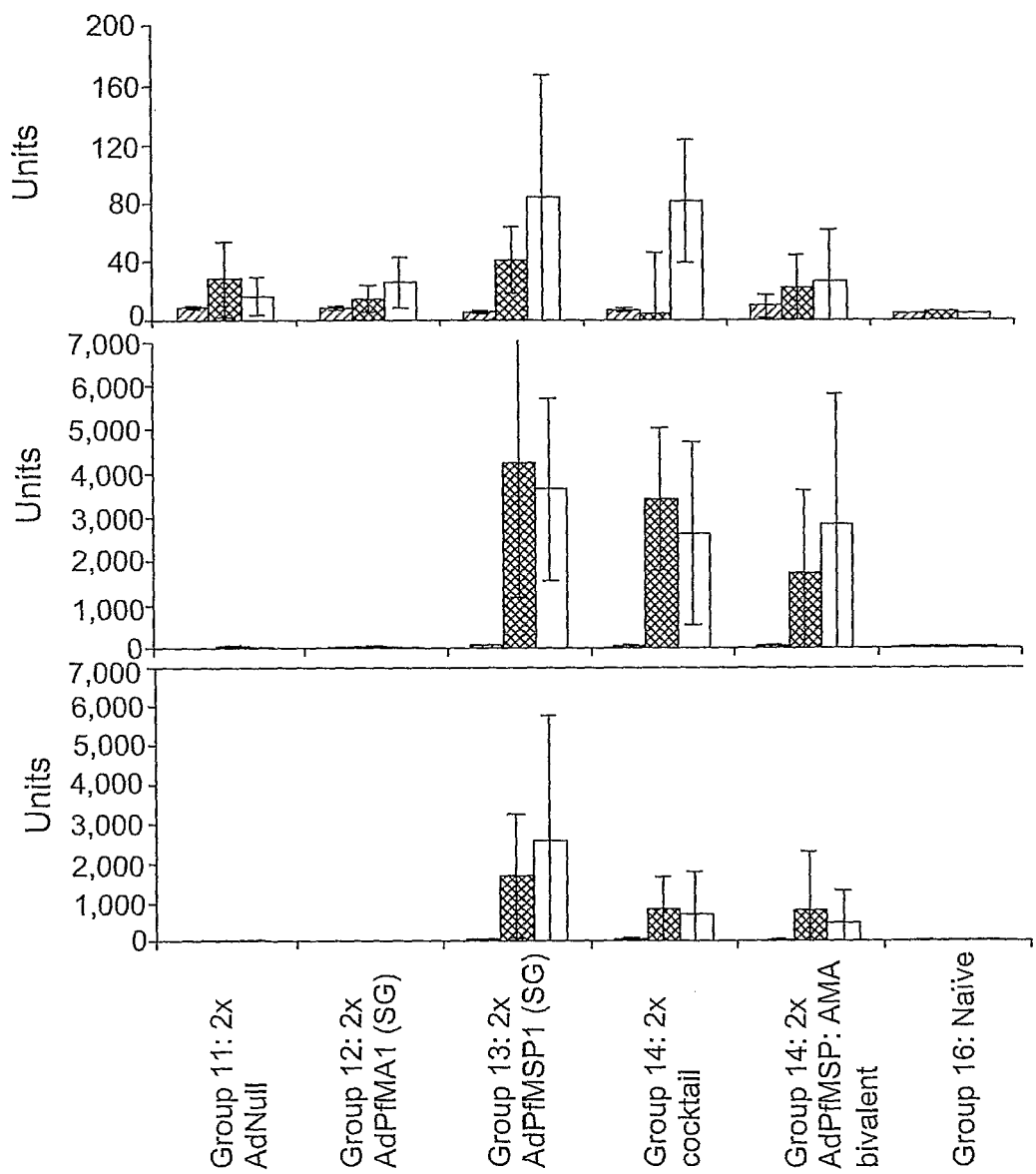
FIG. 4 is a graph depicting the results of a PfMSP1$_{42}$-specific ELISA assay conducted after mice were immunized according to the prime-boost regimen set forth in Example 4. The top panel corresponds to mice that did not receive a priming immunization. The middle panel corresponds to mice that received a DNA construct as a priming immunization and an adenoviral vector as a boost. The lower panel corresponds to mice that received an adenoviral vector as a priming immunization and an adenoviral vector as a boost.

The results of these experiments are set forth in FIGS. 1-4. FIG. 1 illustrates the results of the IFNγ ELIspot analysis of treated mice at two weeks post-immunization. FIG. 2 illustrates the results of the IFNγ ELIspot analysis of treated mice at six weeks post-immunization. FIGS. 3 and 4 illustrate the results of the ELISA assays for the AMA1 protein and MSP1$_{42}$ protein, respectively.

The results of this example demonstrate the production and immunogenicity of an inventive adenoviral vector comprising two heterologous nucleic acid sequences, wherein each nucleic acid sequence encodes a *Plasmodium* antigen and is operably linked to at least one promoter.

Example 5

This example demonstrates the preparation of an adenoviral vector comprising a heterologous nucleic acid sequence encoding a *P. falciparum* pre-erythrocytic stage antigen.

Serotype 5 E1/E3/E4-deficient adenoviral vectors containing, in place of the deleted E1 region, a nucleic acid sequence encoding the *P. falciparum* CSP gene or SSP-2 gene were generated using the methods described in, for example, International Patent Application Publication No. WO 99/15686 and U.S. Pat. No. 6,329,200. The CSP gene or SSP-2 gene was operably linked to one of the following promoters: hCMV, mCMV, RSV, or Ub. Each of the adenoviral vector constructs was named according to the *Plasmodium* gene encoded thereby and the promoter used to control the *Plasmodium* gene.

To determine the extent to which in vitro antigen expression levels are affected by promoter usage, human embryonic lung (HEL) cells were infected with one of six adenoviral vectors comprising a PfSSP2 expression cassette inserted into the deleted E1 region of the vector. All of the expression cassettes utilized a codon-optimized PfSSP2 gene, except the vector AdCMV.PfSSP2n, which contained the native SSP-2 sequence. The vector AdCMV.PfSSP2d1TMCT comprises a nucleic acid sequence encoding a carboxy-terminus deletion of the PfSSP2 amino acid sequence that removes the transmembrane domain of the protein. The vectors AdCMV.PfSSP2, AdRSV.PfSSP2, AdUb.PfSSP2, and AdmCMV.PfSSP2 comprise a nucleic acid sequence encoding PfSSP2 operably linked to a hCMV promoter containing a synthetic splicing signal, the RSV promoter, the Ub promoter, or the mCMV promoter, respectively.

An immunoblot assay demonstrated that the highest levels of PfSSP2 expression were observed when the hCMV and mCMV promoters were used to control expression of the codon-optimized PfSSP2 antigen. Comparison of AdCMV.PfSSP2 with AdCMV.PfSSP2n indicates that the use of the codon-optimized PfSSP2 sequence enhanced PfSSP2 expression approximately 100-fold relative to the native sequence. PfSSP2 expression from the RSV and Ub promoters was reduced by about 20- to 100-fold relative to the hCMV promoter.

The results of this example demonstrate the production of adenoviral vectors comprising a heterologous nucleic acid sequence encoding a *P. falciparum* pre-erythrocytic stage antigen operably linked to various different promoters.

Example 6

This example demonstrates the immunogenicity of an adenoviral vector encoding a *P. falciparum* pre-erythrocytic stage antigen in vivo.

The immunogenicity induced by the recombinant adenoviral vectors described in Example 4 was evaluated in a mouse model. Specifically, cohorts of six female BALB/c mice ages 3-6 weeks (n=6 per group) were immunized intramuscularly in the tibialis anterior muscle with vectors expressing mammalian codon-optimized PfSSP2 from the RSV promoter, hCMV promoter, mCMV promoter, or Ub promoter, or non-codon optimized (i.e., native) PfSSP2 expressed from the hCMV promoter at a dose of 1×10$^8$ pu in a total volume of 100 µl split between the two muscles. Mice were divided into 10 groups, of which groups 2-4 received a priming immunization of PfSSP2 DNA followed by a boosting immunization at 4 weeks with each of the PfSSP2 adenovectors. Groups 5-7 were immunized with two doses of the PfSSP2 adenovectors at 4-week intervals. Groups 8-10 were immunized with a single dose of the PfSSP2 adenovectors. Mice were sacrificed at 2 weeks or 6 weeks post-immunization. CD8+ and CD4+ T cell responses were measured by intercellular cytokine staining (ICS) or IFN-γ ELIspot following in vitro restimulation with pools of synthetic peptides derived from PfSSP2 and presented by A20/2J target cells. Nonimmunized naïve mice of group 1 were evaluated in parallel.

A robust immune response was observed when PfSSP2 was expressed from the hCMV or mCMV promoters, but not from the RSV promoter. Moreover, a high correlation between in vitro IFN-γ responses and in vivo protective immunity was noted ($r^2$=0.903), and constructs utilizing the RSV promoter were poorly effective at inducing sterile protection against either short-term (2 weeks, 6 weeks, or 12 weeks post immunization) or long-term (6 months) pathogen challenge. In vivo immune responses induced by the native PfSSP2 adenovector expressed from the hCMV promoter were poor, with frequencies and magnitudes or responses comparable to those induced by vectors comprising the RSV promoter. These data confirm that candidate adenovector malaria vaccines should utilize mammalian codon optimized genes in preference to native gene sequences.

The T cell responses induced by the adenovectors were predominantly of the CD8+ phenotype, although CD4+ T cell responses were detected by intracellular cytokine staining. The profile of relative immunogenicity of promoters for induction of CD4+ T cell responses was similar to that of CD8+ T cell responses. These data are consistent with the results of other studies using PyCSP in the *P. yoelii* murine model. Since protection against pre-erythrocytic stage malaria is mediated predominantly by CD8+ T cells, with CD4+ T cells playing a secondary role, the profile and phenotype of immune responses induced by the recombinant adenovirus vectors described herein are desirable for protection against *Plasmodium* challenge.

By extrapolation, these data also suggest that the hCMV and mCMV promoters, but not the RSV promoter, may be effective at inducing protective immunity against *P. falciparum*. Also consistent with the data, there was not a significant difference between PfSSP2 antigen specific responses induced by the hCMV or mCMV promoters at the doses tested. The data also established 1×10⁸ pu as an effective dose, which was selected as the standard dose for subsequent studies.

The adenoviral vectors described in Example 5 also were evaluated for their capacity to induce antigen specific antibody responses. In particular, antibody responses elicited by constructs expressing PfSSP2 from high, medium, or low expressing promoters were compared. The results of this analysis are set forth in Table 3. The antibody responses were comparable to the T cell responses elicited by the tested adenoviral vectors. In this respect, the RSV promoter constructs were poorly immunogenic, and the human and murine CMV promoters were highly effective in inducing antigen specific antibody responses.

TABLE 3

| | Prime | | Antibody Titer | |
|---|---|---|---|---|
| Group | Construct | Boost Construct | 4 weeks | 8 weeks |
| 1 | None | none | 7 | 7 |
| 2 | DNA | Ad-RSV PfSSP2 | 6,249 | 2,928 |
| 3 | DNA | AdCMVPfSSP2 | 4,227 | 5,689 |
| 4 | DNA | Ad-mCMVPfSSP2 | 5,059 | 3,433 |
| 5 | AdRSV | AdRSVPfSSP2 | 1,373 | 1,762 |
| 6 | AdCMV | AdCMVPfSSP2 | 9,910 | 3,640 |
| 7 | AdmCMV | AdmCMVPfSSP2 | 3,066 | 3,350 |
| 8 | None | AdRSVPfSSP2 | 9 | 8 |
| 9 | None | AdCMVPfSSP2 | 1,869 | 10,010 |
| 10 | None | AdmCMVPfSSP2 | 684 | 3,789 |

The results of this example demonstrate the immunogenicity of an adenoviral vector encoding a *P. falciparum* pre-erythrocytic stage antigen operably linked to an hCMV, mCMV, or RSV promoter in vivo.

Example 7

This example demonstrates the preparation of an adenoviral vector comprising two heterologous nucleic acid sequences encoding *P. falciparum* pre-erythrocytic stage antigens.

An E1/E4-deficient adenoviral vector was constructed comprising the PfCSP gene modified to contain a GPI anchor inhibiting tail (PfCSPt) in an expression cassette located in the deleted E1 region and the PfLSA gene in an expression cassette located in the deleted E4 region of the adenovirus. Specifically, an E1 shuttle vector was constructed which expresses the PfCSPt antigen from the hCMV promoter. An E4 shuttle vector that expresses the PfLSA antigen from the mCMV promoter also was generated using the methods described in, for example, International Patent Application Publication No. WO 99/15686 and U.S. Pat. No. 6,329,200. These shuttle vectors were recombined with plasmids generated by the AdFast™ technology (GenVec, Inc., Gaithersburg, Md.) (see International Patent Application Publication No. WO 99/15686 and U.S. Pat. No. 6,329,200) to generate a new adenovector plasmid. This plasmid was converted into an adenovirus and expanded to generate a high titer vector stock of the adenovector called AdE1(CSPt)E4(mCMV.LSA). The high titer stock of the adenoviral vector was fully certified, and its genetic structural identity was confirmed by a PCR-based assay. Immunoblot assays confirmed that this bivalent vector resulted in efficient expression of both the PfCSPt and PfLSA antigens in vitro.

T-cell immune responses induced by the recombinant adenoviral vectors were evaluated as described in Example 2. In particular, mice were immunized with one or two doses of either a control vector lacking any *P. falciparum* antigen (AdNull), an E1/E4-deficient adenovector encoding only the CSPt antigen (AdPfCSPt), an E1/E4-deficient adenovector encoding only the LSA antigen (AdPfLSA), a cocktail of AdPfCSPt and AdPfLSA, or AdE1(CSPt)E4(mCMV.LSA). Mice were sacrificed at 2 weeks and 6 weeks post-immunization. Antibody responses for each group of treated mice were evaluated by ELISA assays as described in Example 2.

Figure 5:
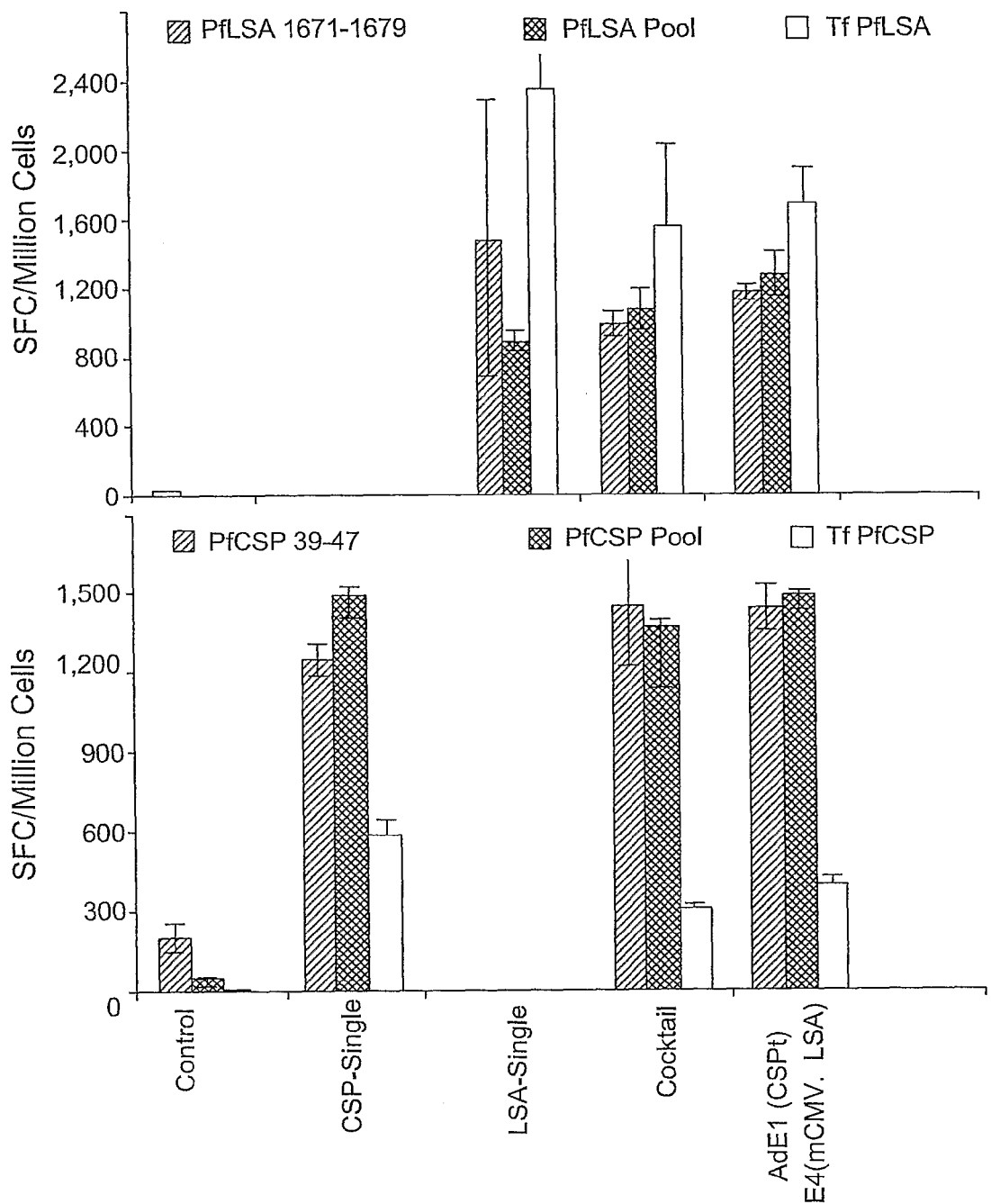
FIG. 5 is a graph depicting the results of an IFN-γ ELIspot assay conducted after mice were immunized according to the regimen set forth in Example 7. The top panel illustrates the LSA1-specific T-cell response, while the lower panel illustrates the CSP-specific T-cell response.
Figure 6:
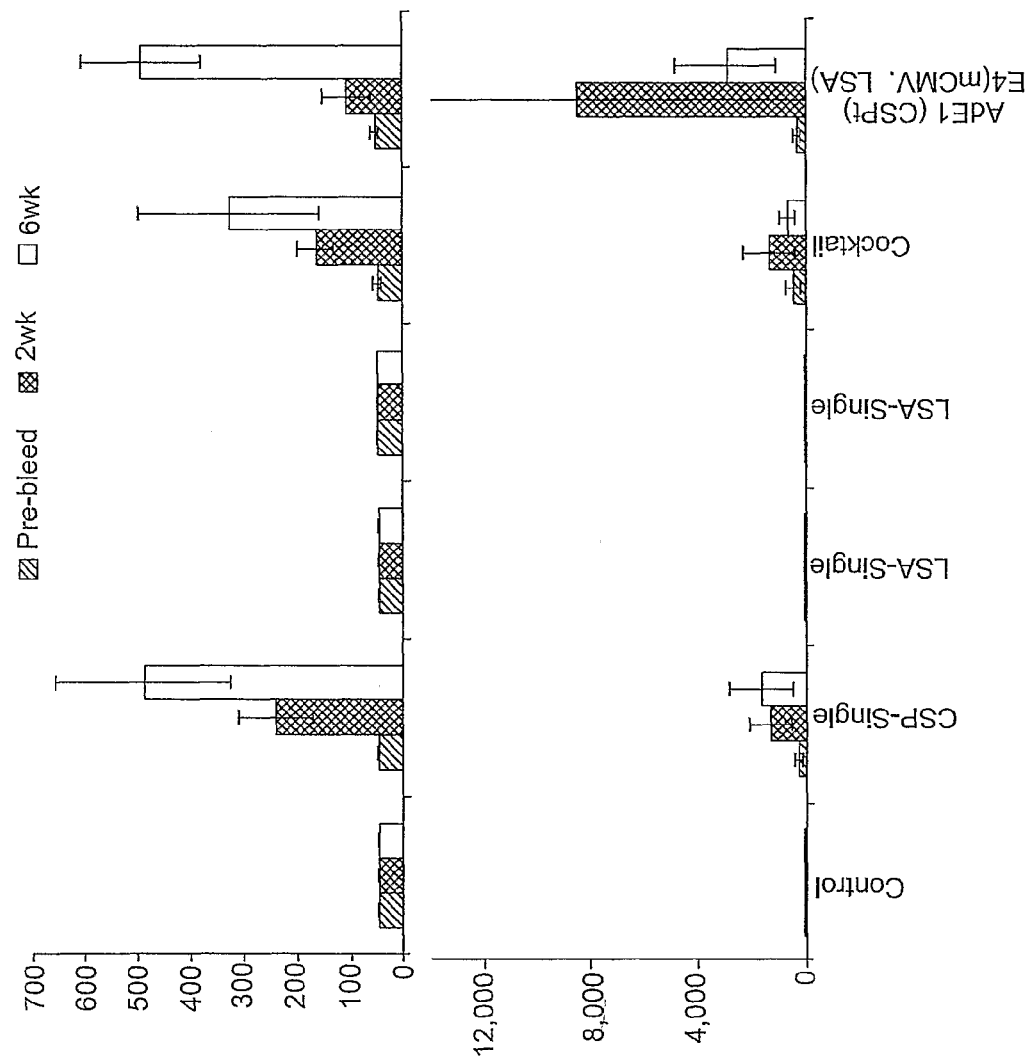
FIG. 6 is a graph depicting the results of an ELISA assay conducted after mice were immunized according to the regimen set forth in Example 7. The top panel corresponds to mice that received one dose of each adenoviral vector. The lower panel corresponds to mice that received two doses of each adenoviral vector.

The results of these experiments are set forth in FIGS. 5 and 6. FIG. 5 illustrates the results of the IFNγ ELIspot analysis of treated mice at six weeks post-immunization. FIG. 6 illustrates the results of the ELISA assays for mice receiving a single dose or double dose of the adenoviral vectors described above. These results demonstrate that a bivalent adenoviral vector encoding two pre-erythrocytic stage malaria antigens induced strong T-cell and antibody responses against both antigens in vivo.

Example 8

This example demonstrates the preparation of an adenoviral vector comprising three heterologous nucleic acid sequences, each of which are operably linked to at least two different promoters.

Figure 7:
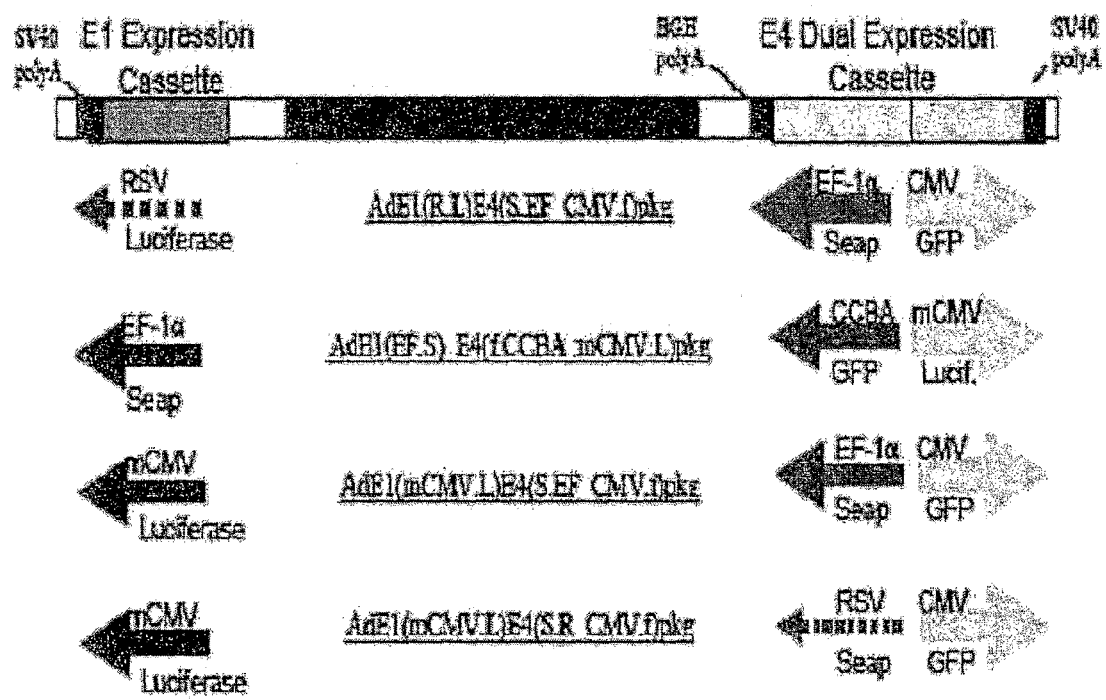
FIG. 7 is a diagram of trivalent E1/E3/E4-deleted adenoviral vector constructs expressing three different marker genes (i.e., luciferase, green fluorescent protein (GFP), and secreted alkaline phosphatase (SEAP)).

Trivalent E1/E3/E4-deleted adenoviral vectors comprising three nucleic acid sequences encoding marker genes were generated by incorporating a single expression cassette inserted in place of the E1 region, and a dual expression cassette inserted in place of the E4 region. The marker genes tested included luciferase, secreted alkaline phosphatase (SEAP), and green fluorescent protein (GFP). The promoters tested included the RSV promoter, a human CMV promoter with a synthetic splicing signal (CMV), the mouse CMV promoter (mCMV), the CCBA promoter, and the EF-1α promoter. The trivalent constructs that were generated are schematically represented in FIG. 7.

Using the methods described in International Patent Application Publication No. WO 99/15686 and U.S. Pat. No. 6,329, 200, all trivalent constructs were rescued from an adenovector plasmid with similar efficiency as control plasmids. The total yield of purified vector stocks of two of the adenoviral vector constructs, AdE1(EF.S)E4(f.CCBA_mCMV.L) and AdE1(mCMV.L)E4(S.R_CMV.f), were higher than the other tested adenoviral vectors suggesting that one vector design may have growth advantages over another.

To determine the growth characteristics of these vectors, growth curve experiments were performed. 293-ORF6 cells (see, Brough et al., *J. Virology*, 70: 6497-6501 (1996)) were infected with three lysates of the trivalent vectors including the two with the poorest yields in production. Cells were obtained at 48 and 72 hours post-infection and analyzed for active vector particles by using the focus-forming unit (ffu) assay. Infections with a multiplicity of infection (MOI) of 20 ffu/cell resulted in significant vector yields for all of the trivalent vectors. Trivalent vector yields were similar to the yields obtained with a control adenovector that carries only one expression cassette (AdL.11D).

The generation of an adenoviral vector expressing both PfCSP and PfSSP2 has proven difficult because these antigens inhibit the conversion of adenovector plasmid to adenovirus particle, and yields of purified PfSSP2-expressing adenovectors have been approximately 10-fold lower than most other adenovector stocks. To address this problem, adenovectors expressing PfSSP2 mutants were generated. In this regard, PfSSP2-4 contains a C-terminal deletion of that removes the transmembrane domain and C-terminus of the SSP2 protein. PfSSP2-6 contains a deletion in the thrombospondin domain of PfSSP2. E1/E3/E4-deleted serotype 5 adenoviral vectors expressing each of these mutant SSP2 genes were analyzed in growth curve experiments in parallel with the adenoviral vectors expressing wild-type PfSSP2 described above.

The adenovector encoding PfSSP2-6 grew to significantly lower titers than the adenovector encoding wild-type PfSSP2 or the adenovector encoding PfSSP2-4, and was therefore not analyzed further. The best growth performance was observed with the adenovector comprising the native PfSSP2 nucleotide sequence. The adenovectors that expressed the codon-optimized SSP2 antigen from the mCMV promoter grew well in this assay, and induced potent immune responses in the mouse.

The results of this example demonstrate the production of an inventive adenoviral vector comprising three heterologous nucleic acid sequences, wherein each nucleic acid sequence is operably linked to at least two different promoters.

Example 9

This example demonstrates the preparation of an adenoviral vector comprising three heterologous nucleic acid sequences, wherein each heterologous nucleic acid sequence encodes a Plasmodium antigen.

E1/E3/E4-deleted serotype 5 adenoviral vectors were generated which express both PfLSA and PfCSP from dual expression cassettes located in the E1 and E4 regions of the viral genome. Preliminary results indicate that the E1 expression vectors are growing well. In addition, expression cassettes for a trivalent adenovector expressing three pre-erythrocytic stage Plasmodium antigens were constructed. These expression cassettes comprise the PfSSP2 gene inserted into an E1 deletion site, and the PfLSA and PfCSP genes as part of a dual expression cassette inserted into an E4 deletion site.

Example 10

This example demonstrates the preparation of an adenoviral vector comprising a modified hexon protein that exhibits reduced recognition by the host immune system.

Diversity in the hexon protein of an adenovirus is generated by first making random mutations in the gene encoding hexon by, for example, polynucleotide shuffling or error-prone PCR using methods described in, for example, Stemmer, supra, Chemy et al., supra, and Schmidt-Dannert et al., supra. Mutated hexon genes are incorporated into a library of E1-deficient Ad5 adenoviral vectors, wherein each Ad5 vector comprises an Ad35 fiber protein and a dual expression cassette which expresses two marker genes (e.g., luciferase and green fluorescent protein) inserted into the E1 region. Library vectors are propagated in suitable host cells, and vectors encoding potential hexon variants of interest are rescued under competitive conditions in the presence of human anti-Ad5 neutralizing antibodies. Rescued vectors are either expanded in the presence of anti-Ad5 neutralizing antibodies, purified, or cloned, and hexon variants are sequenced.

The modified hexon proteins are then tested for the ability to avoid human neutralizing antibodies in vivo. Specifically, an adenoviral vector comprising a modified hexon protein encoded by a variant nucleic acid sequence as described above, and encoding a P. yoelli CSP protein (Ad(mod)-PyCSP), is generated. BALB/c mice (n=20 per group) are immunized with a $1\times10^8$ pu dose of Ad(mod)-PyCSP or an unmodified PyCSP adenoviral vector (Ad-PyCSP), two or three times at 6 week intervals. In some groups, mice are pre-immunized with wild-type adenovirus (serotype 5) to generate pre-existing anti-Ad5 neutralizing antibodies prior to vaccination. Sera are collected pre-immunization and at 14 days post-immunization. At 14 days after the third immunization, 6 mice from each group are sacrificed for T cell studies, and 14 mice per group are challenged for evaluation of protective efficacy. Mice that are protected against parasite challenge are assayed and re-challenged at 6 months post-boost to evaluate the duration of vaccine-induced immune responses and protective immunity.

Depending upon the results of these experiments, the dose of adenoviral vector may be increased (e.g., to $1\times10^{10}$ pu) to confirm that the potency of the hexon-modified adenovirus is not limited by neutralizing antibodies generated during the vaccination process. Alternatively, the interval between immunizations may be increased to more optimally generate robust antigen-specific immune responses. In yet another alternative, the level of preexisting neutralizing antibodies at the time of priming may be increased.

Example 11

This example demonstrates the preparation of an adenoviral vector comprising a modified hexon protein.

Serotype 5 adenoviral vectors were generated containing Ad5-Ad2 chimeric loops in the hexon protein. In particular, two E1/E4-deficient adenoviral vectors were generated, one of which encoded the luciferase gene, while the other encoded the PyCSP antigen. The Ad5-A2 chimeric hexon proteins were generated by replacing the hexon DE1 loop containing hypervariable regions 1-6 of Ad5 (i.e., Ad5 hexon amino acids 132-315) and the FG loop containing hypervariable regions 7-9 from Ad5 (i.e., Ad5 hexon amino acids 420-449) with the corresponding loops from a serotype 2 adenovirus (i.e., Ad2 hexon amino acids 132-327, and Ad2 hexon amino acids 432-465). Each vector was grown to high titers and wad produced and purified for in vivo experiments according to methods described herein.

A similar approach was used to generate a serotype 5 adenoviral vector comprising Ad5-Ad43 chimeric loops in the hexon protein. In this regard, Ad5-Ad43 chimeric hexon proteins were generated by replacing the FG1 loop, corresponding to Ad5 hexon amino acids 418-449, with the FG1 loop of Ad43, corresponding to Ad43 hexon amino acids 410-440. In addition, the Ad5 DE1 loop, corresponding to Ad5 hexon amino acids 123-316 were replaced with the DE1 loop of Ad43, corresponding to Ad43 hexon amino acids 123-308. Adenoviral vectors carrying the Ad5-Ad43 DE1 loop exchange were not rescued, suggesting that some of the exchanged sequences were necessary for structural features of the Ad5 hexon. The DE1 loop is composed of six hypervariable regions and intervening sequences, which are more conserved across serotypes. The intervening sequences are more highly conserved between the two group C hexons (Ad2 and Ad5) than they are between Ad5 and the group D hexon (Ad43).

In order to generate an Ad5 hexon that is not sensitive to Ad5 neutralizing antibodies, but is capable of folding into a highly structured adenovirus capsid, chimeric DE1 loops consisting of the hypervariable regions of Ad43 inserted into the Ad5 hexon with intervening sequences between the hypervariable regions derived from Ad5 were synthesized. The specific amino acid substitutions made in the Ad5 hypervariable regions are set forth in Table 4.

TABLE 4

| Ad5 HVR Region | Substitution Start Point (Ad5 hexon amino acids) | Substitution End Point (Ad5 hexon amino acids) |
|---|---|---|
| HVR1 | 136-138 | 164-165 |
| HVR2 | 184-188 | 192-194 |
| HVR3 | 212 | 218-220 |
| HVR4 | 248-252 | 258-260 |
| HVR5 | 268-271 | 279-281 |
| HVR6 | 300-305 | 310-315 |

One example of a specific Ad5-Ad43 hexon loop chimera generated includes a substitution of HVR1 (Ad5 hexon amino acids 136-165), HVR2 (Ad5 hexon amino acids 188-194), HVR3 (Ad5 hexon amino acids 212-220), HVR4 (Ad5 hexon amino acids 252-260), HVR5 (Ad5 hexon amino acids 268-281), and HVR6 (Ad5 hexon amino acids 303-310) with the corresponding HVRs from Ad43.

This example demonstrates the generation of serotype 5 adenoviral vectors comprising chimeric hexon proteins designed to avoid pre-existing host immunity to Ad5 vectors.

Example 12

To assess the capability of the adenoviral vectors generated in Example 11 to circumvent the potential adverse effects of pre-existing host Ad5 neutralizing antibodies, a prime-boost immunization strategy using these vectors will be performed in a mouse model.

One experiment will assess the ability of neutralizing antibodies generated against Ad5, Ad2, and Ad43 in mice to neutralize adenoviral vectors comprising the chimeric hexon proteins described in Example 11. Specifically, seven different groups of Balb/c mice will receive a priming immunization containing $1\times10^{10}$ particle units (pu) of one of the following adenoviral constructs: (1) an E1-deficient Ad5 vector containing an Ad35 fiber protein (Ad5E1 (L)F35), (2) an E1/E4-deficient Ad5 vector (AdE1(L)11D), (3) wild-type Ad2, (4) wild-type Ad34, (5) wild-type Ad43, (6) wild-type Ad5, and (7) wild-type Ad35. At 21 days post priming immunization, whole blood will be harvested to obtain serum for neutralizing antibody analysis. At day 22, mice will receive a boosting immunization containing $1\times10^{10}$ pu of one of the hexon-modified adenoviral vectors described in Example 11. At day 43 (i.e., 21 days after boost), whole blood will again be harvested from treated mice to assess the neutralizing antibody response.

A second experiment will assess the ability of the hexon-modified adenoviral vectors of Example 11 to circumvent Ad5 neutralizing antibodies. Specifically, T cell and antibody responses generated in response to a test antigen, PyCSP, in the presence and absence of Ad5 neutralizing antibody will be evaluated. Balb/c mice are divided into 12 treatment groups. At 21 days prior to immunization, four groups of mice are exposed to wild-type Ad, and one group is exposed to an E1/E4-deficient Ad5 vector lacking a transgene (AdNull). Eighteen days later, Ad5-exposed mice are bled to assess neutralizing antibody levels. The following day, all 12 groups are administered a priming immunization containing $1\times10^{8}$ pu/mL of one of the following adenoviral vector constructs: (1) Ad5-PyCSP, which is an E1/E4-deficient Ad5 vector comprising the PyCSP gene inserted into the E1 region, (2) Ad5PyCSP(H)2-2, which is an E1-deficient Ad5 vector comprising the PyCSP gene inserted into the E1 region and a chimeric hexon comprising the Ad2 DE1 loop and the Ad2 FG1 loop, (3) Ad35-PyCSP, which is an E1-deficient Ad35 vector comprising the PyCSP gene inserted into the E1 region, and (4) Ad35PyCSP.F(5S), which is similar to Ad35-PyCSP, except that it comprises an Ad5 fiber protein in place of the Ad35 fiber protein. The mice exposed to AdNull were primed with a dose of AdNull, and unimmunized naïve mice also served as controls.

Six weeks after administration of the priming immunization, each group of mice received a boosting immunization containing $1\times10^{8}$ pu/mL of Ad5-PyCSP, Ad5PyCSP(H)2-2, Ad35-PyCSP, or Ad35PyCSP.F(5S). The specific prime/boost immunizations are set forth in Table 5.

TABLE 5

| Group | Prime | Boost |
|---|---|---|
| 1 | Naïve | Naïve |
| 2 | AdNull | AdNull |
| 3 | Ad5-PyCSP | Ad5-PyCSP |
| 4 | Ad5PyCSP(H)2-2 | Ad5PyCSP(H)2-2 |
| 5 | Ad5-PyCSP | Ad5PyCSP(H)2-2 |
| 6 | Ad5PyCSP(H)2-2 | Ad5-PyCSP |
| 7 | Ad5-PyCSP | Ad5-PyCSP |
| 8 | Ad5PyCSP(H)2-2 | Ad5PyCSP(H)2-2 |
| 9 | Ad5-PyCSP | Ad5PyCSP(H)2-2 |
| 10 | Ad5PyCSP(H)2-2 | Ad5-PyCSP |
| 11 | Ad35-PyCSP | Ad35-PyCSP |
| 12 | Ad35PyCSP.F(5S) | Ad35PyCSP.F(5S) |

Two weeks after administration of the boosting immunization, mice will be bled and T-cell and antibody responses will be measured using methods described herein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adenoviral vector comprising an adenoviral genome comprising *Plasmodium* antigen-encoding nucleic acid sequences, wherein the *Plasmodium* antigen-encoding nucleic acid sequences consist of
   (i) a nucleic acid sequence encoding a *Plasmodium* sporozoite surface protein 2 (SSP2),
   (ii) a nucleic acid sequence encoding a *Plasmodium* circumsporozoite protein (CSP), and
   (iii) a nucleic acid sequence encoding a *Plasmodium* apical membrane antigen 1 (AMA-1),
   wherein the *Plasmodium* antigen-encoding nucleic acid sequences are operably linked to at least two different heterologous promoters.

2. The adenoviral vector of claim 1, wherein the adenoviral vector comprises a hexon protein of a first adenoviral serotype wherein one or more of the hypervariable regions (HVRs) of the hexon protein have been removed and replaced with corresponding amino acid residues from an adenovirus of a second serotype that differs from the first serotype.

3. The adenoviral vector of claim 2, wherein the adenoviral vector comprises a hexon protein of a first adenoviral serotype wherein all of the HVRs of the hexon protein have been removed and replaced with corresponding amino acid residues from an adenovirus of a second serotype that differs from the first serotype.

4. The adenoviral vector of claim 2, wherein the adenoviral vector is a serotype 5 adenoviral vector comprising a hexon protein wherein one or more of the HVRs of the hexon protein have been removed and replaced with corresponding amino acid residues from a serotype 43 adenovirus.

5. The adenoviral vector of claim 1, wherein the adenoviral vector comprises a hexon protein wherein one or more of the HVRs of the hexon protein are removed and replaced with a non-adenoviral amino acid sequence.

6. The adenoviral vector of claim 5, wherein the non-adenoviral amino acid sequence comprises a *Plasmodium* epitope sequence.

7. The adenoviral vector of claim 6, wherein the *Plasmodium* epitope sequence comprises a *Plasmodium* circumsporozoite protein.

8. A method of inducing an immune response against malaria in a mammal, which method comprises administering a therapeutically effective amount of the adenoviral vector of claim 1 to the mammal, wherein the antigens are expressed in the mammal to induce an immune response against malaria.

* * * * *